US012685815B2

(12) United States Patent
Dave et al.

(10) Patent No.: US 12,685,815 B2
(45) Date of Patent: ***Jul. 21, 2026

(54) SYSTEM FOR DRUG DELIVERY

(71) Applicant: Manta MedTech LLC, Newark, DE (US)

(72) Inventors: Raju S. Dave, Gaithersburg, MD (US);
Xing Su, Santa Clara, CA (US);
Himanshu Verma, McLean, VA (US);
Ashish Shah, East Amherst, NY (US);
Kenta Alten, Los Altos Hills, CA (US)

(73) Assignee: Manta MedTech LLC

( * ) Notice: Subject to any disclaimer, the term of this patent is extended or adjusted under 35 U.S.C. 154(b) by 0 days.

This patent is subject to a terminal disclaimer.

(21) Appl. No.: 19/264,417

(22) Filed: Jul. 9, 2025

(65) Prior Publication Data

US 2025/0339609 A1 Nov. 6, 2025

Related U.S. Application Data

(63) Continuation-in-part of application No. 19/006,285, filed on Dec. 31, 2024, now Pat. No. 12,390,581.
(Continued)

(51) Int. Cl.
*A61M 5/142* (2006.01)
*A61M 5/14* (2006.01)
*A61M 5/145* (2006.01)
(52) U.S. Cl.
CPC ...... *A61M 5/14248* (2013.01); *A61M 5/1409* (2013.01); *A61M 5/14526* (2013.01);
(Continued)
(58) Field of Classification Search
CPC .......... A61M 5/14276; A61M 5/14526; A61M 5/16804; A61M 39/22;
(Continued)

(56) References Cited

U.S. PATENT DOCUMENTS 5,209,746 A * 5/1993 Balaban ............... A61K 9/0004
604/890.1
5,308,348 A 5/1994 Balaban et al.
(Continued)

FOREIGN PATENT DOCUMENTS

WO 2008085222 A2 7/2008
WO 2025147449 A1 7/2025

OTHER PUBLICATIONS

Extended European search report issued for EP Application 25188558.8, mailed on Dec. 12, 2025.

*Primary Examiner* — Chelsea E Stinson
*Assistant Examiner* — Anh Bui
(74) *Attorney, Agent, or Firm* — Davé Law Group, LLC; Raj S. Davé

(57) ABSTRACT

Embodiments relate to systems comprising Active Wearable Medical Device (AWMD) with an osmotic chamber containing or configured to receive an osmotic agent, a permeability module for fluid ingress, and a drug chamber holding a drug. A compressible piston, positioned between the chambers, moves longitudinally as a whole during operation. The compressible piston advances toward the drug chamber when a valve opens, enabling drug release through one or more outlets, and retracts when the valve closes, driven by osmotic pressure. A valve module regulates this flow. The system also comprises a fluid chamber containing fluid and a semipermeable membrane coupling it to the AWMD. A channel connected to the drug outlets delivers the drug externally.

20 Claims, 16 Drawing Sheets

IMPLANTABLE DEVICE (OUTSIDE VIEW)

Related U.S. Application Data

(60) Provisional application No. 63/713,149, filed on Oct. 29, 2024, provisional application No. 63/707,896, filed on Oct. 16, 2024, provisional application No. 63/689,805, filed on Sep. 2, 2024, provisional application No. 63/661,654, filed on Jun. 19, 2024, provisional application No. 63/574,330, filed on Apr. 4, 2024, provisional application No. 63/566,519, filed on Mar. 18, 2024, provisional application No. 63/617,754, filed on Jan. 4, 2024, provisional application No. 63/617,057, filed on Jan. 2, 2024, provisional application No. 63/617,054, filed on Jan. 2, 2024.

(52) U.S. Cl.
CPC .............. *A61M 2202/0007* (2013.01); *A61M 2205/0216* (2013.01); *A61M 2205/3327* (2013.01); *A61M 2205/3334* (2013.01); *A61M 2209/088* (2013.01); *A61M 2210/04* (2013.01)

(58) Field of Classification Search
CPC .... A61M 2005/14208; A61M 2202/04; A61M 2205/04; A61M 2205/18; A61M 2205/3327; A61M 2205/3334; A61M 2205/3561; A61M 2205/3592; A61M 2205/50

See application file for complete search history.

(56) References Cited

U.S. PATENT DOCUMENTS

| | | | |
|---|---|---|---|
| 7,699,834 B2 * | 4/2010 | Hood | .................... A61M 5/172 |
| | | | 604/892.1 |
| 12,390,581 B1 * | 8/2025 | Dave | ..................... A61M 39/22 |
| 2014/0094770 A1 | 4/2014 | Li et al. | |
| 2025/0144291 A1 | 5/2025 | Dave | |

* cited by examiner

IMPLANTABLE DEVICE (OUTSIDE VIEW)

IMPLANTABLE DEVICE (INSIDE VIEW)

PERMEABILITY MODULE: FLAT MEMBRANE

PERMEABILITY MODULE: HOLLOW FIBRE MEMBRANE

SENSOR MODULE

DRUG MODULE

COMPRESSIBLE PISTON

UNCOMPRESSED          COMPRESSED

UNCOMPRESSED          COMPRESSED

UNCOMPRESSED          COMPRESSED

UNCOMPRESSED

COMPRESSED

UNCOMPRESSED

COMPRESSED

UNCOMPRESSED

COMPRESSED

COMPRESSED

UNCOMPRESSED

VALVE MODULE

Compact Vibrating Plate Design for a 5mm Tube

ELECTRONICS AND POWER SUPPLY

FLOWCHART FOR DATA FLOW TO AND FROM THE IMPLANTABLE DEVICE

FLOWCHART FOR DEVICE ANAMOLY DETECTION

ARTIFICIAL INTELLIGENCE (AI) MODULE

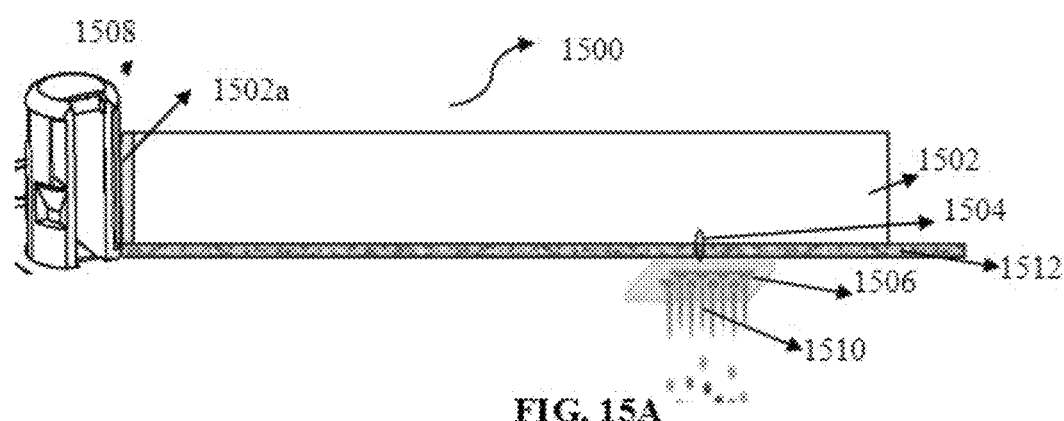
FIG. 15A
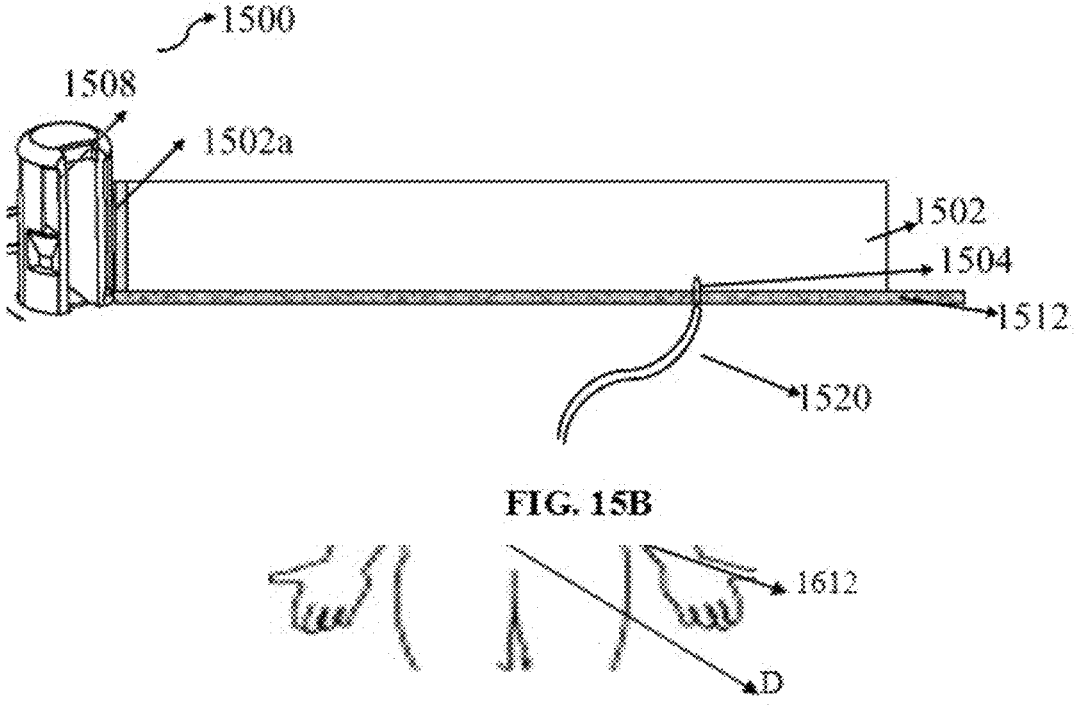
FIG. 15B
FIG. 16

1800

1802

1804

1806

1800

ENVIRONMENTAL
CHANGE

CONTROLLED
FUSE

1802

1804

LIGHT/TEMPERATURE/ pH

SYSTEM FOR DRUG DELIVERY

CROSS REFERENCE TO RELATED APPLICATIONS

This application is a Continuation-in-Part application of U.S. patent application Ser. No. 19/006,285, filed Dec. 31, 2024, titled "ACTIVE IMPLANTABLE MEDICAL DEVICE (AIMD) SYSTEM FOR DRUG DELIVERY WITH FIXED DOSE SIZE," which claims the benefit of priority from the following applications shown in the Table below, which are incorporated by reference herein in its entirety.

| U.S. patent application Nos. | Filing Date | Title of the Invention |
|---|---|---|
| 63/617054 | 2 JAN. 2024 | PERSONALIZED DRUG DOSING |
| 63/617057 | 2 JAN. 2024 | INNOVATIVE IMPLANTABLE DEVICE USING DOSING CONTROL TO PREVENT MEDICATION ERRORS |
| 63/617754 | 4 JAN. 2024 | IMPLANTABLE DEVICE FOR PRECISION DOSING |
| 63/566519 | 18 MAR. 2024 | IMPLANTABLE DRUG DELIVERY DEVICE |
| 63/574330 | 4 APR. 2024 | INNOVATIVE IMPLANTABLE DEVICE USING DOSING CONTROL TO PREVENT MEDICATION ERRORS |
| 63/661654 | 19 JUN. 2024 | DEVICE BASED TREATMENTS FOR SUBSTANCE USE DISORDERS |
| 18/781451 | 23 JUL. 2024 | ARTIFICIAL INTELLIGENCE BASED IMPLANTABLE DRUG DELIVERY SYSTEM |
| 63/689805 | 2 SEP. 2024 | IMPLANTABLE DEVICE FOR DRUG DELIVERY |
| 63/707896 | 16 OCT. 2024 | DEVICE BASED TREATMENTS FOR SUBSTANCE USE DISORDERS |
| 63/713149 | 29 OCT. 2024 | AUTOMATED OVERDOSE RESPONSE SYSTEM FOR ON-DEMAND NALOXONE DELIVERY |

TECHNICAL FIELD

This disclosure relates to implantable devices for drug delivery. Particularly, the present disclosure relates to a compressible piston for the drug delivery.

BACKGROUND

Poor medication adherence is a significant issue, leading to numerous hospital admissions and high healthcare costs. Factors contributing to nonadherence include poor insight, substance abuse, negative attitudes, side effects, and cognitive impairments. This problem is exacerbated among older adults on multiple medications, resulting in worsened health outcomes and increased mortality. Additionally, drug overdoses, particularly opioid-related, remain a severe public health crisis in the U.S., causing significant loss of life and economic burden.

Considering knowledge of a person skilled in art, there is a long-felt need to address the shortcomings in prior art and provide a system that is capable of implementing comprehensive strategies addressing issues related to clinical efficacy, toxicity, drug properties, and personalized drug dosing. It would be advantageous to have a system, method and device that considers at least some of the issues discussed above, as well as possibly other issues.

BRIEF SUMMARY

Embodiments relate to an implantable device comprising multiple modules, e.g., (1) permeability module, (2) sensor module, (3) drug chamber module, (4) valve module, (5) electronics module, and/or (6) battery module.

The device may comprise a permeability module. The permeability module may comprise a semipermeable membrane.

The device may comprise an osmotic chamber that may contain or be configured to contain an osmotic solution. The device may comprise a sensor module, e.g., to monitor physical parameters. The device may comprise a drug chamber configured to hold a drug. The device may comprise a compressible piston. The compressible piston may be positioned between the osmotic chamber and the drug chamber; The device may comprise a valve module, e.g. configured for unidirectional drug flow.

In an embodiment, the device may comprise an electronic module for control and/or a power supply module for energy.

In an embodiment, during operation, body fluid may enter through the semipermeable membrane, which may generate osmotic pressure that drives the movement of the compressible piston. The electronic module may regulate the valve to control the drug flow based on inputs from the electronic module. The device may be designed with a structure that facilitates subcutaneous implantation. It continuously releases the drug, while the sensor monitors relevant parameters, for example temperature, conductivity, and displacement.

In an embodiment, a communication network connects two or more modules or all modules, which may ensure the synchronized movement of the piston towards the drug chamber with each release, with osmotic pressure driving this action and the sensor detecting the piston's movement.

In an aspect, an active implantable medical device (AIMD) may comprise a permeability module to allow ingress of fluid into an osmotic chamber of the AIMD. The device may comprise a compressible piston. The device may comprise a drug chamber comprising a drug or configured to house a drug. The device may comprise a valve module to allow flow of the drug from the drug chamber to outside the AIMD through one or more drug outlets present in the AIMD. The compressible piston may be configured to have a crawling movement, wherein the crawling movement is repeated each dose the drug from the drug chamber such that the compressible piston as a whole moves towards the drug chamber that may lead to decrease in volume of drug chamber, wherein the compressible piston is an object that changes volume of the object by a given volume when the object changes shape from a compressed configuration to an uncompressed configuration, and furthermore the object moves longitudinally as a whole within the AIMD during operation of the AIMD.

In an aspect, a method may comprise receiving data comprising osmotic pressure data and/or an electrical conductivity from an active implantable medical device (AIMD) along with other steps. The AIMD may comprise a sensor, The method may have a step of processing the osmotic pressure data or the electrical conductivity data to determine if the osmotic pressure data or the electrical conductivity data is within ±15% of an expected osmotic pressure data or an expected electrical conductivity data. The method may have a step of notifying a failure of the AIMD to a user and/or a health care provider if the osmotic pressure or the electrical conductivity is not within ±15% with the expected osmotic pressure or the expected electrical conductivity.

In an embodiment, the data may be a displacement of a compressible piston of the AIMD. In an embodiment, data may include one or more sensors external to the AIMD. In an embodiment, one or more one or more sensors external to the AIMD comprises a biosensor present on the body of the user. In an embodiment, one or more biosensors are remotely connected to the AIMD. In an embodiment, one or more biosensors are configured to collect data on the physiological condition of the body of a mammal having AIMD implanted within.

In an embodiment, the method may further include adjusting dosing of a drug discharge from the AIMD according to data collected from one or more biosensors, and/or one or more sensors.

In an embodiment, the expected osmotic pressure data is measured according to Equation (II):

$$\left(\frac{1}{\pi_2} - \frac{1}{\pi_1}\right)E = \frac{A(L_2 - L_1)}{MiRT} \qquad \text{Equation (II)}$$

or the expected electrical conductivity data is measured according to Equation (III):

$$\left(\frac{K}{\sigma_2} - \frac{K}{\sigma_1}\right) = \frac{A(L_2 - L_1)}{MiRT} \qquad \text{Equation (III)}$$

wherein M is a mass of a solute present in an osmotic chamber of the implantable AIMD, i is van't Hoff index, A is the cross sectional area of the AIMD wherein the piston is in contact with the drug chamber, and L1 and L2 are first and second positions of a back end plate of the compressible piston before and after displacement of the back end plate of the compressible piston under osmotic pressure $\pi_1$ and $\pi_2$, respectively, or with electrical conductivity of $\sigma_1$ and $\sigma_2$, respectively, T is average temperature of the AIMD in kelvin, and R is ideal gas constant.

In an embodiment, the AIMD may have wireless communication to inform the user about the failure of the AIMD. In an embodiment, wherein one or more sensors comprise a pressure sensor and/or a temperature sensor.

In an aspect an active implantable medical device (AIMD) is described. The device comprises an osmotic chamber comprising an osmotic agent or being provided to receive the osmotic agent; a permeability module to allow ingress of a fluid into the osmotic chamber; a drug chamber comprising a drug or being provided to receive the drug; a compressible piston located between the osmotic chamber and the drug chamber and comprising a cross sectional area, a drug chamber-facing surface and an osmotic chamber-facing surface; and a valve module comprising a valve to allow flow of the drug from the drug chamber to outside the AIMD through one or more drug outlets present in the AIMD; wherein the AIMD has dimensions that allow the AIMD to be implanted subcutaneously in a mammal, wherein the compressible piston is configured to move longitudinally as a whole within the AIMD during operation of the AIMD, and wherein the AIMD is configured such that the drug chamber-facing surface moves towards the drug chamber when the valve is opened and the osmotic chamber-facing surface subsequently moves towards the drug chamber-facing surface when the valve is closed, thereby causing the compressible piston to move longitudinally as a whole within the AIMD.

In an embodiment, a volume of discharge of the drug is equal to a change in volume of the compressible piston. In an embodiment, the permeability module comprises a forward osmosis semi-permeable membrane. In an embodiment, two or more modules of the AIMD form a communication network with each other. In an embodiment, the compressible piston is configured to move longitudinally as a whole within the AIMD to produce repeated flow of the drug from the drug chamber. In an embodiment, the compressible piston comprises a restrictor and/or a limiter. In an embodiment, wherein the limiter is configured to stop uncompressing or expanding the compressible piston beyond a first predetermined distance, and the restrictor is configured to stop the compressible piston from compressing beyond a second predetermined distance. In an embodiment, a successive dose-to-dose drug variation is ±25% or less by volume. In an embodiment, the compressible piston is an object configured to change volume by a given volume when the object changes shape from a compressed configuration to an uncompressed configuration. In an embodiment, the valve module comprises a motor. In an embodiment, the electronic module comprises a processor.

An embodiment relates to a system comprising the AIMD and an external sensor. In another embodiment, the system comprises an anomaly detection module. In yet another embodiment, the system further comprises an artificial intelligence (AI) module. In yet another embodiment, the system further comprises a dosing module. In yet another embodiment, the system further comprises a patient state detection module.

In an aspect disclosure relates to a system, comprising: an active implantable medical (AIMD) comprising one or more sensors configured to provide plurality of inputs collected during real-time operation of the AIMD, an external sensor placed outside the AIMD configured to provide a physiological parameter of a user having the AIMD, an artificial intelligence (AI) system configured to receive and analyze the inputs and the physiological parameter to predict a body response of the user using the AIMD; and a smart alert system, the smart alert system in communication with the AIMD and the external sensor configured to proactively send out a signal for help based on a predicted body response by the AI system.

In an embodiment, the AI system and the AIMD are in wireless communication with one another. In an embodiment, the AI system is configured to store monitored inputs from the AIMD and/or the physiological parameter of the user. In an embodiment, the AI system implements one or more of predictive learning, machine learning, automated planning and scheduling, machine perception, computer vision and affective computing to predict the body response of the user.

In an embodiment, the AI system configured to access the medication schedule and to send a signal to administer medicine based on the medication schedule to the AIMD. In an embodiment, the system is configured to update the machine learning model based on a physical parameter of the AIMD and a generated physiological condition of the user on a real time basis. In an embodiment, the system is configured to adjust a drug dosing schedule based on a predicted outcome of AI.

In an embodiment, the AI is configured to predict a future working condition of the AIMD and notify the user or a healthcare provider, if the future working condition of the AIMD is not within ±15% value of the corresponding expected value of the AIMD. In an embodiment, a future working condition includes a displacement of a compressible piston and/or osmotic pressure of the AIMD.

In another aspect, a system is described. The system comprises (1) Active wearable medical device (AWMD) (2) a fluid chamber, and (3) a channel. The AWMD comprises a drug chamber, a motor chamber, a piston, an electronic module and a permeability module. The drug chamber comprises a drug. The motor chamber comprises a housing, a motor, and a driving component. The piston is affixed to a first end of the driving component. The electronic module actuates the motor to operate the driving component and move the piston longitudinally to discharge the drug outside the AWMD through one or more orifices. The permeability module allows passive ingress flow of a fluid to an osmotic chamber from a fluid chamber through a semipermeable membrane upon activation of the fluid chamber and generates osmotic pressure to drive the piston longitudinally towards the one or more orifices in addition to actuation of the piston by the motor. The fluid chamber contains the fluid. The channel is fluidically coupled to a drug outlet wherein the channel discharges and deliver the drug. According to an embodiment, the AWMD is not implanted in a body of a mammal and is fluidically coupled to the fluid chamber via the semipermeable membrane.

In an embodiment, the fluid chamber is an expandable elastomeric bladder that expands and gradually releases the fluid across the semipermeable membrane to generate the osmotic pressure when a pressure is applied to the expandable elastomeric bladder.

In another embodiment, the fluid chamber is a rigid reservoir that enables diffusion of the fluid across the semipermeable membrane to dissolve an osmotic agent in the osmotic chamber and generate an osmotic gradient to drive the piston.

In another embodiment, the fluid chamber is a Hydrogel reservoir.

In another embodiment, the Hydrogel reservoir comprises a hydrogel that releases the fluid over time to enable the passive ingress flow of the fluid to the osmotic chamber from the Hydrogel reservoir.

In another embodiment, the fluid chamber is a microfluidic reservoir.

In another embodiment, the microfluidic reservoir is integrated with a flow restrictor interfaced with the semipermeable membrane to deliver the fluid to the osmotic chamber at a controlled rate.

In another embodiment, the fluid chamber is an active operated chamber.

In another embodiment, the fluid chamber is a passive operated chamber.

In another embodiment, the channel comprises a catheter configured to deliver the drug to a specific anatomical site.

In another embodiment, the catheter is configured for targeted administration of the drug.

In another embodiment, the system comprises an attachment component having perforations adapted to secure the system to skin and to ensure stable contact with the skin during the discharge of the drug.

In another embodiment, the channel comprises a biocompatible material.

In another embodiment, the drug chamber comprises a plurality of drug chambers.

In another embodiment, the system is configured to switch between the plurality of drug chambers for sequential discharge of the drug or combination of discharge of the drug.

In another embodiment, the channel comprises a dissolvable material that naturally dissolves in the body over a period of time.

In another embodiment, the system comprises a real-time imaging and navigation guidance device.

In another embodiment, the real-time imaging and navigation guidance device is configured to aid placement of the catheter and monitor dispersion of the drug in real-time.

In another embodiment, the attachment component comprises an adhesive layer.

In another embodiment, the attachment component comprises one of a mechanical fastener, a wearable strap, a wearable band, and a skin micro-anchor.

In another aspect, a system is described. The system comprises 1) a AWMD comprising an osmotic chamber comprising an osmotic agent or being provided to receive the osmotic agent; a permeability module to allow ingress of a fluid into the osmotic chamber; a drug chamber comprising a drug; a compressible piston located between the osmotic chamber and the drug chamber and comprising a cross sectional area, a drug chamber-facing surface and an osmotic chamber-facing surface; and a valve module comprising a valve to allow flow of the drug from the drug chamber to outside the AWMD through one or more drug outlets present in the AWMD; wherein the compressible piston is configured to move longitudinally as a whole within the AWMD during operation of the AWMD, and wherein the AWMD is configured such that the drug chamber-facing surface moves towards the drug chamber when the valve is opened and the osmotic chamber-facing surface subsequently moves towards the drug chamber-facing surface when the valve is closed, thereby causing the compressible piston to move longitudinally as a whole within the AWMD; (2) a fluid chamber that contains the fluid; and (3) a channel that is fluidically coupled to the one or more drug outlets drug outlets wherein the channel discharges and deliver the drug; wherein the AWMD is not implanted in a body of a mammal and is fluidically coupled to the fluid chamber via the semipermeable membrane.

In another embodiment, the fluid chamber is an expandable elastomeric bladder that expands and gradually releases the fluid across the semipermeable membrane to generate the osmotic pressure when a pressure is applied to the expandable elastomeric bladder.

In yet another embodiment, the fluid chamber is a rigid reservoir that enables diffusion of the fluid across the semipermeable membrane to dissolve an osmotic agent in the osmotic chamber and generate an osmotic gradient to drive the piston.

In yet another embodiment, the fluid chamber is a Hydrogel reservoir.

In yet another embodiment, the Hydrogel reservoir comprises a hydrogel that releases the fluid over time to enable the passive ingress flow of the fluid to the osmotic chamber from the Hydrogel reservoir.

In yet another embodiment, the fluid chamber is a microfluidic reservoir.

In yet another embodiment, the microfluidic reservoir is integrated with a flow restrictor interfaced with the semipermeable membrane to deliver the fluid to the osmotic chamber at a controlled rate.

In yet another embodiment, the fluid chamber is an active operated chamber.

In yet another embodiment, the fluid chamber is a passive operated chamber.

In yet another embodiment, the channel comprises a catheter configured to deliver the drug to a specific anatomical site.

In yet another embodiment, the catheter is configured for targeted administration of the drug.

In yet another embodiment, the system comprises an attachment component having perforations adapted to secure the system to skin and to ensure stable contact with the skin during the discharge of the drug.

In yet another embodiment, the channel comprises a biocompatible material.

In yet another embodiment, the drug chamber comprises a plurality of drug chambers.

In yet another embodiment, the system is configured to switch between the plurality of drug chambers for sequential discharge of the drug or combination of discharge of the drug.

In yet another embodiment, the channel comprises a dissolvable material that naturally dissolves in the body over a period of time.

In yet another embodiment, the system comprises a real-time imaging and navigation guidance device.

In yet another embodiment, the real-time imaging and navigation guidance device is configured to aid placement of the catheter and monitor dispersion of the drug in real-time.

In yet another embodiment, the attachment component comprises an adhesive layer.

In yet another embodiment, the attachment component comprises one of a mechanical fastener, a wearable strap, a wearable band, and a skin micro-anchor.

The methods and systems disclosed herein may be implemented by any means necessary for achieving various aspects to perform any of the operations disclosed herein. Other features will be apparent from the accompanying drawings and from the detailed description that follows.

BRIEF DESCRIPTION OF THE FIGURES

These and other aspects of the present disclosure will now be described in more detail, with reference to the appended drawings showing exemplary embodiments of the present disclosure, in which:

FIG. 15A and FIG. 15B illustrate an active wearable medical system incorporating a microfluidic reservoir as the fluid chamber, according to one or more embodiments.

FIG. 16 illustrates a drug delivery system configured for targeted drug administration through a catheter, according to one or more embodiments.

Figure 1:
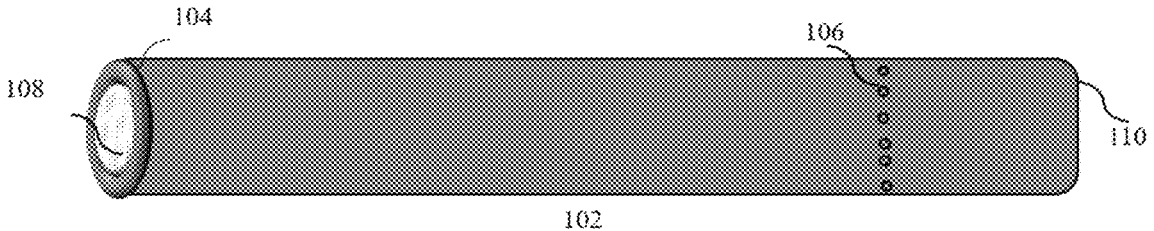
FIG. 1 shows an outside view of the implantable drug delivery device with a permeability module present at one end of said device.

Other features of the present embodiments will be apparent from the accompanying drawings and from the detailed description that follows.

DETAILED DESCRIPTION

One aspect of the present disclosure relates to an implantable device. The implantable device may be active implantable medical device (AIMD). The term "active implantable medical device" or "AIMD" refers to a medical device that is configured to be implanted within a mammal, i.e., an animal or a human, and the medical device is an electrically powered device. In an aspect, the implantable device is an electrically powered device. Implantable device and AMID are interchangeably used throughout the disclosure.

The implantable device of the present disclosure is implantable in mammals such as humans. Implantable devices could be implanted within the body of a user either surgically or via injection. In an embodiment, the implantable device of present disclosure is subcutaneously implanted within the body of the user, preferably in a human body. In the subcutaneous implant, the device is delivered under the skin into the subcutaneous tissue by surgery or injection and is used to deliver a drug for a long period of time. In some cases, the implantable device may be implanted transvenous.

In an aspect, the implantable device of the present disclosure provides a device for controlled delivery of drugs. "Drug" in context of the present disclosure may include any therapeutic active agent and/or a biologically active agent (i.e., an active ingredient in a pharmaceutical composition that is biologically active, such as a vaccine). Drug, that could be herein, is not limited by molecular weight of such agents. Terms "drug", "active agent", "therapeutic agent", "beneficial agent" or "pharmaceutical fluid" are used interchangeably. Drug as used herein refers to a single drug or multiple types of drugs. In some embodiments, the drug is one of injectable drugs such as, without limitation, Adalimumab, dulaglutide, enosumab, ustekinumab, pneumococcal 13-valent vaccine, romiplostim, paliperidone palmitate, erenumab, benralizumab, ixekizumab, ofatumumab, pegfilgrastim, guselkumab, golimumab, asfotase alfa, and blinatumomab. In some embodiments, the drug is a repurposed drug such as without limitation includes apixaban, lenalidomide, semaglutide, rivaroxaban, dapagliflozin, pomalidomide, fingolimod, ozanimod, tofacitinib, ambrisentan, axitinib, lenvatinib, and cariprazine.

One aspect of the present disclosure relates to an active implantable medical device (AIMD). The AIMD comprises a permeability module to allow ingress of a fluid into an osmotic chamber of the AIMD and a compressible piston, a drug chamber comprising a drug and a valve module to allow flow of the drug from the drug chamber to outside the AIMD through one or more drug outlets present in the AIMD. AIMD may have other parts or features also.

The implantable device of the present disclosure has a casing. The casing is the outermost portion of the implantable device that defines a section of the exterior shape or contour of the implantable device. The casing may have a tubular shape providing the device overall with a tubular structure. Tubular does not require to be a straight tubular; it may have some bends as per the application of the device.

One or more different modules of the device as discussed later in the disclosure providing a drug delivery mechanism is enclosed fully or partially within the casing.

One or more modules of the implantable device are preferably movable relative to the casing and/or relative to one another during operation of the device and/or during drug delivery operation.

During the drug delivery operation, a size or dose of drug is released from the device. In some embodiment, the dose of the drug released from the device is approximately kept the same in the sequential doses.

In an embodiment, a drug release via the device is ±25% or less of an intended target dose, preferably ±20% or less an intended target dose, preferably 15% of an intended target dose, furthermore ±10% or less an intended target dose, or ±5% or less an intended target dose. The dose-to-dose variation or flow discharge accuracy (used interchangeably throughout the specification). In an embodiment, a drug release variation in a sequential dose-to-dose release is ±25% or less of the volume, preferably ±20% or less of the volume, more preferably ±15% of the volume, furthermore ±10% or less of the volume, or ±5% or less of the volume.

In one aspect, an implantable drug delivery device has different modules such as without limitation, a permeability module, a sensor module, a drug module, a valve module, an electronics module, and/or a power module. These modules are interconnected with each other. It is possible that these modules talk to each-other like a network. The network structure allows precise drug delivery from the device. A person skilled in the art would understand different ways of interconnecting these modules, such as but not limited to screwing them together, creating notches at the ends of the modules, etc. In some embodiments, each module is threaded with male-female threads such that the first module screws into the second module, the second module screws into the third module, and the third module screws into the fourth module. In some embodiments, modules such as a sensor and permeability unit are adhesively bonded on a wall of the device, and/or casing of the device.

One aspect of the present disclosure relates to a device that is an active implantable medical device (AIMD) comprising a permeability module comprising a semipermeable membrane at one end of the device, an osmotic chamber comprising an osmotic solution (or osmotic agent), a sensor module comprising one or more sensors, a drug chamber comprising a drug, a compressible piston, wherein the compressible piston is sandwiched between the osmotic chamber and the drug chamber, a valve module to allow unidirectional flow of the drug from the drug chamber to outside the device through one or more drug outlets orifices present within the device, an electronic module, and a power supply module. Sandwiched herein signifies that the compressible piston is in between with the drug chamber at one side and the osmotic chamber at another side. It should not be construed that the compressible piston in all embodiments of the disclosure has to be in direct contact with the drug chamber and the osmotic chamber. It is possible that other membranes or layers are present in between them as per need of the device.

FIG. 1 shows an outside view of the implantable device. The device has a tubular structure. It has a first end 108, and a second end 110. The components and parts of the device are shown in more detail in FIGS. 2 to 7. As shown in FIG. 1, the device comprises an outer casing 102, a permeability module 104 at the first end and one or more drug outlets/orifices 106 for release of the drug.

The casing 102 is generally a tubular element. The thickness of the casing could be decided on various factors such as material of the casing, components of the device and the purpose of the device. However, it would be desired that the casing is kept thin so that bulkiness of the device is minimized. The thickness of the casing could be about 0.25 mm, 0.3 mm, 0.4 mm, 0.5 mm, 0.6 mm, 0.7 mm, 0.8 mm, 0.1 mm.

Casing protects the internal mechanism of the device from any undesired reactions. Casing may have some openings/holes to allow discharge of drug outside the device into the body of the user of the implantable device. These openings allow only unidirectional flow of the drug, whereas the fluid from the body of the user cannot enter inside the device through the openings. A person skilled in the art could recognize different means to achieve the said objective, not limited to one-way valve system.

The casing surrounds the device except the first end 108 having the permeability module 104. Dimensions of the device are such that sub-cutaneous implantation of the device in a mammal or more specifically a human could be achieved. In an embodiment, the breadth of the casing is between 3 mm to 5 mm, such as 3 mm, 3.5 mm, 4 mm, 4.5 mm etc. In an embodiment, the length of the casing is between 2.5 cm to 10 cm, such as 4 cm, 5 cm, 6 cm, 7 cm, 8 cm, 9 cm or 10 cm or preferably 4 cm to 8 cm.

In an embodiment, the casing 102 is made up of a biocompatible material or FDA approved material, such as Titanium without limitation. The material selected for the casing should have durability, corrosion resistance, and compatibility with body and body fluids.

In an embodiment, the casing of the implantable device may further comprise a coating of a nonconductive ceramic, a nonconductive polymer or an epoxy resin. In an embodiment, the outer surface of the casing could have different devices such as but not limited to biosensors (not shown in FIG. 1). These sensors may be in contact with body fluid and help to know the physiological parameter of the body fluids, such as temperature, a bioactive agent etc.

The permeability module 104 along with other functions, primarily seals the interior of the implantable device from the first end 108, allowing only specific liquid molecules to permeate through a membrane plug into the device's interior. In an embodiment, the permeability module 104 also effectively prevents items within the implantable device, such as an osmotic agent to backflow outside the device.

Figure 3A:
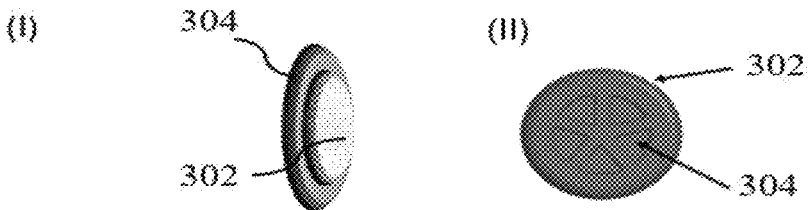
FIG. 3A shows a schematic of a flat membrane as a permeability module according to one or more embodiments.
Figure 3B:
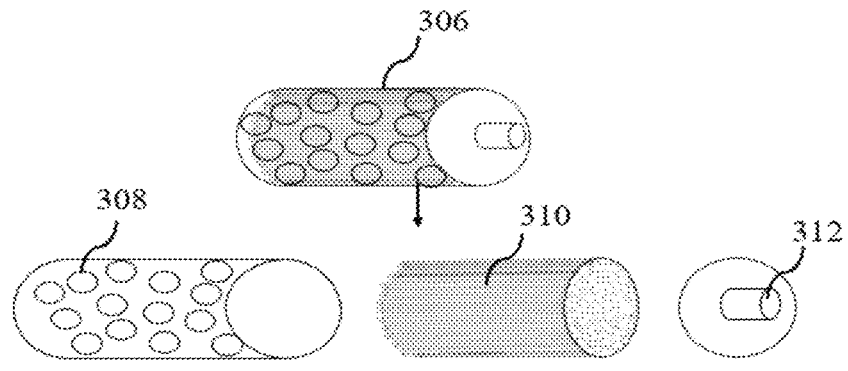
FIG. 3B shows a schematic of hollow fiber membrane as a permeability module according to one or more embodiments.

The permeability module 104 at the first end allows the fluid to ingress into the device and is coupled to the osmotic chamber. The permeability module is designed to separate solutes from a feed solution, such as blood serum, using a semipermeable membrane. Details of permeability module are shown in FIG. 3A and FIG. 3B. The permeability module is configured for a forward osmosis.

The permeability module is in fluid communication with the osmotic chamber. The osmotic chamber is adapted to include an initial chemical composition (e.g. one or more ion species) that functions to alter osmotic pressure within the osmotic chamber upon fluid (such as water from the body fluid) migration across the permeability module.

In an embodiment of the disclosure, the osmotic chamber is filled with an osmotic agent. In some cases, the osmotic agent could be a swelling agent that expands upon contact with water. This swelling results from the swelling agent's contact with water then produces a force which drives the solute fluid from the solute reservoir into an osmotic compartment of the apparatus. A wide variety of swelling agents can be used. The swelling agent typically consists of one or more swellable hydrophilic polymers. Suitable swellable hydrophilic polymers include cellulose derivatives such as hydroxy C1-4 alkyl celluloses, hydroxy C1-4 alkyl C1-4 alkyl celluloses, carboxyalkyl celluloses and the like; vinyl pyrrolidone polymers such as crosslinked polyvinylpyrrolidone or crospovidone; copolymers of vinyl pyrrolidone and vinyl acetate; gums of plant animal, mineral or synthetic origin such as agar, alginates, carrageenan, furcellaran derived from marine plants, guar gum, gum arabic, gum tragacanth, karaya gum, locust bean gum, pectin derived from terrestrial plants, microbial polysaccharides such as dextran, gellan gum, rhamsan gum, welan gum, xanthan gum, and synthetic or semi-synthetic gums such as propylene glycol alginate, hydroxypropyl guar and modified starches like sodium starch glycolate. The swellable hydrophilic polymers are present in suitable amounts such that the polymeric swelling agent exhibits controlled swelling and the desired rate of drug delivery is obtained and the polymeric swelling agent does not contribute significantly to increasing the size of the osmotic system. The polymeric swelling agent can comprise one or more of the above swellable hydrophilic polymers. Often, a mixture of two hydrophilic polymers provides the desired controlled swelling. Illustrative cellulose derivatives that may be used as swellable hydrophilic polymers in the polymeric swelling agent of the present invention include hydroxy C1-4 alkyl celluloses such as hydroxymethyl cellulose, hydroxyethyl cellulose, hydroxypropyl cellulose and the like. For example, the polymeric swelling agent may be a mixture of two different types or two different grades of the hydroxy C1-4 alkyl celluloses. In another embodiment of the present invention, copolymers of vinyl pyrrolidone and vinyl acetate, in admixture with alkylene oxide homopolymers such as polypropylene oxide, preferably ethylene oxide homopolymers or in admixture with hydroxy C1-4 alkyl celluloses, preferably hydroxyethyl cellulose, may be used as the polymeric swelling agent. A wide variety of polyethylene polymers (e.g. polyethylene glycols) are commercially available.

In an embodiment, a barrier (not shown in Figures) may be covering the osmotic chamber to produce a sealed chamber. When drug delivery is desired, the sealed chamber is opened, the water ingress in the chamber developing an osmotic pressure.

Figure 5:
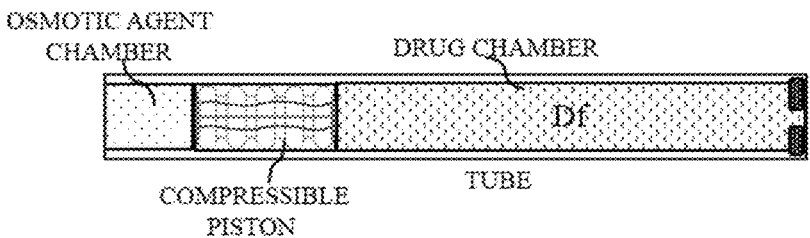
FIG. 5 shows a schematic of a drug module, according to one or more embodiments.

Osmotic chamber is a part of drug module as shown in FIG. 5. The drug module has an osmotic chamber, compressible piston and drug chamber having a drug, Df as shown in FIG. 5. One or more drug outlets 106 are present directly over or near the end of a drug chamber.

As shown in FIG. 3A, the permeability module comprises a membrane 302 that provides unidirectional permeability of fluid from body from outside to inside of the device. The membrane is preferably a semipermeable membrane (also referred to as a membrane plug). The semipermeable membrane refers to a differentially permeable membrane or selective permeable.

The semipermeable membrane could be either a cation-exchange membranes (CEMs), anion-exchange membranes (AEMs), alkali anion-exchange membranes (AAEMs) and proton-exchange membranes (PEMs). The semi-permeable could be non-ionic membrane. The membrane could be synthetic or biological membrane. The membrane 202 is typically stationary and coupled to an osmotic chamber.

The material selected for membrane will depend on the exact configuration and function of the implantable device. For example, the material selected for membrane is typically dictated by the ions passing through the membrane and the desired pumping rate of the implantable device. Typical materials for membranes include perfluorosulfonate membranes known in the art and available under the trade name NAFION. Additional resins are the copolymers of styrene and di-vinyl benzene having sulphonate ion as the charge group which has high selectivity sodium ions. Exemplary materials further include Neosepta type membranes, C/R, CMB, CMB-2, C66-F, and CCG-F, AM-1, AM-3 AFN and AM-X from Ameridia CM-1, CM-2, CMB, and others, commercially available from AMERIDIA, CMI 7000, Membranes International and PC-200D from PCA GmBH; ome typical resins include copolymers of styrene and di-vinyl benzene having sulfonate ion as the charge group, which have a high selectivity for sodium ions. Such commercial cationic membranes, e.g., Nafion type membranes, are available from Dupont.

The membrane is a substantially flat membrane. Substantially flat signify that the membrane when viewed from a naked eye over a flat surface seems flat.

The membrane 302 as shown in FIG. 3A could be supported by a plate or a support structure 304. However, in some cases, if the membrane 302 has enough strength of its own to remain stationary without the support, then plate 304 may not be necessary in the permeability module. Plate 304 should be either a porous separator that is at least permeable to $H_2O$ and NaCl molecules and enables water and ions from an external source e.g., an inside of a living being's body, to migrate into the device. In some cases, plate 304 could have holes to allow fluid inflow inside the device. In an embodiment, the support structure or plate 304 could be made of biocompatible material and/or metal such as without limitation glass, porous protective gel, natural and synthetic plastics and composites, metals such as titanium, FDA approved material such as stainless steel. A plate includes one or more plates arranged in the series.

In some embodiments, the membrane 102 (semipermeable membrane) is sandwiched between two plates such as a front plate and a back plate (not shown in figure). Sandwiched herein signifies two plates are on either side of the membranes, however other materials could be present between plate and the membrane, if needed. In an embodiment, front plate and back plate may have a plurality of holes (not shown in FIG. 3A). Alignment of plurality of holes in the front plate and the back plate could help in adjustment of ingress fluid inside the device. For example: if all holes of the front plate and back plate are aligned together, then the flow of the fluid will be maximum, and if none of the holes are aligned then flow of the fluid into the device is completely stopped. This intermediate configuration allows fine tuning of the ingress rate. This adjustment could be adjusted prior to operation of the device. In an embodiment, a device having a sensor to monitor the ingress of the fluid and motor to rotate the plates may perform similar tasks inside the body of the user.

In an embodiment, the permeability module may have hollow fiber or bundles of hollow fibers arranged together, forming a bridge for entry of fluid into the device as shown in FIG. 3B. In FIG. 3B, the permeability module has an exterior surface 306 with plurality of holes 308. The exterior surface 306 is holding one or more bundles of hollow a hollow fiber 310. One or more hollow fibers are made of a semipermeable membrane and have a hollow core, allowing water to flow through. Both ends of the fibers, on the right side and the left side of the casing are U shaped.

In an embodiment, the hollow fibers contain a solute solution such as but not limited to glucose solution (G) as shown in FIG. 3B. The high concentration of the glucose solution allows natural osmosis to happen within the device. Briefly, osmosis is the diffusion of a liquid (most often assumed to be water, but it can be any liquid solvent) through a semipermeable membrane from a region of high chemical potential to a region of low chemical potential. The selectively permeable membrane must be permeable to the solvent, but not to the solute, resulting in a pressure gradient across the membrane. The force per unit area required to prevent the passage of solvent through a selectively permeable membrane and into a solution of greater concentration is equivalent to the turgor pressure. Osmosis can be controlled or modulated in a number of ways, e.g. by increasing the pressure in the section of high solute concentration with respect to that in the low solute concentration.

In an embodiment, concentration of an osmotic agent could vary from 0 to 10 millimolar to 20 millimolar to 50 millimolar to 100 millimolar to 150 millimolar to 200 millimolar.

In some embodiments, the hollow fibers contain solutes such as but not limited to NaCl.

The hollow fiber membrane is a forward osmosis membrane and comprises an inlet end facing the first end of the device towards the first end and an outlet facing internal of the device. These membranes utilize the natural osmosis process, where water moves from a low concentration to a high concentration through the membrane. Natural osmosis requires lower energy compared to traditional reverse osmosis systems that operate under lower pressure conditions, within hollow fibers.

Figure 2:
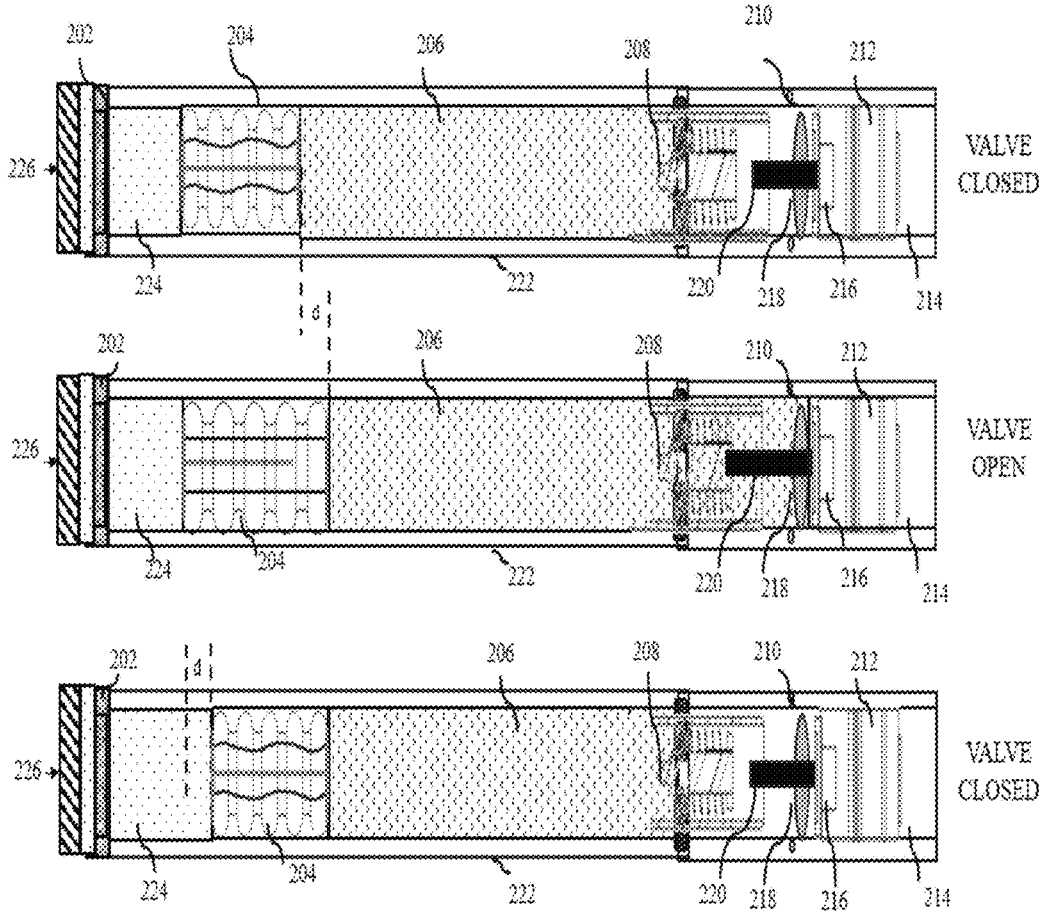
FIG. 2 shows an inside view of the implantable drug delivery device in a valve open and closed state, according to one or more embodiments of the disclosed invention.

During operation of the device to release the drug outside the device, the orifices open. Details on operation of the device are shown in FIG. 2.

Figure 4:
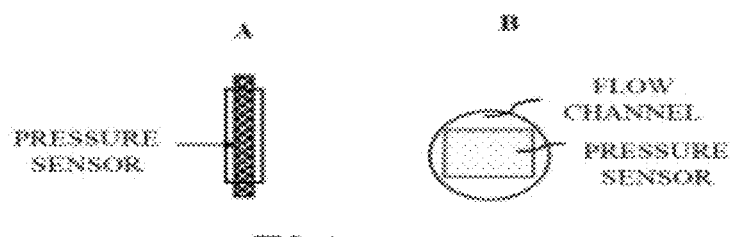
FIG. 4 shows a schematic view of the sensor module. (A) shows front view of the sensor module and (B) cross sectional view of the sensor module taken from the permeability side of the device.

In an embodiment, the implantable device has a sensor module along with other modules, parts and features as described in different embodiments of this disclosure. An example of a sensor module is shown in FIG. 4. A sensor module without limitation includes at least one sensor.

The term "sensor" relates to a device, module, machine, or subsystem whose purpose is to detect events or changes in its environment and send the information to other electronics, frequently a computer processor. A sensor is always used with other electronics. Sensor is an umbrella term that encompasses both biosensor and non-biosensor. In an embodiment, sensor refers explicitly to non-biosensor.

The term "biosensor" relates to an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts, binds with, or recognizes the analyte under study. The biosensor may include without limitation pulse oximeter, heart rate sensor, ECG sensor, skin sensor(s), body temperature sensor, blood pressure sensor, impedance sensor etc. According to one embodiment, all types of biosensors come under the scope of the present invention. The biosensor helps in detecting physiological parameters of the body.

A sensor could be selected from a pressure sensor, a temperature sensor, a conductivity sensor, etc. In some embodiments, the sensor module includes a conductivity sensor such as an electrical conductivity sensor. A person skilled in art would recognize various modes of attaching these sensors within the principle of operation of the device. In an embodiment, sensors may be embedded and/or attached to a supporting structure such as additional disc or protrusion or pockets made in the casing and/or inside the device to hold the sensors. A pressure sensor measures osmotic pressure inside an osmotic chamber. A temperature sensor measures internal temperature of the device and/or temperature of drug. In an embodiment, the temperature sensor may measure the temperature of surrounding areas of a device. In some embodiments, the conductivity sensor is configured for monitoring osmotic agent conductance.

In an embodiment, an output from these sensors is utilized to provide real-time feedback to a processor. Real-time feedback allows precise delivery of drugs by responding to variations in conductivity level, osmotic pressure, etc., thereby aligning dose discharge as per the patient's need by operating the valves of the device that regulates flow of drug discharge.

In an embodiment, the osmotic agent represents a wide range of salinity levels, and the sensor must accurately measure conductivity under these conditions.

In some embodiments, the conductivity sensor has a conductivity range from 0 μS/cm (low conductivity) to 10 mS/cm to 20 mS/cm to 50 mS/cm to 100 mS/cm to 150 mS/cm to 200 mS/cm (high conductivity). In some embodiments, the sensors function reliably within temperature range of 25° C. to 40° C. In some embodiments, the sensors function reliably within the body temperature (ex: 37° C. for human) of the host in which the device is implanted. This ensures its stability and accuracy across varying environmental conditions.

In some embodiments, the conductivity sensor comprises an integrated Resistance Temperature Detector (RTD) sensor (for example, Pt1000). The Pt1000 sensor has a base resistance value of 1000 ohms at 0° C. It is suitable for 2-wire circuit configurations, has less significant impact of lead wire resistance, consumes less power due to high resistance, and is typically available only with thin-film element constructions. Temperature often influences result of a conductivity sensor. Therefore, it is possible that the conductivity sensor has a temperature compensation mechanism to ensure accuracy in the changing environment.

In some embodiments, a sensor is designed to fit snugly inside a cylindrical space within tube and/or casing with specific dimensions (for example: within 5 mm×4 mm). This compact design allows for easy integration into various applications. In some embodiments, a sensor's housing material is titanium, which provides durability, corrosion resistance, and compatibility with the fluid.

Sensors should not undergo chemical reactions that could alter its performance or degrade its materials. In an embodiment, sensors are made up of noble metals such as without limitation Pt (platinum), silver (Ag) based electrodes prevent hydrolysis. These electrodes ensure stable performance even in the presence of water. In some embodiments, the sensor uses 0.3-1 VP-P (peak-to-peak voltage) for operation. In some embodiments, the sensor uses 0.7 VP-P-1 VP-P (peak-to-peak voltage) for optimal operation. In some embodiments, the sensor allows for simulating the cell constant, which relates to its geometry and electrical properties.

In an embodiment, the implantable device has a drug module along with other modules, features and parts. An example of a drug module is shown in FIG. 5. Referring to FIG. 5, a drug module includes a drug chamber. Drug chamber contains drug Df. The drug chamber is surrounded by casing from up and down, a compressible piston at one end. The distal end of the drug chamber opposite to the compressible piston has valves that control discharge of the drug Df. The drug chamber in general has a tubular structure. However, as per the requirement of the implantable device small changes are allowed such as it may have some protrusions or pockets to hold a device such as sensor etc. In an embodiment, the drug chamber has width between 2 mm to 5 mm, such as 2.5 mm, 3 mm, 3.5 mm, 4 mm, 4.5 mm etc. In an embodiment, a drug module (combination of osmotic chamber+compressible piston+drug chamber) may be about 2 to 6 cm in length, such as 2 cm, 3 cm, 4 cm, 5 cm, 6 cm. The drug Df without limitation could be any known drug or its conjugated form, or chelated form, etc., or within a vehicle such as beads, or in forms such as without limitation microparticles, liquid, etc., understood by a person skilled in the art within contemplated disclosure.

In an embodiment, the compressible piston is configured to eject a volume of the drug within a time that is shorter compared to the time it takes volume of one dose of fluid flowing through permeability membrane. In an embodiment, ejecting a drug dose happens within few seconds. This way, the power required to open and shut the relief valve is low as compared to the power needed to push the compressible piston.

A compressible piston may be designed in many ways. Some designs of the compressible piston are shown in FIG. 5A to 5G. The compressible piston is an object that changes a volume of the object by a given volume when the object changes shape from a compressed configuration to an uncompressed configuration.

In an embodiment, a compressible piston has a compressible object and a dual stopper such as a limiter and a restrictor. A restrictor prevents the over compressing the piston. Maximum amount of compression is allowed till the compression object has travelled a distance, 'd'. Limiter prevents the compressible piston from exceeding the stroke 'D' in the uncompressed state. In an embodiment, the compressible piston may have more than one dual stopper mechanism. For example: every small distance of the compressible has a separate dual stopper mechanism, that is capable of functioning independent of its own as well in combination with other dual stoppers.

In an embodiment, the compressible piston has two end caps, (front end cap towards the drug dispensing side; and back end cap towards permeability module side). The end caps are movable. The movement of end caps cause the whole compressible piston to move forward. When the valve is open, the front end cap moves. The back end cap remains stationary. When the valve is closed, the liquid starts coming from the permeable module and pushing the back end cap, e.g. towards the front end cap. The back end cap now moves and compresses the compressible object. Then again, when the valve is open, the front end cap moves. This happens sequentially, leading to a one-way (forward) crawling like movement of whole compressible piston. The compressible piston is configured to have a one-way crawling movement in the device towards the drug chamber. Since the piston forms a wall of the drug chamber, this process leads to a decrease of the volume of the drug chamber.

In crawling movement, the piston is compressed by osmotic pressure forming in the osmotic chamber such that the first surface of the piston is displaced relative to a body of the AIMD and relative to a second surface of the piston closer to the drug or the one or more drug outlets than the first surface. When the piston relaxes (to assume its uncompressed shape, e.g. when the valve is opened), the second surface is displaced relative to the body in order to decrease a volume of the drug chamber to discharge drug from the chamber through the one or more drug outlets)

In an embodiment, one or both stoppers (restrictor and limiter) are attached on the end caps. In an embodiment, the end caps have additional components on which one or both stoppers are attached. The plate could be a rigid plate The restrictor may be present in both front end and back end plates, or it may be present in either of the end plates. In some embodiments, the inside of the back end cap has the restrictor. This restrictor could be attached to the back end cap or a separate rigid plate. In some embodiments, the rigid plate is present on the inside of the front end cap can be an integral part of the front end cap or separate from the front end cap.

In an embodiment, both or at least one of the end plates provides enough rigidity to allow anchorage of limiter and/or restrictor along with other parts such as sensor, compressible object. In an embodiment, the end plates are either compressible, or non-compressible. In case the end plates are compressible, it is possible that end plates are made of different compressible material than that of compressible object of the compressible piston.

In an embodiment, the compressible piston of the present disclosure may be different from prior art pistons that only expand in the longitudinal direction during injection, and there is no piston that separates two chambers (drug chamber and osmotic chamber) and moves along a cylindrical tube.

In another embodiment, the ends caps provide a sealant property to stop any leakage of fluid within the compressible piston. In an embodiment, end caps are made of a material such as a rubber stopper of a syringe. In an embodiment, the end caps are hermetically sealed. In an embodiment, the caps sealing engage the tube may seal the drug chamber on one end and the osmotic chamber on another end, however, the caps on their own may not be hermetically sealed.

In an embodiment, the end caps provide liquid tight seal. The end caps provide hermetic sealing such that there is no transfer of liquid from the osmotic chamber to the drug chamber and vice versa. For example, in an embodiment, the end cap could have a wiper lip to make the end cap hermetically sealed.

In an embodiment, the compressible piston compresses and decompresses to produce a drug shot.

In an embodiment, the compressible piston separates an osmotic chamber and a drug chamber.

The compressible piston traverses along a longitudinal axis of a cylindrical tube of an implantable device.

In an embodiment, compressible piston comprises a first built-in stopper (limiter) that prevents the compressible piston from decompressing beyond length D, a second built-in stopper that prevents the compressible piston from compressing beyond length D-d (restrictor), wherein d is the stroke of the compressible piston, and one or more compressible objects, wherein the compressible objects include compressible materials. In some embodiments, the compressible object may comprise an elastically deformable structure wherein the deformation leads to change in volume both externally and internally. The elastically deformable structure may provide a force (e.g. an elastic restoring force) which still tends to increase the length of the piston to a maximum length of the limiter has length D. In other words when the piston has length D, the structure may still be elastically deformed and not fully relaxed. Limiter defines the length 'D'.

A compressible object refers to a substance or material that can reduce in volume or size under pressure. Here are some examples of compressible objects: natural materials such as gases that includes without limitation air, carbon dioxide ($CO_2$), helium and nitrogen; organic materials that include without limitation wool, cotton, cork, and feathers; biological tissues that include without limitation sponge (natural and synthetic), cartilage, cellular plant structures (e.g., moss); synthetic materials such as foams, polyurethane foam (memory foam), polystyrene foam (styrofoam), neoprene foam, open cell and closed cell foams; rubber and elastomers such as natural rubber, silicone rubber, EPDM (Ethylene Propylene Diene Monomer); plastic and polymers such as polyethylene (in certain configurations), polyvinyl chloride (PVC) foam sheets, thermoplastic elastomers; Gel-based Materials hydrogel, silicone gel, metals and Alloys; foamed metals such as aluminum foam, nickel foam; spring like or elastic metals such as steel springs, shape-memory alloys (e.g., Nitinol).

In an embodiment, the first stopper (limiter) could be a spring having a fixed uncompressed length such that the spring prevents the compressible piston from uncompressing beyond displacement length D.

It should be understood that the compressible pistons are enclosed within casing, though not shown in in FIG. 5A to 5G.

Figure 5A:
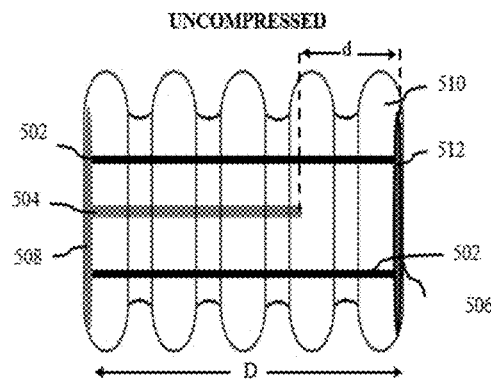
FIG. 5A shows an example of a compressible piston that can be used in the implantable device.
Figure 5A:
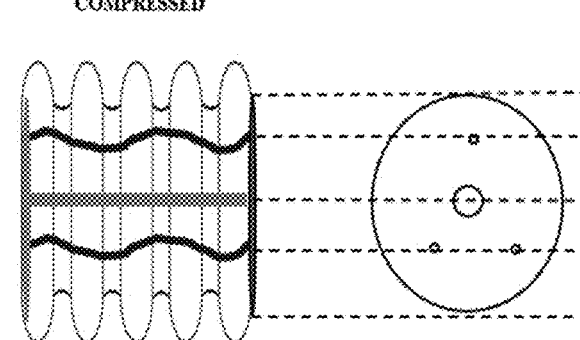

As shown in FIG. 5A, the compressible piston comprises a compressible object 510. In the said figure, the compressible object 510, is shown in bellow-like shape, however, any other geometric structure is possible. The compressible piston has two end plates 506 and 508. It has further had one or two rigid plates 512 (shown as disc shapes in the figure, though other geometric shapes are possible). In an embodiment, rigid plates are part of the end caps. The compressible object has a dual stopper system (limiter 502 and restrictor 504). As shown in FIG. 5A, both stoppers (restrictor and limiter) are connected to the back end cap 508 of the compressible piston. However, in some instances, the front end cap may have both the stoppers (limiter and restrictor, not shown in the figure). The first stopper (limiter, 502) is a string-like structure to control maximum expansion of the compressible piston. The back end cap 508 has a horizontal protruding structure that acts as a second stopper (restrictor, 504). In some cases, both end caps may have protruding structures. The protruding structure (rod-like structure as shown in figure) at the end cap controls the compressed state of the compressible piston from compressing further the distance travelled 'd'. The protruding structure stops the compressible piston in compressing more than the distance d' in the compressed state.

In an embodiment, a compressible object is made of a material that stops leakage of any fluid within the compressible piston module, such as a closed cell foam.

The compressed and uncompressed state of the compressible piston is shown on the right and left side of the figure. The dual built-in stopper results in precise drug delivery during each dosing cycle. Though the figure shows limiter like a string-like structure, other forms of controlling maximum movement of the compressible piston are possible.

Figure 5B:
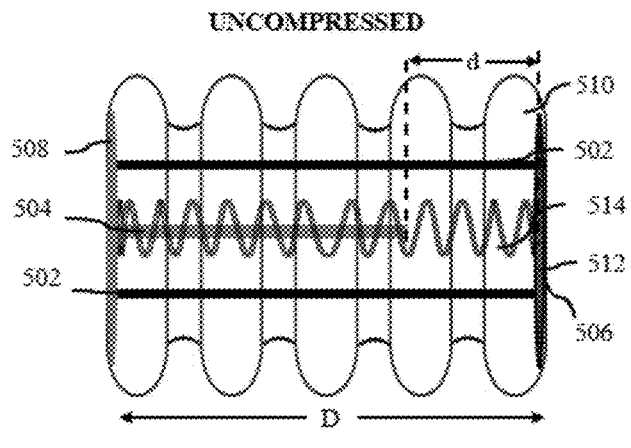
FIG. 5B shows an example of a compressible piston that can be used in the implantable device.
Figure 5B:
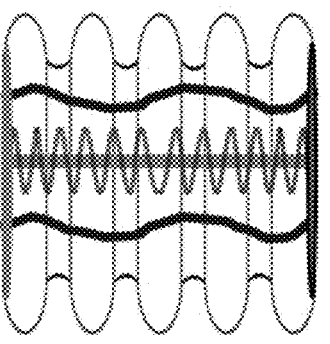

In FIG. 5B, there is an additional spring like material connected to the edges of the end cap. A spring could act as an additional compressible object, 514 (or as a substitute for the compressible object). In an embodiment, the spring acts as a first built-in stopper/limiter to stop the compressible piston going beyond distance 'D' when uncompressed.

In an embodiment, end caps could take any shape. It may be in the form of a plate or a disc, etc.

Figure 5C:
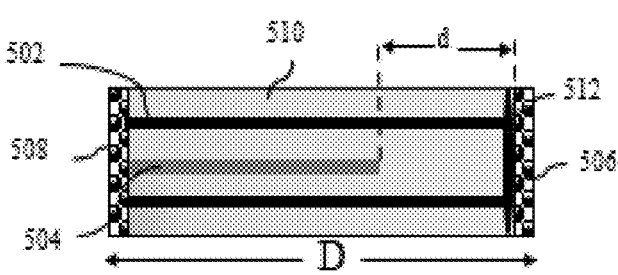
FIG. 5C shows an example of a compressible piston that can be used in the implantable device.
Figure 5C:
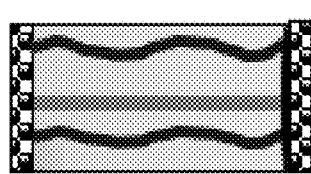
Figure 5D:
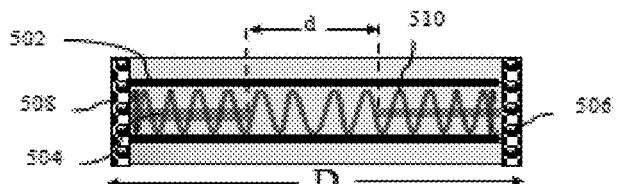
FIG. 5D shows an example of a compressible piston that can be used in the implantable device, according to one or more embodiments.
Figure 5D:
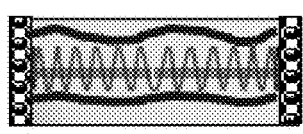

In FIG. 5C and FIG. 5D, the compressible object, 510 in its entirety, has flat structure. Though other geometrical shapes of the compressible object are possible. Further, the second stopper/restrictor constitutes one and two protruding structures (504) in FIGS. 5C and 5D respectively to stop the compressible piston to compress more than the distance 'd' in the compressed state. The protruding structures are designed in such a way that the protruding structure touches each other but do not override each other.

In an embodiment, the compressible object is made of a material that is elastic, biocompatible and providing seal to any leakage of water or fluid from the osmotic chamber into compressible piston. In an embodiment, the compressible piston is sealed with a material (e.g., sealant like material or foam like material) preventing any fluid leakage seeping within it.

Figure 5E:
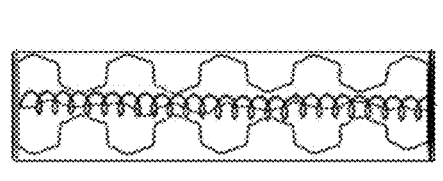
FIG. 5E shows an example of a compressible piston that can be used in the implantable device, according to one or more embodiments.

In FIG. 5E, compressible object 510 has string that acts as a limiter (502), stopping the uncompressed portion to expand to more than distance D. The two protruding structures 504 (which may protrude from the end cap(s)) act as restrictors. When the two protruding structures meet, further compression of the compressible piston is not possible. That means, the protruding structures work as a second built-in stopper. In the said figure, the spring acts as an additional compressible object, 512.

Figure 5F:
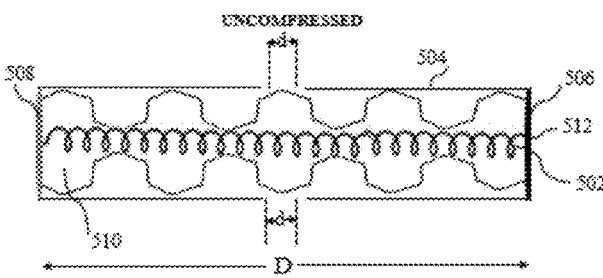
FIG. 5F shows an example of a compressible piston that can be used in the implantable device, according to one or more embodiments.
Figure 5F:
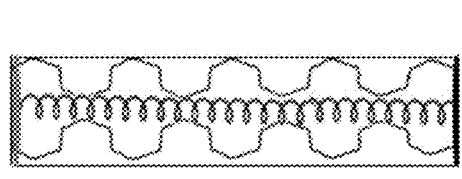

In FIG. 5F, spring acts as a limiter 502, stopping uncompressed portions from expanding beyond distance D. The restrictor is the protruding structures, 504.

Figure 5G:
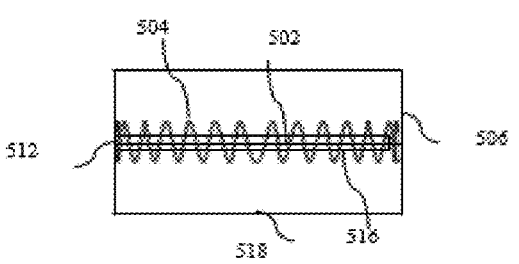
FIG. 5G shows an example of compressible Piston with flexible front plate that can be used in the implantable device, according to one or more embodiments.
Figure 5G:
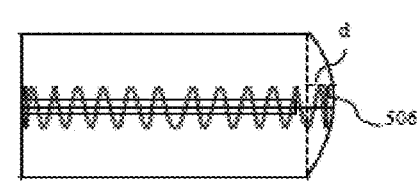

In FIG. 5G, the restrictor 504 is like a needle shaped anchored to the rigid plate 512. The thread type first stopper (limiter 502) is anchored to the back plate 508 and front plate 506 and traverses through the needle shaped restrictor 504. The spring shaped compressible object is wrapped around the needle shaped object. The space between the back plate and the front plate can be filled with closed cell non-porous foam. The perimeter of the front plate can be pinned at the perimeter of the front plate or could be free floating. If pinned, the perimeter could be pinned to a peripheral wall of the compressible piston. The length of the thread types first stopper of D. The length of the needle shaped second stopper is D-d, where d is the distance that the flexible front plate moves in the longitudinal direction of the compressible piston under the constraints of the first and second stoppers for each dose of the drug. The compressible piston assembly comprises a rigid outer cylindrical tube 518 featuring a rigid backplate and a flexible front plate. Enclosed within the outer tube is a smaller-diameter internal rigid tube. This internal rigid tube 516 houses a limiter and a restrictor, such as a string and a spring, with the string connecting the rigid backplate to the flexible front plate. When the spring is in a compressed state, the flexible front plate remains flat. However, as the spring decompresses, it exerts force on the flexible front plate, causing it to bulge outward. This bulging action results in an expansion of the piston by a distance d.

In an embodiment, the compressible piston is free of the rigid tube.

In an embodiment, a compressible piston has a front end cap that is configured to flex or flexes at the center but is pinned at the periphery. The back end cap is rigid. In this embodiment, each time the front end cap flexes from the compressed position to the uncompressed position, the internal volume of the compressible piston changes by a given volume, which is the dose size.

In an embodiment, as per requirement, a piston module may have one or multiple compressible piston structures.

In some embodiments, a piston movement optionally utilizes energy from energy/power sources present in the power module of the device.

In some embodiments, a space between the compressible object is filled with gas. In an embodiment, the energy required to compress the compressible object could be derived from Gibbs potential across a permeability membrane. When the valve opens, the compressed piston reverts to its uncompressed state. This mechanism creates a one-way crawling movement of the compressible piston in the drug chamber.

In an embodiment, the compressible piston position does not control the opening and closing of the relief valve, by decoupling shot size from the osmotic pressure and valve opening time while ensuring dosing accuracy.

In an embodiment, the compressible piston position controls the opening and closing of the relief valve. In such a case dose size is controlled mechanically without electrical power, and the dosing frequency is controlled by an electrical actuator. In such a case, a compressible piston may not be needed.

In some embodiments, a sensor measures and determines the position of the compressible piston. The position of the compressible piston is used to determine if the implantable device is functioning correctly. In case, pressure readings show that the pressure change is not consistent with the theoretical prediction for the compressible piston displacement, then the implantable device will send a signal to the patient and/or a caregiver about a possible defect in the implantable device. The device may have to be immediately removed. The drug in the drug chamber is pushed due to osmotic pressure exerted by the osmotic agent present in the osmotic chamber via the compressible piston. The compressible piston is operable to move a distance 'd' to deliver a constant volume of the drug Df for each shot via a valve module that functions as On-Off flow switch. The mechanism of the valve is explained in detail in FIG. 6A to 6B.

Figure 6A:
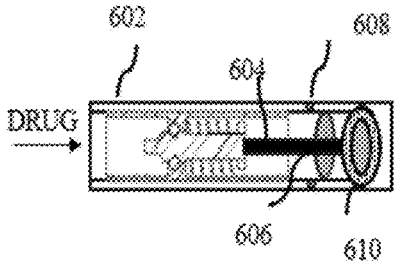
FIG. 6A shows a schematic of internal view of an on-off flow switch/valve module.

In an embodiment, the implantable device along with other features, parts and module has a valve module. An example of valve module is shown in FIG. 6A. In an embodiment, the implantable device may have a valve that is an active valve configured to be electronically controlled. In an embodiment, the device may have more than one valve, for example: one is an active valve and other passive valve, or both active valves. In some examples, the valve includes an active valve that is electronically activated by the electronic control module of the device. In some examples, the valve includes an active one-way valve that is electronically controlled module. In some examples, valve includes a set of two parallel active valves. In some examples, valve includes a set of series of active valves. In some examples, the passive one-way valve includes a duck-bill valve. In some examples, the passive one-way valve includes a movable valve component (e.g., ball, poppet, etc.) and a biasing member (e.g., a spring).

The electronic module configure controls the valve module such that the valve module is switchable between open and close states by in response to commands provided by the electronic module.

Referring to FIG. 6A, the valve module is enclosed within a casing 602, acts as an ON-OFF flow switch and comprises a spring loaded relief valve (like a bicycle tube valve) with a ball and a seat coupled to an actuator, 610 (e.g. stepper motor with helical shaft or vibratory motor, etc.) with a push rod 604, to push the head of the relief valve opening the seal 606, thereby creating a slight gap between the ball and the seat of the relief valve. The actuator is powered via electronics module and power module. Drug is released from drug outlet 608.

Figure 6B:
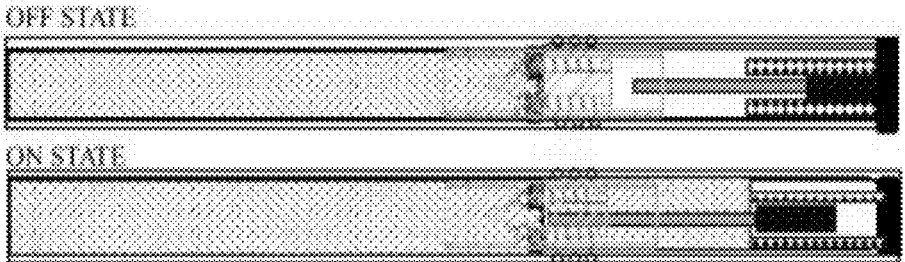
FIG. 6B shows ON and OFF state of the valve module.

In an embodiment, FIG. 6B, shows position of ON-OFF state of the valve module.

Figure 6C:
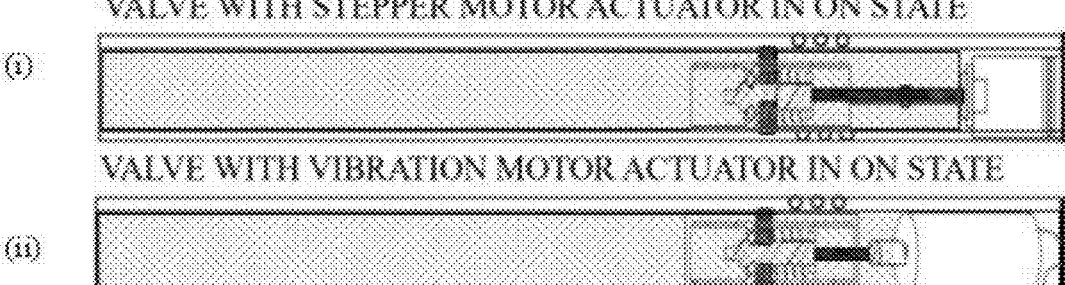
FIG. 6C shows the operation of (i) stepper motor, (ii) and vibratory motor as an actuator for actuating a push rod to open a valve such as a relief valve, according to one or more embodiments. The stepper motor and the vibratory motor could be a rod-like or coin-like motor.

In an embodiment, the device has a stepper motor. FIG. 6C shows the use of stepper motor and vibratory motor as actuator for actuating a push rod for opening and closing of the relief valve.

In an embodiment, a stepper motor may work in the following way: connected to a screw via a coupler, responsible for initiating movement. When the stepper motor rotates, it turns the screw, driving a nut threaded onto it. This rotation causes the nut to move linearly along the screw, with the direction of movement determined by the motor's rotation. The nut will attach to a push rod, and as the nut moves, it will push or pull the rod, creating linear motion. This motion will be directly linked to the relief valve, opening or closing it by applying force to the valve's mechanism. Control of this process could be managed by a stepper motor driver, which will receive signals to control the motor's speed, direction, and movement distance.

In an embodiment, a processor could send signals to the motor drivers, dictating the motor's operation and, consequently, the position of the push rod and relief valve. For example, when the processor sends a signal to rotate the motor in a specific direction, the nut and push rod will move, opening the relief valve. Conversely, when the motor's direction is reversed, the nut and push rod will retract, closing the valve. This system will allow for highly accurate regulation of the valve's opening and closing providing precise control over the flow or pressure of the liquid in the system.

A vibratory motor, instead of providing rotational motion, generates oscillating vibrations. A vibratory motor would be connected to the screw or another mechanism capable of converting the vibrations into linear motion. In the setup of FIG. 6C, the vibratory motor will generate oscillating motion, which is transferred to a push rod via a mechanical linkage, such as an eccentric cam or lever. The vibratory motion causes the push rod connected to a relief valve to move back and forth, thereby opening and closing the valve.

Figure 6D:
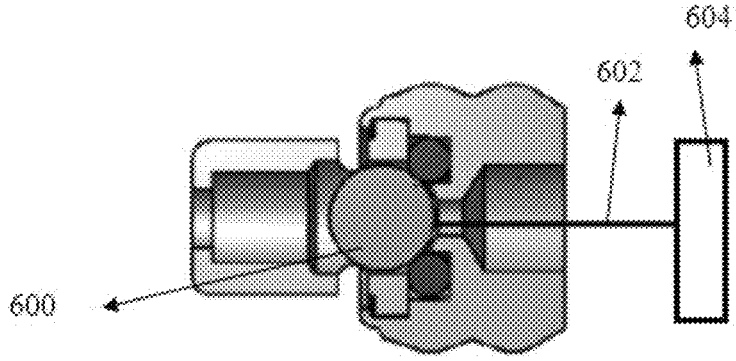
FIG. 6D shows a valve without stepper motor according to an embodiment.

In some embodiments, the device may have a valve module without a stepper motor. For example: FIG. 6D illustrates a valve without stepper motor, according to one or more embodiments. In this embodiment, the valve module is free of motor (e.g., stepper motor). As shown in the said figure, the valve has a vibrating plate 604 with a plunger needle like structure 602 adapted to fit in a 4 mm device. The needle like structure 602 is made up of a biocompatible material. The needle like structure 602 is not in contact with vibrating plate 604 when the valve is in OFF state. The valve functions as a relief valve (e.g., spring loaded relief valve). When the vibrating plate 604 is powered by a power module, it vibrates due to which the plunger needle like structure 602, meets the vibrating plate 604, pushing the relief valve (like a push rod pushing the head of the relief valve) to open (ON). At the opposite side of the plate, the needle like structure 602 is connected to a ball or a ball like structure 600. The needle like structure 602 may comprise an internal diameter of 100-200 μm. The plunger needle like structure 602 pushes the head of the relief valve from a direction which is opposite to the one-way flow of the drug.

The ball like structure 600 acts as a physical barrier to control the drug's movement. The ball like structure 600 allows drug flow only when a force from the direction opposite to the one-way flow of the drug, such as pressure generated by the vibrating plate 604, displaces the ball like structure 600 momentarily, enabling a precise amount of the drug to enter the needle. Upon actuation, the vibrating plate 604 generates, connected to the plunger needle like structure 602, generates controlled oscillatory motions (vibrations), which are transmitted to the needle like structure 602.

The vibrations are carefully calibrated in terms of frequency and amplitude to match the fluid properties of the drug (e.g., viscosity) and ensure smooth, consistent delivery, controlled flow rate and prevent blockage. The flow rate may be 1-10 μL/hour. The vibrating plate 1004 may oscillate at a frequency range of 20-50 kHz. These vibrations serve two purposes: they facilitate the smooth flow of the drug through the needle by reducing resistance and prevent clogging, ensuring consistent delivery. The needle like structure 602 attached to the vibrating plate 604 acts as the final conduit for the drug's release into the target tissue. The vibrations may also improve the dispersion of the drug into the surrounding tissue after it exits the needle like structure 602.

Different power sources could be employed by valve for its operations. Some examples of power sources that could be employed by valve module are explained in the below embodiments of this disclosure.

An implantable device of the present disclosure has a power supply module (or power module) along with other modules, parts, and features. The electronic module and/or the power supply module is/are separated from the rest of the modules of the device by a waterproofing (or another liquid tight barrier) to provide an isolated environment to battery and other components of the electronic module/power module. A power module of an implantable drug delivery device comprises at least one power source. The power source could work in continuous or may have a power switch that may regulate supply of power from the power module to rest of modules of the device. In some embodiments, the power source is a rechargeable power storage, harnessing energy from the environment, for example: energy could be harvested by converting kinetic energy of body movements into electrical power, or by utilizing body heat to generate power, or by capturing energy from the heartbeat, or by using the body's electromagnetic fields. In some embodiments, the device receives power through induction charging from an external source. In some embodiments, the power switch is a magnetic field activated switch. The power switch can also utilize other mechanisms available in the environment to turn the power on permanently. The power source and the power switch work together to ensure the device operates reliably, utilizing available energy efficiently and maintaining a consistent power supply. The device relies on a wireless charger to recharge its rechargeable battery, ensuring a continuous supply of electric power.

In some cases, the power source is a coin battery or button battery. Coin battery is a small battery made of a single electrochemical cell and shaped as a squat cylinder typically 5 to 25 mm (0.197 to 0.984 in) in diameter and 1 to 6 mm (0.039 to 0.236 in) high-resembling a button. Coin battery is adapted to achieve a reduced size AIMD. Stainless steel usually forms the bottom body and positive terminal of the cell; insulated from it, the metallic top cap forms the negative terminal. Batteries employed in the power module could be either primary cells or rechargeable secondary cells. It is also possible that device has a combination of primary and rechargeable secondary cells.

The power from the power source module is distributed to one or more components of the device such as sensors, piston, valves etc. Distribution of power to various components of the device is controlled by the electronic module. For example: a processor or simple timer of the electronic module manages the device's operations, including recording and adjusting medication dosing based on sensor inputs, monitoring fault conditions, processing sensor data for accurate operation, and overseeing battery status and power usage. In an embodiment, it may also store relevant patient medical history for reference. The system ensures that the implantable drug delivery device operates efficiently and effectively, providing necessary treatment while maintaining patient safety.

Figure 6E:
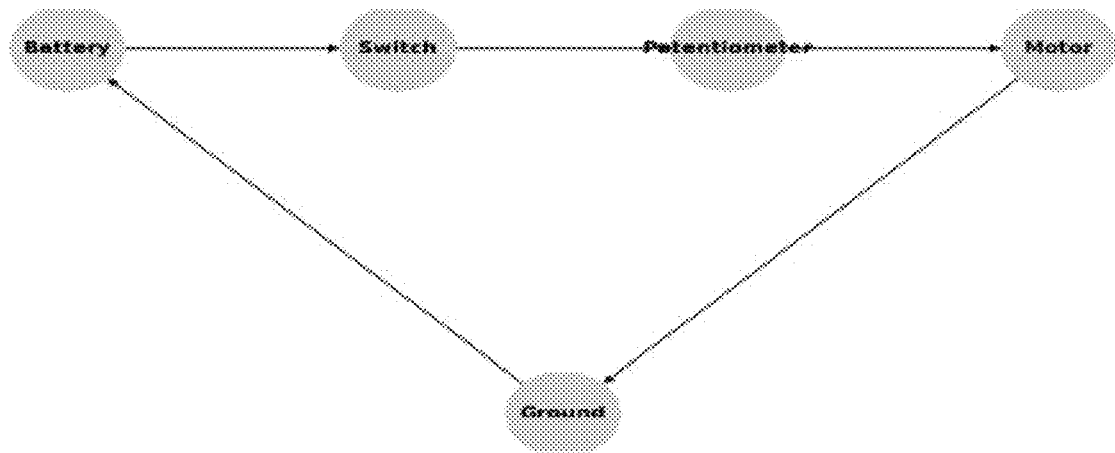
FIG. 6E shows a wiring diagram of a vibrating plate circuit, according to one or more embodiments.

FIG. 6E illustrates a wiring diagram of a vibrating plate circuit, according to one or more embodiments. The vibrating plate circuit comprises a battery, a switch, a potentiometer, a motor and a ground. All of the above mentioned components are in the size range of less than 5 mm. The battery is adapted to provide power to the circuit. The battery may be a button cell battery. The switch controls the ON/OFF state of the motor (e.g., Precision Microdrive 310-103, Precision Microdrive 304-116). The motor may be a coin vibration motor (cylindrical or pancake-shaped). The potentiometer is adapted to adjust the motor's speed. Adjusting the motor speed enables to adjust the vibration intensity. The motor comprises an eccentric weight attached to the motor. The eccentric weight is a small piece of metal or plastic that can be attached to the motor shaft off-centre. The eccentric weight is fixed to the motor such that it has enough room to rotate without hitting the plate or other parts. The eccentric weight is adapted to create vibrations when the motor spins. The eccentric weight is securely attached and balanced to the motor to avoid excessive wear on the motor.

The motor may be attached to the vibrating plate using several methods. Some of them are 1) Direct Adhesive Attachment, 2) Clamping, 3) Screw mounting, 4) 3D-Printed Motor Holder, 5) Elastic Bands, 6) Foam or Rubber Dampers. The motor may be attached to the vibrating plate using strong adhesives like epoxy glue, hot glue, or double-sided industrial-grade adhesive tape to secure the motor to the underside of the plate. The adhesive is vibration resistant. The motor may be clamped to the vibrating plate using small brackets or clamps. This is useful for removable designs where you might need to replace the motor. If the motor has mounting holes, the screws or bolts may be used to attach it to the plate. Corresponding holes may be drilled in the plate for precise alignment. A custom motor mount may be 3d printed to hold the motor snugly and can be glued or screwed to the plate. In an embodiment, the rubber bands or elastic straps used to tightly hold the motor against the plate. In another embodiment, the motor may be placed on a thin foam pad or rubber strip before attaching it to the plate to reduce noise and stress on the motor.

Figure 6F:
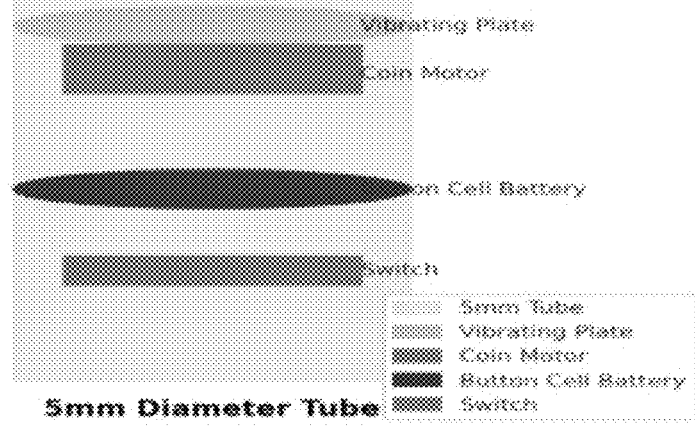
FIG. 6F shows an arrangement of components of a vibrating plate for 5 mm device, according to one or more embodiments.

FIG. 6F illustrates an arrangement of components of a vibrating plate for 5 mm device, according to one or more embodiments. The vibrating plate is attached directly to the motor shaft to achieve compact sized AIMD. The motor adapted to actuate the vibrating plate may be a coin motor. The coin motor is compact and fits snugly within the tube of the AIMD (5 mm). The button cell battery may be positioned below the motor to power the system. The switch may be a miniature tactile, or reed switch located at the base.

The reed switch may be a magnetic sensing component. The reed switch enables the device to respond to external magnetic fields for activation, deactivation, or control of the vibrating plate mechanism. The reed switch is a small, biocompatible, sealed device consisting of two thin ferromagnetic metal reeds inside a glass tube. When exposed to a magnetic field, the reeds come into contact (or separate, depending on the design), completing, or breaking an electrical circuit. The reed switch acts as an on/off switch for the device. By bringing a magnet near the implant, the switch closes or opens the circuit, activating or deactivating the vibrating plate. The reed switch allows external control of the device using a magnet, avoiding the need for invasive adjustments. The reed switch can be part of a feedback loop where the external magnet also triggers monitoring or diagnostic functions.

In some cases, the power source is a coin battery or button battery. Coin battery is a small battery made of a single electrochemical cell and shaped as a squat cylinder typically 5 to 25 mm (0.197 to 0.984 in) in diameter and 1 to 6 mm (0.039 to 0.236 in) high-resembling a button. Stainless steel usually forms the bottom body and positive terminal of the cell; insulated from it, the metallic top cap forms the negative terminal. Batteries employed in the power module could be either primary cells or rechargeable secondary cells. It is also possible that device has a combination of primary and rechargeable secondary cells.

In an embodiment, the implantable device has an electronic module along with other modules, parts and features. An electronic module has chips, electronics housing and/or electronic components. In some embodiments, the electronic module of the implantable drug delivery device comprises without limitation one or more sensors, communication system, power switch, data stores that interact to ensure proper functioning. Sensors may continuously or discontinuously monitor various parameters such as drug levels within a patient's body and/or within the device, patient vitals, and environmental conditions, etc., to provide real-time data to the processor for processing. The processor could manage operations such as receiving data from various device components such as sensors and/or battery, controlling valves to release medication as needed. The communications system, e.g. featuring a Bluetooth module, facilitates wireless communication with external devices for data exchange and remote control. Wi-Fi may enable internet connectivity for remote monitoring and updates. Alternatively, or additionally, the electronic module may be configured to form or form a connection with a handheld device that could be used by a user to monitor and control the device remotely.

The power from the power source module is distributed to one or more components of the device such as sensors, piston, valves etc. Distribution of power to various components of the device is controlled by the electronic module. For example: a processor or simple timer of the electronic module manages the device's operations, including recording and adjusting medication dosing based on sensor inputs, monitoring fault conditions, processing sensor data for accurate operation, and overseeing battery status and power usage. In an embodiment, it may also store relevant patient medical history for reference. The system ensures that the implantable drug delivery device operates efficiently and effectively, providing necessary treatment while maintaining patient safety.

Figure 7:
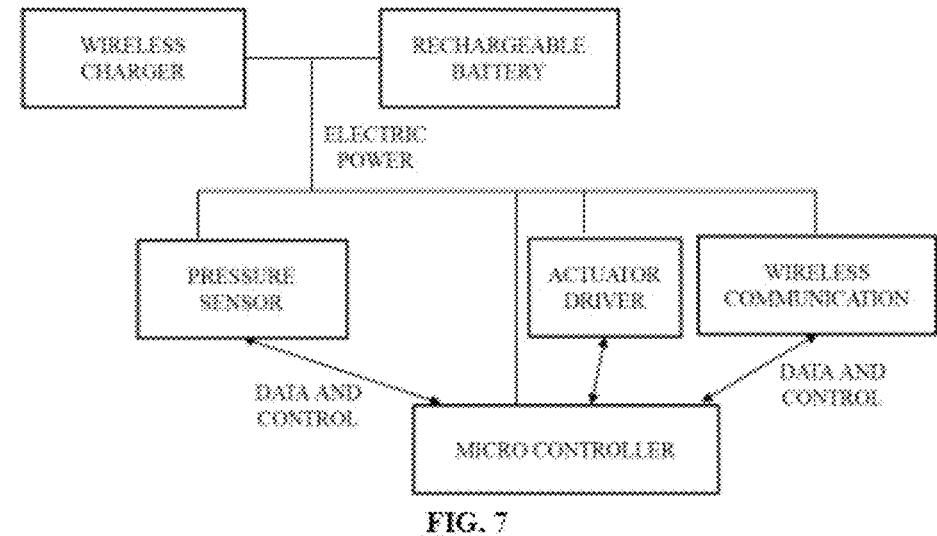
FIG. 7 shows electronics and power utilization by different modules of the device, according to one or more embodiments.

Referring to FIG. 7, it shows power distribution to various components such as a pressure sensor, conductivity sensor to monitor the internal environment of the device and drug levels. The actuator driver uses this power to control the release mechanism, ensuring precise drug delivery.

In an embodiment, the power switch controls the device's power state, allowing it to be turned on or off as needed. In an embodiment, an electronic signal from the fourth chamber is transmitted to the first chamber, second chamber and/or third chamber via an electric circuit. In an embodiment, the electric circuit is printed on the implantable device.

In some embodiments, the processor of the electronic module is configured to analyze the medical characteristics of the patient to determine a symptom associated with a medical condition such as without limitation measuring physiological parameters of the host of the device. In an embodiment, processor is configured to analyze medical characteristic of the patient to determine a symptom associated within the patient, wherein the symptom corresponds to a decrease in respiratory rate, a decrease in heart rate, a decrease in blood pressure, deviations from normal body temperature, passing out or an unresponsive loss of consciousness, skin color changes, abnormal breathing, fast, slow or irregular breathing, severe chest pain, seizures, severe headaches, difficulty in breathing, delirium, agitation, and/or anxiety. In some embodiments, the processor is further configured to send an alert or notification wirelessly upon detection of the symptom.

The wireless communication system of the electronic module enables the device to transmit data to external devices, allowing for remote monitoring and adjustments. The processor may play a central role in managing data flow and device control, processing inputs from the sensors and executing commands to the actuator.

In some embodiments, the device further comprises a biosensor coupled to the processor to verify a medical characteristic of the patient prior to delivery of a drug. The biosensors provide real-time data of drug levels and/or health related markers, offering valuable insights for personalized. For example, a biosensor can monitor an opioid agonist or the partial opioid agonist, wherein the biosensor comprises a pulse oximeter, a heart rate sensor, an ECG sensor, a skin sensor, a temperature sensor, and/or a blood flow sensor.

In an embodiment, the electronic module is also configured to data logging and storage functionalities. This helps to retain important information such as dosing history, sensor readings, fault conditions, and battery status, which are crucial for monitoring and adjusting treatment.

The term implantable device or AMID is interchangeably used in the specification.

In an embodiment, on operation of the power supply module of the device: (i) the permeability module allows inflow of fluid from the semipermeable membrane into the osmotic chamber to establish an osmotic pressure, (ii) the electronic module is configured to switch on and off the valve module as per a predetermined program set within the device to regulate flow of the drug from the drug chamber. In an embodiment, the inflow of a fluid through semipermeable membrane into the osmotic chamber is on a real-time basis.

As shown in FIG. 2, the drug outlet is near the end of the drug chamber. The valve module features a relief valve with a hermetically sealed actuator. Functioning of the valve module is explained in detail in FIGS. 6A to 6D. In the top figure in FIG. 2, the valve is closed, and the piston is compressed. In the middle figure, the valve opens, and the piston expands to discharge a dose. In the bottom figure, the valve closes, and the back piston moves forward to compress the piston again. In an embodiment, the drug outlets are present near the opposite end from the permeability module of the tube. In an embodiment, the drug outlet may be distributed over the area of the drug chamber. The topmost figure in FIG. 2 shows position of valve state enclosed within a casing 222 of the implantable device just after implantation in a host. The valve 208 is closed, and the compressible piston 204 is in a compressed state, that means the implantable device is activated.

On the activation of the electronic module, due to hypertonic solution present in the device or more specifically in the osmotic chamber 224, fluid (such as water) from the blood serum starts moving across the semipermeable membrane 226 into the hypertonic solution, entering the osmotic chamber 224 of the device. In an embodiment, the hypertonic solution could be a solute such as NaCl or glucose.

Since the valves are closed by a seal 218, the ingress of fluid builds an osmotic pressure within the device. This pressure may compress the piston. An actuator 216 is configured to open valve (without limitation such as, relief valve) using the push rod 220. The sensor 202 senses the built of the osmotic pressure and communicate with the electronics 212. Actuator is controlled by electronics 212 of the device. The compressible piston 204 uncompresses thereby simultaneously releasing the drug outside through the drug outlet 210. When the valve closes again, the osmotic pressure rises again compressing the compressible piston. Power to actuate the valve is provided by a power source 214 such as a battery.

When the relief valve 208 is closed and the system is in equilibrium, the internal pressure in the osmotic chamber 224 and the drug chamber will be the same. As the relief valve opens and the drug starts delivering, the pressure in the drug chamber 206 decreases relative to the pressure in the osmotic chamber.

In reference to FIG. 2, when the valve is opened, the front end plate of the compressible piston displaces by a distance 'd' and therefore the shot size will be equal to the cross sectional area (of the drug chamber) times d. Subsequently, when the valve is closed, the back end plate of the compressible piston moves a distance 'd', while the front end plate of the compressible piston remains stationary. Front end plate of the compressible piston is towards from where the drug comes out. Back end plate of the compressible piston is towards permeability module.

The amount of discharge of the drug is proportional to a distance travelled by the compressible piston. The position of the back of the one end can be before a discharge operation can be compared with the same with the same position of the end relative to the casing after the after the discharge operation.

Activation of the implantable device to start the operation is either manually or automatically. Manually signifies with user intervention; and automatically signifies without user intervention. In an embodiment, a manual process of activation includes a touch sensor and/or a pressure sensor.

In some designs of the implantable device the space of the compressible piston is filled with gas.

In an embodiment, the device utilizes Gibbs free energy to drive the compressible piston.

In an embodiment, a time taken for fluid to flow through the semipermeable membrane will be of several orders of magnitude higher than the time it takes for the drug to be ejected out via the compressible displaced piston. For example: valve opening will be instantaneously within few secs, whereas inflow flow of fluid through the permeability module could vary from minute to hours. Order of magnitudes could be about 30 times, 40 times, 50 times or more.

When the relief valve opens, the pressure drops, that means, theoretically some liquid is going to start ingressing, but between the opening and closing of the valve, the amount of the liquid that will ingress through the permeable membrane will be almost negligible compared to the volume of liquid that has been discharged via the one or more drug outlets.

In an embodiment, due to the compressible piston in the device, each dose correlates to the piston moving by a distance 'd'. Since the compressible piston is like a spring, therefore the time to move a distance 'd', will be almost instantaneous, whereas the time for that volume of fluid to ingress through the semipermeable membrane will possibly be in several seconds to minutes to hours.

Opening and closing of the valve occur repeatedly in a cycle, allowing the compressible piston to compress and uncompress alternately.

In an embodiment, a rate of osmotic exchange needs to be assessed to determine the rate of pressure change in the osmotic chamber during drug delivery based on the permeability of the semipermeable membrane since this could also affect distance "d" travelled by a compressible piston. If the rate of osmotic exchange is very low, the pressure in the osmotic chamber will likely remain the same as the pressure in the equilibrium condition.

In an embodiment, a rate of osmotic exchange needs to be assessed to determine the rate of pressure change in the osmotic chamber during drug delivery based on the permeability and conductance of the semipermeable membrane.

The processor in the implantable drug delivery device handles data flow by acting as the central processing unit that coordinates all the device's functions. It receives input from various sensors, such as pressure and conductivity sensors, which monitor the internal environment and drug levels. The processor processes this data to determine the appropriate actions, such as adjusting the dosage or triggering the actuator to release medication. It also manages communication with external devices through wireless modules, ensuring that data such as dosing history, sensor readings, and battery status are transmitted for remote monitoring and control. Additionally, the processor stores critical data in its memory, including fault conditions and medical history, which can be accessed and analyzed to optimize treatment. By efficiently managing data flow, the processor ensures that the device operates smoothly, making real-time adjustments based on sensor inputs and maintaining reliable communication with external systems. This integrated approach helps maintain the device's performance and enhances patient safety.

In an aspect of the disclosure, an active implantable medical device (AIMD), comprising: a permeability module to allow ingress of a fluid into an osmotic chamber of the AIMD, a piston, a drug chamber comprising a drug or being provided to receive a drug and a valve module to allow flow of the drug from the drug chamber to outside the AIMD through one or more drug outlets present in the AIMD, wherein an electrical actuator is configured to control a dose frequency of the drug released from the drug chamber, and wherein the AIMD is an electrically powered device. AIMD is configured to control a dose size of the drug mechanically without an electrical power supply. In an embodiment, the volume of the dose size varies by no more than ±25% from that of a target volume irrespective of a time duration for which a flow discharge valve.

Figure 8:
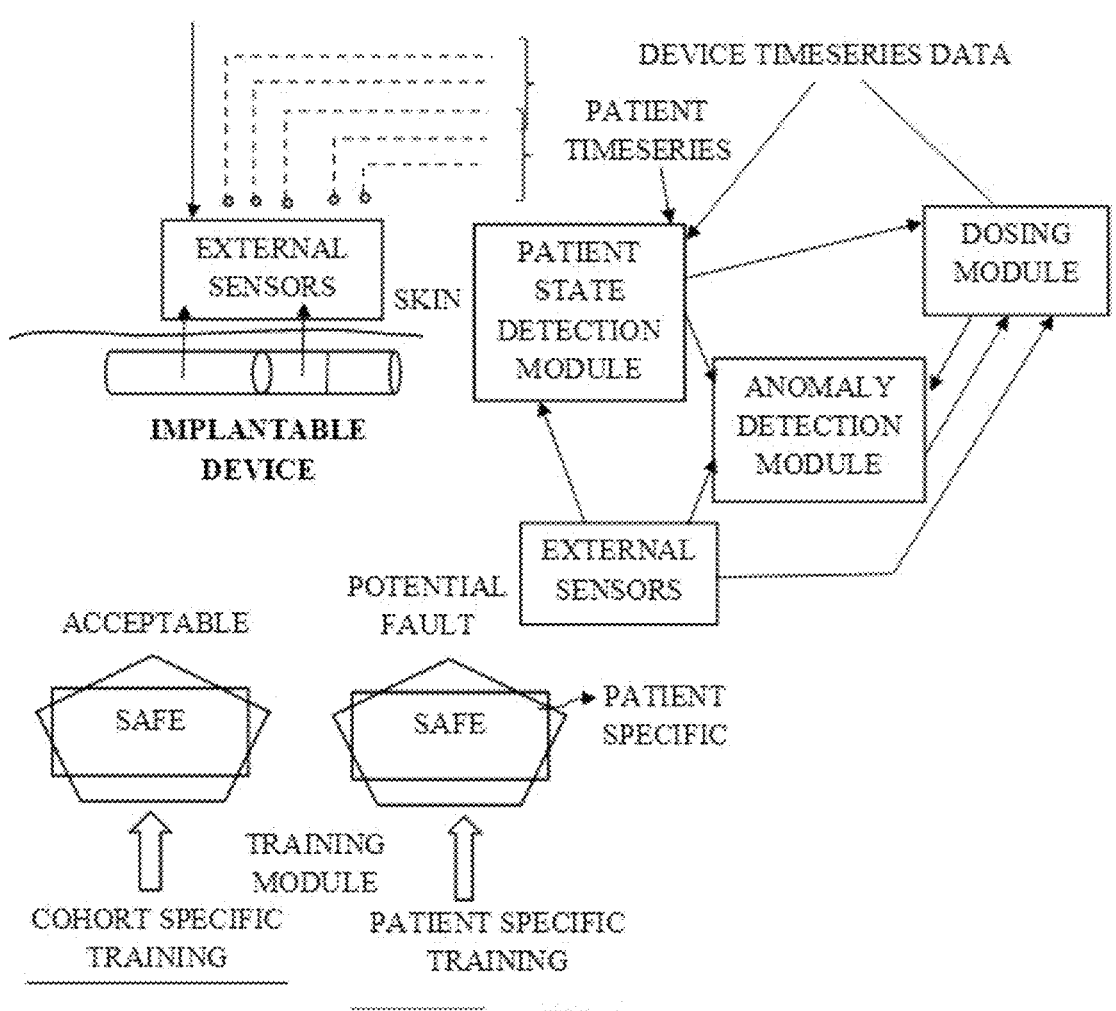
FIG. 8 shows data flow in a system comprising an implantable device according to one or more embodiments.

FIG. 8 shows a system with the implantable device, and flow for data flow to and from the implantable device according to one or more embodiments. The system comprises a receiving unit, an implantable device, and an external unit. The external unit comprises external sensors. The receiving unit may be the unit in the AI engine. The implantable device may have a collection of sensors, and a chip. The chip may be part of the electronics module of the implantable device. The sensors could determine a number of metrics. The chip of the implantable device may be a programmable chip and/or wireless communication chip, that is configured to interact with the external unit. The external unit comprises other types of sensors (like a motion sensor, biosensor) placed in and on the body of the user but separate from the implantable device.

FIG. 8 shows a device, an external unit, some sensor data coming from the device, some sensor data coming from the external unit, which is interfacing with the implantable device. The data sets may be going into the implantable device as time series data or on real-time basis.

The device data includes e.g., internal temperature and osmotic chamber pressure, drug pressure, flow rate etc. of the implantable device.

The data coming from the patient, which is patient data, could be from the external sensor, for example, the sensor to measure an oxygen level, an internal sensor could be a biosensor placed on the implantable device.

In an embodiment, the system comprises an anomaly detection module which allows us to have a variety of different time series data or real-time data, which can be plugged in (as in a hospital bed setting). The anomaly detection module helps to know if the implantable device is working according to a determined program. In case the anomaly detection module finds or predicts any problem in the system, it would proactively (without any time lapse or on real-time) inform the user or the healthcare provider of one or more possible danger. The possible dangers could be informed via displaying/texting a signal, sending notifications on a mobile etc. or giving an alert signal on the smart alert signal devices. In an embodiment, the smart alert signal device includes a mobile.

The system also enables the user to plug in another sensor in addition to the integrated system. An AI engine, depending on how many different time series data, determines the offset of the patient data and the device data. Based on offset detection, the system via the AI engine determines the anomaly. The AI engine is trained for offset.

In an embodiment, an AI engine is a pre-trained AI engine or trained on patient specific training. The patent specific training includes supervised training after the device is implanted and calibrated in the human body. Training also includes operator adjusting the possible faults and problems, adjusting lag expectation or etc.

In an embodiment, the system includes patient state detection module. The patent state detection module could detect a physiological parameter of the patient, as well as demographic information of the patient such as age, race, gender and other health conditions etc. The AI engine takes information in order regarding parameters of the device, and a variety of different data points coming in. Learning by the AI engine could depend and could also change based on the offset between the time series data coming from the patient and time series data coming from the device. The AI engine also learns over time, depending on the medical state of the patient, and other data received over time. The AI engine undergoes on the fly training, like patient specific training, variations in the device, etc. The AI engine then learns more about the patient, their habits and what they do on a regular basis. The AI engine then, based on the learnings, undergo start triggering anomalies, and alerts. The AI engine also gets feedback from a human being. The AI engine may provide different types of alerts such as a medium level alert, a low level alert and a high level critical alert. For low level alerts, the AI engine notifies operators to come in and observe the data set, and then further trains the AI. The observer determines whether the alert is a medium level alert, a lower level alert, or a higher level alert. The operator may provide customized training, which is happening on the data. The operators may provide the training on a regular basis, not real-time. The operators may analyze low level and medium level alerts and look at that data, and further customize and clean the datasets for that patient's system to train the AI engine. In one embodiment, the AI engine customizes the data based on the anomaly detected with the cohort of the patient and learns from the datasets associated with the other patients in the cohort. Every patient might be different and have slightly different metrics. The AI engine makes use of the help desk center (e.g., network operating center) in the telecom space. The help desk center observes the datasets on a regular basis by human beings, and then the datasets are further altered, improved, and worked in.

In an embodiment, the system includes a dosing module. The dosing module could help in adjusting the dose according to the patient's need. In an embodiment, the said module helps to improve precision to the dosing mechanism of the device.

In an embodiment, the system enables a single operator to look at multiple patients.

In an embodiment, AI engine can apply clustering algorithms like k-means, DBSCAN (Density-Based Spatial Clustering of Applications with Noise) on dosage data, patient state and patient biometric data to group datasets in a multi-dimensional clusters space together. Any data points occurring outside these multi-dimensional cluster shapes is considered a potential anomaly. Prior to sending data to the clustering algorithm, the data would be adjusted for lag between cause and effect. These multi-dimensional clusters can be pre-created based on training data from several devices and patients. Subsequently these shapes will be trimmed/adjusted to patient demographics (age, gender, race, medical condition etc.), and then in the last steps, further trimmed and adjusted for the specific patient. What is an anomaly for a regular patient with similar characteristics might not be an anomaly for specific patient's depending on their group of medical conditions and medications that they are taking. In k-means algorithm Anomalies can be identified by analyzing the distance between each data point and its corresponding cluster center. For DBSCAN, points that are not part of any cluster are treated as noise, and in this context, they can be considered anomalies. The AI engine initially may not know how many clusters you need to cluster. The AI engine learns and improves further in real-time and/or in a simulated environment to kind of have to experiment with a bunch of different numbers to figure out what is the most optimal number of clusters.

In an embodiment, the AI engine may receive the time series data or real-time data in a multi-dimensional space. For example, the AI engine may receive the time series data in a representation (for example, in a two or three dimensional space). The datasets are read including patient's data and/or device data. The AI engine learns, in order to detect anomalies, within what range all of these dataset's span. The sphere is created, which is the boundary for datasets, which could be a sphere. The AI engine also learns, based on the datasets received, what is the shape within which every dataset falls. The AI engine, upon learning the multi-dimensional shape of the cluster, determines an anomaly when a dataset goes outside that shape. The shape drawn is then highlighted for anomaly detection. The AI engine learns the boundary and looks for data within that space and/or the boundary. For example, for a specific patient, the shape could be different. For the patient already having a heart issue, the heart will function differently, and datasets will be different. When the pre-trained AI engine is implemented, the accuracy of the functioning of the AI engine is not optimized, because the AI engine is initially trained on different devices and different patients (similar in nature, but nevertheless not the same patient). For that specific patient having a heart issue, the AI engine needs to be retrained and adjusted. The datasets received and the plot made for that specific patient may have a shape that looks slightly different. The shape of the specific cluster, in that multi-dimensional space, might mostly fit inside the space of a healthy patient. There could also be certain points coming from the regularly planned shape (e.g., based on the trained person). The AI engine learns the above in a few iterations. Upon learning the above, the AI engine in certain cases may then use that patient as a base patient in that cluster or category. The AI engine creates the cluster properly over time. In one embodiment, the AI engine is trained in such a way before implanting or putting it into action. The cluster then gets recorded over the network. Once the AI engine creates the clusters properly and settles the datasets, the AI engine accuracy improves and will not provide any more abnormal alerts.

The other issue that the AI engine might be facing is false positives. In an embodiment, the system reduces the number of false positives using a patient's feedback. The patient's feedback can be thumbs up or thumbs down which states whether they're feeling okay or not respectively. The patient feedback trains the AI model further. For instance, in an embodiment, the device has a voice module device. The patient can provide feedback via a voice module device. The device might beep and then ask a question. The device might beep further, and then the patient can tap it to provide the input.

In an embodiment, the device may ask a series of questions, e.g. yes/no questions. The patient may then make a single tap for "Yes", or two taps for "No" (other patient inputs or patient actions are possible as well to answer the questions with "Yes" or "No"). The patient's feedback can be provided via the device associated with the user without the need to go back to the system. The voice module is an interesting data feed for the system. The voice module allows us to read that data, they are easy to put in and then train on it. A voice module could be helpful for a lot of these patients, sometimes if elderly living alone. The voice module can detect when the patient shouts. The voice module further detects when there is stress in the voice itself and then takes it as a patient input. So patient feedback could come as direct from the voice module from surroundings and a variety of other ways that data could be collected. The voice module just senses inflection instead of the actual content. The voice module does not require to actually interpret the voice except for indicators. The voice module figures out if the voice is stressed or determines that someone is shouting for help.

In an embodiment, the AI engine may be combined with different inputs e.g., inputs from accelerometer sensor, biometric sensors, and voice modules. For example, when the patient falls and they are shouting for help, a voice input from the voice module and sensor inputs, like heart rate from biometric sensors, are read. The different inputs from different axes get correlated by the AI engine and provides training to the AI engine.

In an embodiment, an AI engine may undergo two types of training. The first is initial training (pre-training), and subsequent (second) re-training to fine tune the AI for the specific device and specific patient. In the pre-training, the AI engine learns to understand the group of the patients. The patient group may be categorized based on demographics. The AI engine is a trained device initially for different categories, for example, kids, men, women, boys, girls, older people, etc. The AI engine undergoes different types of training in particular categories based on the current state, e.g., sleeping, awake, exercising, eating, etc.

In an embodiment, the AI engine first detects the state. The AI engine comprises a state detection module which detects what state the person is in. The state detection module, depending on time of the day and various other metrics, figures out the current state such as sleeping, or awake. Based on the current state, the AI engine instructs the implantable device to provide dosage and/or dynamically adjust dosage at appropriate times. The AI engine comprises a group identification module that determines which group or category the patient falls in. The AI engine may also perform lag detection between the data of the device and the patient. The AI engine may also monitor how the patient is performing over a longer period of time. The AI engine is capable of receiving medical conditions from the patient feedback. In one embodiment, the AI engine extracts the medical conditions (e.g., a patient's undergoing medications) from the previous medical records. There might be different medical conditions, and the AI engine learns more about the medical conditions and the corresponding treatments/medications provided. For example, for a heart patient the AI engine defines medical conditions and determines what the cohort for that patient is.

In an embodiment, the system allows cohort specific training. This training helps to customize models using dozens to thousands of high-quality tasks and grade the model's response with reference answers. This technique reinforces how the model reasons through similar problems and improves its accuracy on specific tasks in that domain.

The AI engine also gets trained regarding approvals coming from FDA approvals for specific types of patients having specific conditions and the like. The AI engine also learns about the datasets based on which have been trained for those specific conditions. The AI engine also gets trained in other types of medical conditions that have enough patients. The AI engine gets trained in three types: supervised learning, unsupervised learning, deep networks, and large language models. Supervised Learning comprises labelling. As the system comprises a data set, supervised learning is a labor intensive, costly process, where one has to go through the data set, start labeling everything coming from it. The data set has to be read and marked as an anomaly or not an anomaly. The supervised learning happens for a longer period of time for a lot of data sets. The AI engine eventually starts learning and figuring out the labeling. The second one is unsupervised learning. Unsupervised Learning is nothing but clustering which is another option. And the third option is deep networks. The AI engine starts using deep networks. And the fourth one, within that deep network classification coming in is large language models, which are becoming popular, (for example: ChatGPT®). The AI engine uses large language models in detecting background noise. The large language model can understand the voice data from a microphone and transcribe it to understand content and tone of the voice. The model can also detect unusual noise, calls for help, and sense anxiety, stress or distress in the voice of patient. The voice inputs may be received from the microphone. The Large Language Model can classify background noise with voice inputs and start classifying the background noise and extracting the voice inputs. The AI engine, after dosing, monitors some other parameters based on recent case studies or recent medical scenarios. The AI engine monitors certain other parameters, which become more important based on the recent medical scenarios. The AI engine keeps monitoring the regulations and/or recent updates in the medical field and may monitor other parameters dynamically after the dosage is done. The AI engine may communicate with medical database that keeps track of the recent updates in the field. The AI engine may comprise a natural language processing module that interprets the context and provides recommendation to the AI engine. The mapping also might become fairly important for us down the line. The AI engine tracks and updates the mapping dynamically to keep the changes up to date.

In an embodiment, the AI engine comprises a system that allows the user to plug in any kind of time series dataset, and then start training the AI engine quickly. The AI engine enables any kind of time series data to be fed into the system. The AI engine comprises visual interfaces for various data points. The visual interface is one where the different data points can be plugged in. The visual interface is also adapted to read all of these datasets, and constantly train the AI engine on a large number of patients. The AI engine can then be specifically customized for a specific patient. The AI engine also works and functions when few data points are removed from that patient. For example, the patient has a sensor on their arm, and while sleeping the oxygen sensor falls off in your sleep. The patient may not want an alarm to go off and notify anyone that the oxygen sensor is off. The AI engine works even in such a scenario when some of these time series datasets flatten out.

In an embodiment, the AI engine also functions and provides anomaly detection and/or dosage adjustment when the device flattens out or certain device sensors stop functioning. The AI engine functions in a manner where even if certain data sets are not available, or if additional data sets are available, the AI can adjust and continue to make decisions. It can replace one parameter with another strongly co-related parameter/time series. The AI engine is able to deal with certain critical scenarios. For example, the AI engine has certain data points constantly when a patient is on a ventilator. But if there are other sensors plugged into the patient, and if you have that data coming in, the AI engine takes in that data as an additional data feed and incorporates it. The system starts training based on that additional data feed, and then starts learning based on that data, and then starts detecting based on patient/agent/care provider feedback, or dosage details. The AI engine performs anomaly detection based on additional data as well. In one embodiment, the additional data can be generalized. In one example, the feedback for the age of the patient may be specific, and it cannot be generalized as much, because feedback for that age has to be specifically based on the person. The AI engine regarding the dosage part has to be pre-trained through and customized based on the recommendation of the doctor and allows the fine tuning of the dosage of the patient to take place remotely. The fine tuning may happen through a telemedicine operation where the patient is talking to operators, nurses and doctors and providing their feedback. The doctor may provide instructions via the user interface to the AI engine. The AI engine then observes and sees what's happening to the patient by monitoring the sensors. In one embodiment, the doctors may also manually observe the readings. The AI model could be an incremental model where via the user interface the dosage can be adjusted dynamically during these particular events. In one embodiment, the AI engine itself, upon monitoring, steps up the dosage. For example, the AI engine steps up a dosage by 10%, if certain events are detected.

In an embodiment, the AI engine might work under different conditions. The AI engine is enabled to automatically choose the dosage. The AI engine, until it learns the dosage, the patient/the caregiver/the doctor, could start off with medications, like antibiotics which have instructions available via an interface. The AI engine also learns that certain antibiotics have stepped dosage requirements based on recent updates in the external medical database through NLP. The AI engine can incrementally increase the dosage and observe if the patient is reacting or not reacting to the dosage. The AI engine may also receive approval by the doctor before stepping up the dosage requirements.

Figure 9:
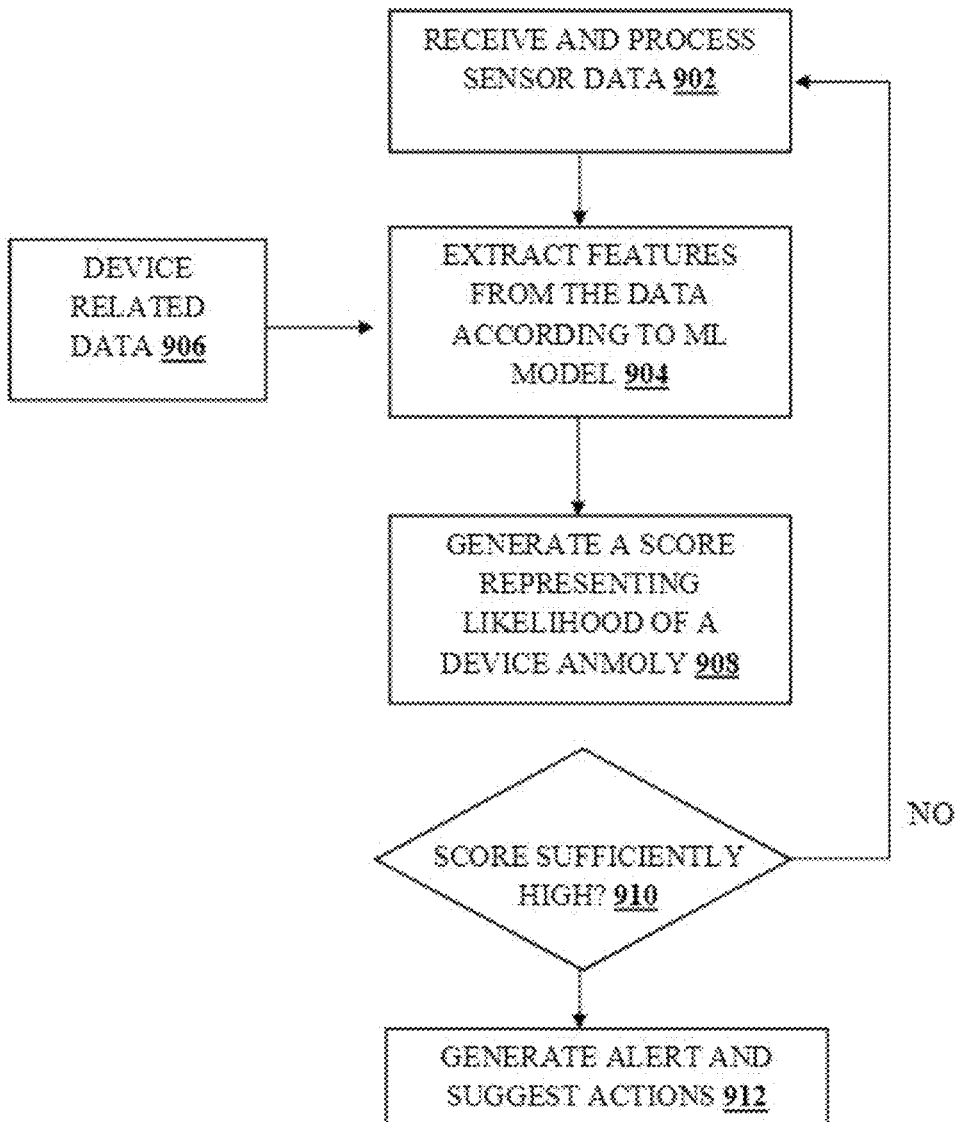
FIG. 9 shows an example flow chart for detecting device anomalies using a machine learning model, according to one or more embodiments.

In an embodiment, FIG. 9 shows an example flow chart for detecting a device anomaly using a machine learning model. The device anomaly may comprise an implant failure and/or side effects associated with the implantable device. The system may receive data associated with one or more sensors 902 from the implantable device. Data pertaining to the performance of the implantable device can be gathered using any type of sensor, for example, pressure measurement, leakage, infrared measures, temperature measures, or any other information measured or detected by sensors. In an embodiment, a sensor output may be the result of one or more sensors capturing environmental information associated with the subject having the device implanted. The system may receive other data 906, for example, from wearable devices, external electronic medical record databases, and attachable monitoring devices. The machine learning model 904 of the system can process the data to generate a score representing likelihood of a device anomaly 908. If the score is sufficiently high 910 the system sends an alert and suggests action 912 via a user device. The user device may comprise a mobile phone or a laptop. In some embodiments, the model is already trained.

Figure 10:
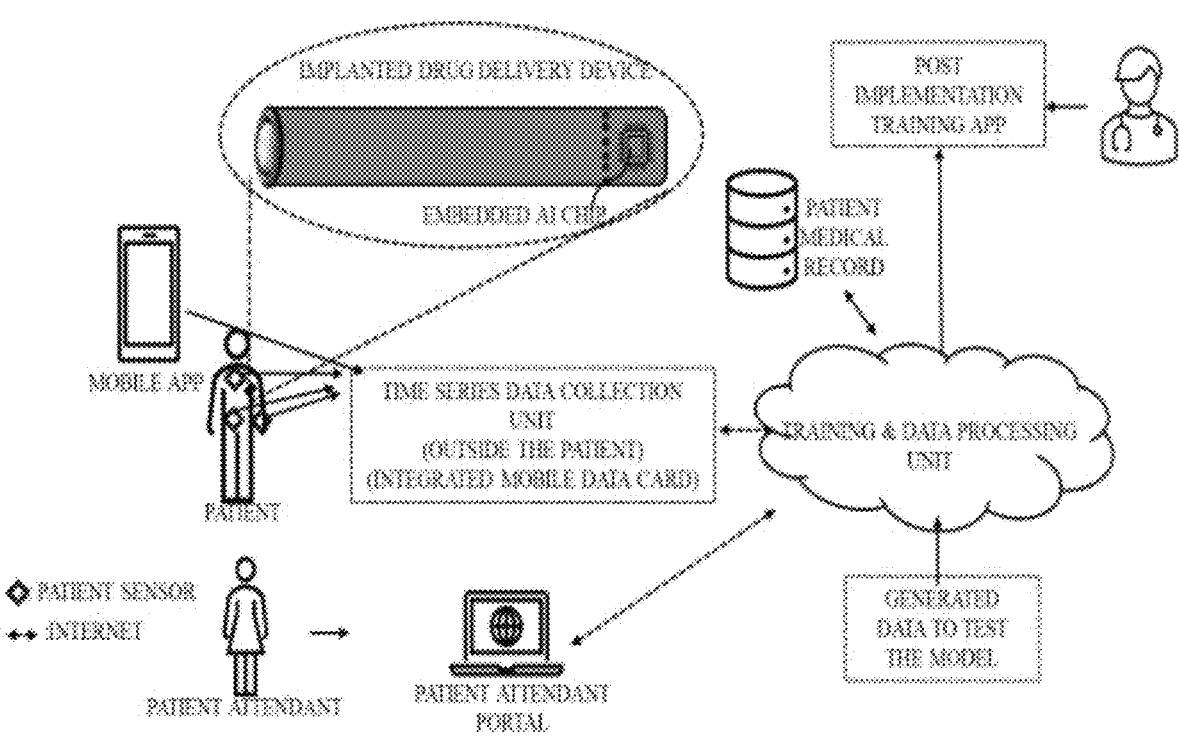
FIG. 10 illustrates the AI architecture for post-implantation training of the implantable device, following one or more embodiments.
Figure 10:
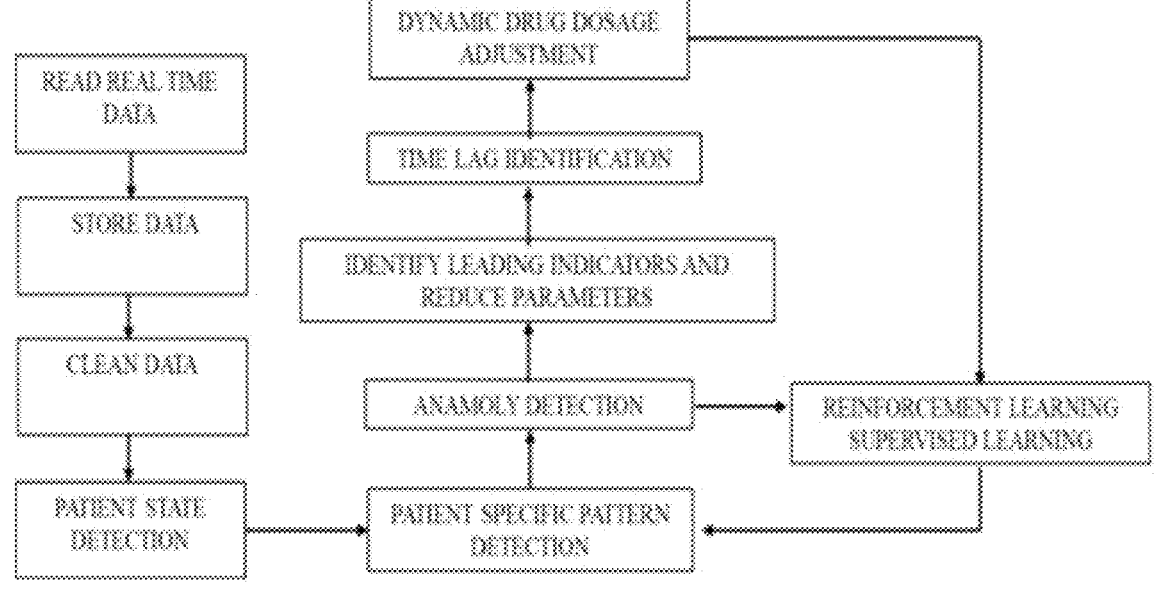

In an embodiment, FIG. 10, illustrates the AI Architecture for implantable device monitoring, according to one or more embodiments. In the final monitoring stage, the doctor no longer needs to constantly supervise the patient's implantable device and send new data to the Training & Data Processing Unit. Instead, a trained attendant from a Network Operating Center (NOC), shown in FIG. 10 as Patient Attendant Portal, will monitor the patient/device through the NOC-style web user interface if required. The software will enable attendants to monitor multiple patients, and AI will visually alert the agent if any data from the patient or device indicates malfunction or a health emergency that requires attention as follows:

1. A web user interface for Doctors and Device specialists to enter data regarding the patient's prescribed drug dosage from the implantable device and criteria to determine health emergencies and the patient's state based on the data coming in from the patient's vital sensors.

2. This data will then be sent to the Training & Data Processing Unit (the "central brain" of the design), consists of multiple Artificial Intelligence (AI) models, including but not limited to: Generative AI to predict what comes next, Anomaly detection, and deep learning networks to process and analyze all the data that is sent to it. See step 9 below for more details.

3. Medical history, including data regarding the patient's height, weight, gender, race, etc., will also be sent to the Training & Data Processing Unit from the patient's medical records database.

4. Real data from a cohort of patients experiencing similar health conditions and real data from anonymous patients, as well as data generated for patient health emergencies or device malfunction, will also be sent to the Training & Data Processing Unit through the web user interface.

5. Patient Sensors measure the patient's vital signs such as body temperature, heart rate, blood pressure, blood glucose level, etc. This time series data will then be sent to the Time Series Data Collection Unit.

6. The Time Series Data Collection Unit is external from the patient's body and collects the time series data from the patient sensors, mobile app, and implantable device. The collected time series data is then sent to the Training & Data Processing Unit.

7. The Implantable Device contains an Embedded AI Chip that constantly collects device time series data, such as the pressure/position of the valve as well as battery level. This data is then sent to the Time series data collection unit. When the implantable device loses connection to the Time Series Data Collection Unit (the "central brain"), then the embedded AI chip will take over, using the limited functionality that it has.

8. The mobile app will take input from the patient on a regular basis, including weight, height, medication, schedule, etc. This data will then be sent to the Time Series Data Collection Unit.

9. As the Time Series Data Collection Unit reads in and stores real-time data, it will clean the data, look for patterns, identify parameters with a strong correlation and eliminate unnecessary parameters, identify time lag between medication and changes in vital signs, and accordingly recommend drug dosage amounts/times/frequency to best suit the patient.

10. After implantation, the doctor/device specialist will have access to new data on the web user interface regarding the device operation status, reinforcement training, supervised training, and historical data classification.

11. The patient will also be given an external device to place on the skin, which contains a rechargeable battery and will charge the implantable device. It also contains an accelerometer and voice input module to detect if the patient is falling or in pain.

12. When the Training & Data Processing Unit makes drug dosage recommendations, they will be sent back to the implantable device to be administered.

13. A patient attendant will monitor the patient's vitals and calibrate the sensors if sensor drift is detected.

14. In the post-implantation training stage, Reinforcement Training and Supervised Learning will play key roles. After detecting patterns in the patient's and the device's data, the Training & Data Processing Unit will make predictions about future time series. If the outcomes don't match up with predictions, that will be considered an Anomaly, and the Training & Data Processing Unit will adjust its predictions accordingly.

15. In the final monitoring stage, the doctor will no longer be frequently supervising the patient's data through the web user interface. However, help desk attendants at a Network Operating Center will have access to that same data and can make any changes through the web user interface when necessary.

16. The NOC-style web user interface will allow help desk workers to access data for multiple patients and check on one of the patients when needed (for example, if the AI detects a health emergency or device malfunction).

Detection of Device Failure by Monitoring Displacement of the Back Face of the Compressible Piston and Osmotic Pressure in the Osmotic Chamber In an embodiment, the displacement of the back face of the compressible piston is monitored in accordance with Equation (I) (shown below). If the displacement of the back face of the compressible piston device is in accordance with Equation (I), then the device is working correctly. In an embodiment, the expected osmotic pressure data is measured according to Equation (II).

The osmotic pressure in the osmotic chamber is as follows: $\pi=icRT$, where $\pi$ is the osmotic pressure and i is the Van't Hoff factor, C is the concentration of the solute and R is the gas constant. The displacement of the back face of the compressible piston ($L_2-L_1$) as a function of $\pi$ is calculated as follows:

$$C = \frac{Mass}{Volume} = \frac{Mass}{Area \times Length} = \frac{M}{A \times L}$$

$$Therefore, L_2 - L_1 = \frac{M}{A}\left(\frac{1}{C_2} - \frac{1}{C_1}\right)$$

$$L_2 - L_1 = \frac{MiRT}{A}\left(\frac{1}{\pi_2} - \frac{1}{\pi_1}\right) \qquad \text{Equation (I)}$$

$$\left(\frac{1}{\pi_2} - \frac{1}{\pi_1}\right) = \frac{A(L_2 - L_1)}{MiRT} \qquad \text{Equation (II)}$$

In Equations (I) and (II), M is the mass of solute in the osmotic chamber of a cylindrical implantable device, A is the cross sectional area of the cylindrical implantable device, and $L_1$ and $L_2$ are the initial and final positions of the back face of the compressible piston before and after displacement of the back face of the compressible piston under osmotic pressure. In Equation 1, the value of i is 1 for glucose and 2 for NaCl. As per the above equation, the displacement of the back face of the compressible piston is determined by measuring the osmotic pressure in the osmotic chamber. If the device functions correctly, the displacement of the back face of the compressible piston should be in accordance with Equation 1. If the osmotic pressure does not change in accordance with Equation 1, then the device has failed. The device could be deemed to have failed if there is a sudden change or no change at all in the osmotic pressure of the osmotic solution. If the device fails, the device will notify the user device and/or the caregiver via wireless communication, for example using a wireless personal area network, that the device has failed. On failure, an appropriate action such as removal of the implantable device or restarting or reconfiguring the device could be attempted.

An embodiment relates to a method, comprising receiving data comprising an osmotic pressure data from an implantable device comprising a pressure sensor, processing the osmotic pressure data to determine if the osmotic pressure data is within ±15% of an expected osmotic pressure data, and notifying a failure of the implantable device to a user and/or a health care provider if the osmotic pressure is not within ±15% with the expected osmotic pressure.

In an embodiment, the data comprises a displacement of a compressible piston of the implantable device, wherein the displacement equals a stroke length of the compressible piston times several doses discharged from the implantable device.

For a fully dissociated electrolyte such as NaCl, the molar conductivity is proportional to the number of ions. In this case, the electrical conductivity ($\pi$) of the solution for a given temperature and solute is: $\sigma=K\pi$, where K is a proportionality constant that depends on the ion mobility, charge, and average temperature of the solute.

Equation (II) can be written in terms of electrical conductivity as follows:

$$\left(\frac{K}{\sigma_2} - \frac{K}{\sigma_1}\right) = \frac{A(L_2 - L_1)}{MiRT} \qquad \text{Equation (III)}$$

All the materials used in making the AIMD should be FDA approved for medical devices. The dimensions the components will depend on the final design.

The term "Active wearable medical device" or "AWMD" refers to a compact, portable active wearable medical device designed to be worn or affixed on the body of a subject, which automatically or semi-automatically delivers precise doses of therapeutic agents (e.g., drugs, hormones, biologics) to a patient over a prescribed period. It typically includes a drug chamber, a pumping mechanism, and one or more delivery interfaces (such as a catheter, microneedles, or infusion set) that enable transdermal, subcutaneous, or intradermal administration of the drug.

The term "fluid chamber" refers to an enclosed chamber or a compartment that stores a fluid (e.g., liquid) to support osmosis. It is a reservoir containing the fluid and configured to deliver the fluid to the osmotic chamber via a semipermeable membrane. The fluid chamber is typically made from biocompatible materials and is fluidically connected to the drug delivery mechanism (e.g., a pump, microfluidic channel, or delivery port). It may be rigid, flexible, or expandable depending on the design of the device.

As used herein, the term "channel" refers to a defined fluidic pathway or conduit. The channel could guide the flow of the drug formulation from one component (e.g., drug chamber or pump) to another (e.g., delivery interface such as a microneedle, catheter, or nozzle) or a body of a mammal. The channel could ensure controlled and directed movement of the drug and may be part of a microfluidic system for precise dosing.

The term "fluidically coupled" refers to that two or more components in a system are connected in such a way that a fluid (e.g., liquid drug, gas, or biological fluid) can flow or be transmitted between them, either directly or through intermediate conduits such as tubes, channels, or valves. Fluidically coupled components enable controlled transfer of fluid, such as from a drug chamber to a pump, and from the pump to a delivery interface (e.g., microneedle or catheter).

The term "expandable elastomeric bladder" refers to a flexible, stretchable fluid-holding component made from elastomeric (rubber-like) material that can expand to store a fluid (e.g., a liquid drug) and contract to release it. It is used in wearable drug delivery systems to provide a passive or semi-passive pumping mechanism based on the elastic recoil of the material.

The term "rigid reservoir" refers to a non-deformable, fixed-volume container used to store a liquid or fluid formulation (e.g., a drug) within a medical or drug delivery device. Unlike flexible or expandable reservoirs, a rigid reservoir does not change shape or volume as fluid is filled or dispensed. The rigid reservoir enables diffusion of the fluid across the semipermeable membrane to dissolve an osmotic agent in the osmotic chamber and generate an osmotic gradient to drive the piston.

The term "Hydrogel reservoir" refers to a storage component in a drug delivery device that contains a hydrogel. The hydrogel acts as both a drug carrier and a release medium, enabling controlled release of the drug over time through diffusion, swelling, or degradation. The hydrogel releases the fluid over time to enable the passive ingress flow of the fluid to the osmotic chamber from the Hydrogel reservoir.

The term "microfluidic reservoir" refers to a small-volume chamber that stores fluid within a microfluidic architecture. It is typically fabricated using precise micro-scale techniques and biocompatible materials.

The term "Integrated Flow Restrictor" refers to a built-in microstructure (e.g., a narrow channel, porous membrane, or valve) that resists fluid flow to regulate the delivery rate. This restrictor may be passive (based on geometry or material properties) or active (responding to pressure, temperature, etc.)

The term "catheter" refers to a conduit to transport drugs from a reservoir or pump to a targeted internal location such as a vein, artery, organ, or body cavity.

The term "Targeted administration" refers to the precise delivery of a drug or therapeutic agent to a specific tissue, organ, cell type, or site within the body, rather than systemic distribution. The goal is to maximize therapeutic effects at the desired site while minimizing side effects elsewhere.

The term "active operated chamber" refers to a fluid chamber or compartment within a drug delivery device that dispenses its contents using an external or internal energy source or actuation mechanism, rather than relying solely on passive forces like gravity or elastic recoil.

The term "passive operated chamber" refers to a fluid chamber or compartment within a drug delivery device that dispenses its contents without the use of active or powered components, relying instead on inherent physical forces such as gravity, elastic recoil, osmotic pressure, or capillary action to drive fluid flow.

The term "biocompatible material" refers to any substance—natural or synthetic—that is compatible with living tissue and does not cause harmful effects (such as toxicity, inflammation, or immune rejection) when in contact with the body or bodily fluids, either temporarily or over extended periods.

The term "dissolvable material" refers to substance that is capable of breaking down and going into solution when exposed to a specific solvent—typically water or bodily fluids—within a defined period. The dissolvable materials are used to release therapeutic agents or eliminate the need for removal of the device or its components.

The term "plurality of drug chambers" refers to two or more separate compartments or chambers within a drug delivery device, each capable of storing and/or delivering a drug formulation. These chambers may contain the same drug for redundancy or extended dosing, or different drugs for combination therapies or sequential administration.

The term "sequential discharge" refers to the controlled, stepwise release of fluids or drug formulations from two or more drug chambers, reservoirs, or delivery elements in a predetermined order over time. It is commonly used to achieve multi-phase therapy, timed release, or layered dosing.

The term "combination of discharge" refers to the coordinated release of fluids or drug formulations from multiple chambers or sources, wherein the discharges may occur simultaneously, sequentially, intermittently, or in overlapping patterns, depending on therapeutic requirements or device programming.

The term "real-time imaging and navigation guidance device" refers to a medical system or tool that captures, processes, and displays visual data continuously or near-instantaneously to assist clinicians or robots in locating, targeting, and guiding instruments or therapies within the body during diagnostic or interventional procedures.

The term "attachment component" refers to a structural or functional element of a device that enables it to be secured, mounted, or affixed to another object or surface-such as a user's body, clothing, or another medical device.

An embodiment relates to an active wearable medical system configured for controlled and sustained release of therapeutic agents through the skin. The system comprises a drug pumping device comprising a compressible piston, a drug outlet, a fluid chamber containing a fluid (e.g., water) to support osmosis within the drug pumping device, a microfluidic channel fluidically connected to the drug delivery outlet, a plurality of microneedles fluidically connected to the microfluidic channel for drug delivery into the skin, and an attachment component for securing the system to the skin. The attachment component can be one of an adhesive layer, a mechanical fastener, a wearable strap, a wearable band, or a skin micro-anchor. The drug pumping device may be one of a flat shape, a tubular shape, a cylindrical shape, a disc shape, a capsule shape, a coil shape, a sheet shape, a film shape, etc.

Figure 11A:
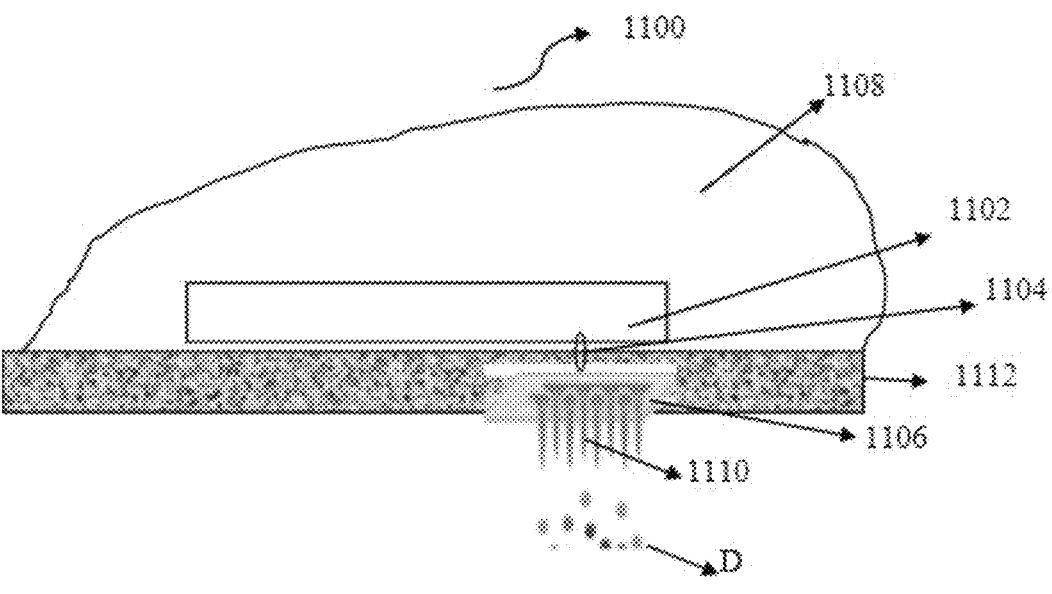
FIG. 11A and FIG. 11B illustrate a schematic representation of a system comprising an active wearable medical device, according to one or more embodiments.
Figure 11B:
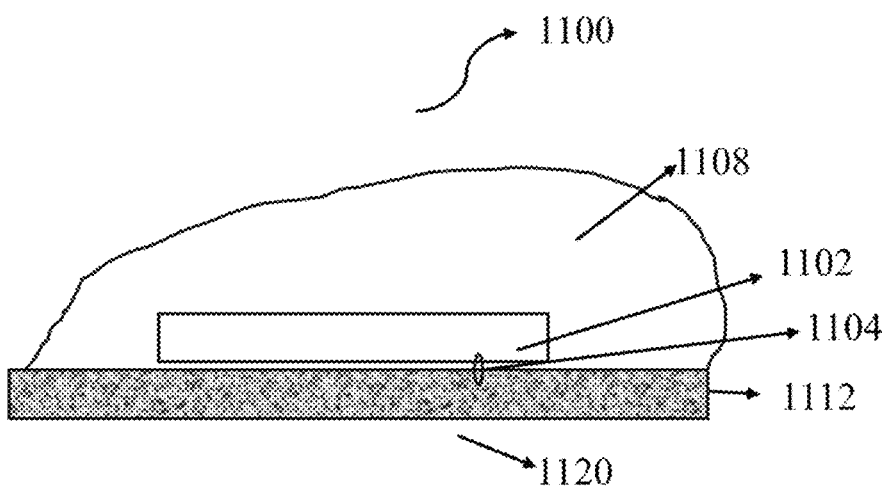

FIG. 11A illustrates a schematic representation of a drug delivery system 1100 comprising a drug pumping device 1102. The drug pumping device 1102 comprises a permeability module, a compressible piston, a drug chamber, a valve module, a sensor module, an electronic module and a machine learning model. Without limitation, positioning of modules, part or other components in drug pumping device 1102 could be arranged in a fashion as described in one or more embodiments of this disclosure. The drug pumping device 1102 comprises a drug outlet 1104, positioned to ensure uniform flow of drug into a microfluidic distribution channel 1106. A fluid chamber 1108, containing a fluid (e.g., water), supports an osmotic gradient that generates osmotic pressure. This osmotic pressure actuates a piston within the drug pumping device 1102, which displaces the drug D from a drug chamber through an electronically controlled valve module. The valve module permits one-way drug flow based on real-time displacement data from a sensor module (not shown). The drug pumping mechanism uses osmotic pressure to drive a compressible piston that delivers medication from a drug chamber through a controlled valve and channel. Fluid from a reservoir enters an osmotic chamber via a semipermeable membrane, where it interacts with an osmotic agent to generate pressure. This pressure deforms and displaces the piston, which pushes the drug out through one or more outlets when the valve is opened, enabling precise, wearable, and non-invasive drug delivery. The microfluidic distribution channel 1106 is fluidically connected to the drug outlet 1104 and to a plurality of microneedles 1110, which enable precise and uniform transdermal drug delivery. Each microneedle 1110 is designed to penetrate the stratum corneum without reaching pain receptors, allowing painless administration. The microfluidic distribution channel 1106 and microneedles 1110 may be fabricated from biocompatible materials such as silicon, polymers, or metals. An adhesive layer 1112 is disposed on the underside of the system. The adhesive layer 1112 comprises a biocompatible adhesive backing with optional perforations for breathability, ensuring stable contact during drug administration. FIG. 11B illustrates the Active wearable medical system of FIG. 11A wherein the drug outlet is fluidically connected to catheter 1120 for targeted drug administration to a specific anatomical site.

In an embodiment, the Active wearable medical system comprises an expandable elastomeric bladder configured as a fluid chamber for storing fluid (e.g., water) or another biocompatible aqueous medium. The bladder is in fluidic communication with a semipermeable membrane that separates it from the osmotic chamber of the drug pumping device. As fluid pressure is applied—either pre-filled or generated passively during wear—the bladder expands and gradually releases fluid (e.g., water) across the semipermeable membrane. This water mixes with the osmotic agent in the osmotic pump, generating pressure that drives a piston mechanism to deliver the drug through microneedles into the skin.

Figure 12A:
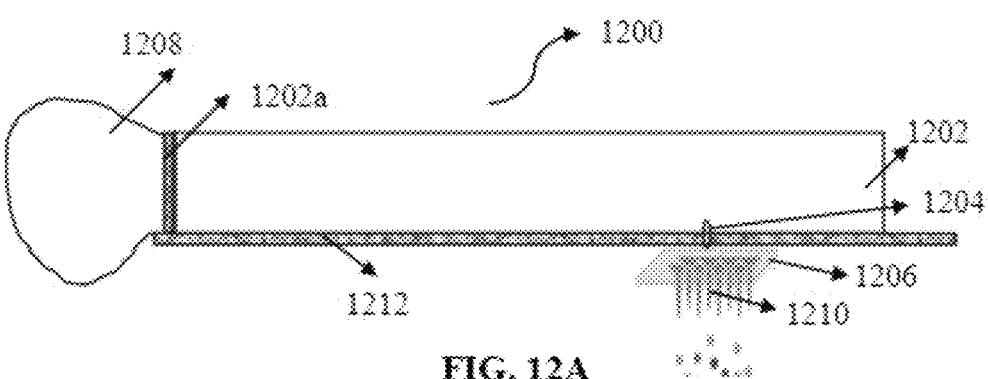
FIG. 12A and FIG. 12B illustrate an Active wearable medical system incorporating an expandable elastomeric bladder as the fluid chamber, according to one or more embodiments.
Figure 12B:
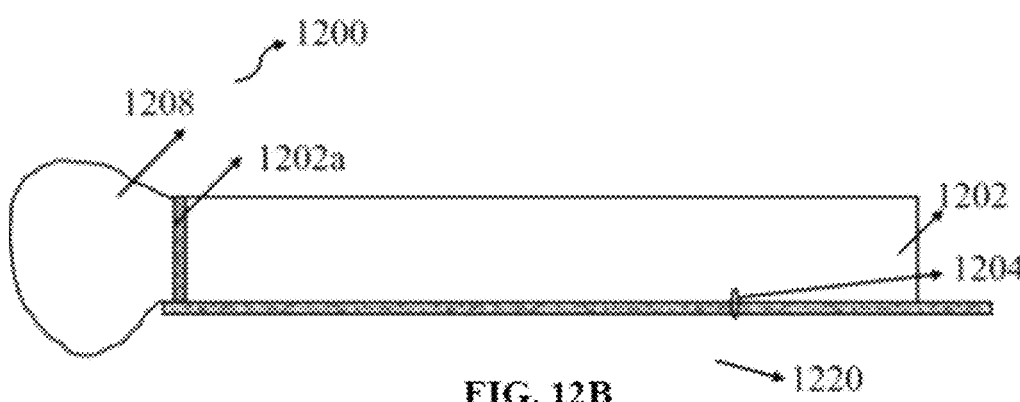

FIG. 12A illustrates a wearable transdermal drug delivery system 1200 incorporating an expandable elastomeric bladder as the fluid chamber 1208. The bladder, in fluidic contact with a semipermeable membrane 1202a of the drug pumping device 1202, stores a biocompatible aqueous medium. The bladder may be either actively operated or passively operated. The bladder may be passively operated via an elastic recoil. The bladder may be actively operated using sensors or controllers that regulates the outlet of the bladder. Upon activation, the fluid pressure is applied and the water is released across the membrane into the osmotic pump, generating osmotic pressure that actuates a piston. The piston drives the drug through a valve module and delivery outlet 1204 into a microfluidic distribution channel 1206, which is connected to a plurality of microneedles 1210 for drug delivery into the skin. FIG. 12B illustrates the Active wearable medical system of FIG. 12A comprising an expandable elastomeric bladder, wherein the drug outlet is connected to catheter 1220 for localized drug delivery.

Another embodiment comprises a rigid fluid reservoir, such as a molded polymer or metal container, configured to passively store water. The reservoir is fluidically connected to the osmotic chamber via a flow-regulating semipermeable membrane or capillary channel that allows controlled diffusion of water. As the osmotic agent dissolves, water is drawn from the rigid reservoir, generating an osmotic gradient that activates the osmotic pump. This design ensures mechanical stability and consistent osmotic flow for controlled drug delivery.

Figure 13A:
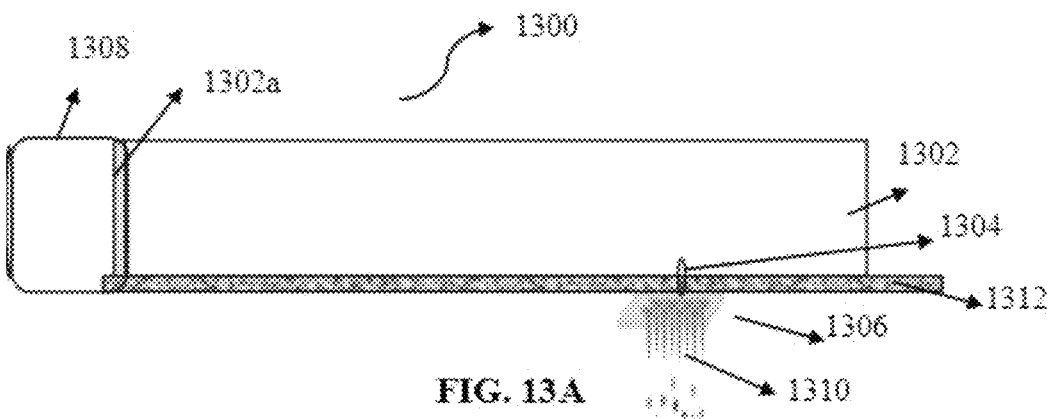
FIG. 13A and FIG. 13B illustrate an Active wearable medical system incorporating a rigid reservoir as the fluid chamber, according to one or more embodiments.
Figure 13B:
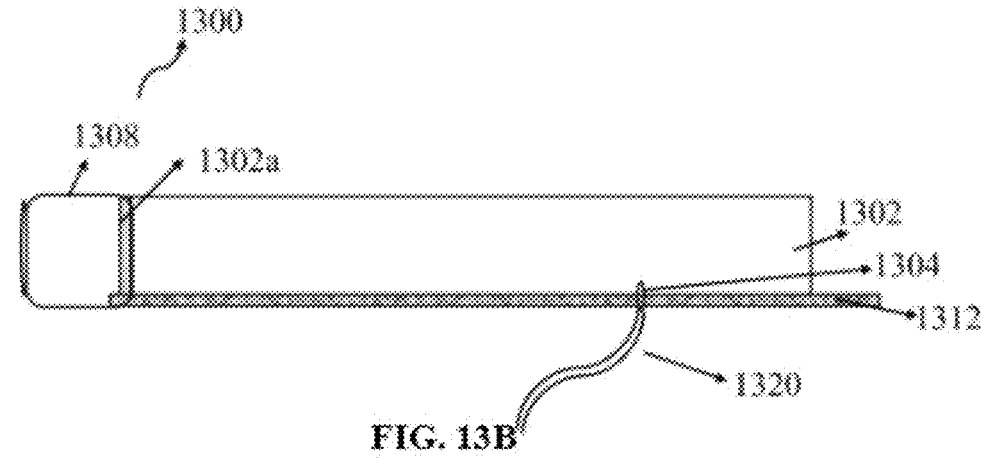

FIG. 13A shows an active wearable medical system 1300 comprising a rigid fluid reservoir 1308 made of molded polymer or metal. The reservoir is fluidically connected to the osmotic chamber of a drug pumping device 1302 via a semipermeable membrane 1302a. As the osmotic agent dissolves, osmotic pressure builds and actuates a piston, which displaces the drug through a valve module and delivery outlet 1304 into a microfluidic distribution channel 1306 connected to microneedles 1310 for transdermal delivery. An adhesive layer 1312 secures the system to the skin. FIG. 13B illustrates the Active wearable medical system of FIG. 13A incorporating a rigid fluid reservoir, wherein the drug outlet is connected to catheter 1320 for directing the drug to a selected tissue region.

A further embodiment utilizes a hydrogel-based fluid chamber, wherein a pre-hydrated, biocompatible hydrogel matrix serves as a solid-state water source. The hydrogel is positioned adjacent to a semipermeable membrane that interfaces with the osmotic chamber. Over time, water is gradually released from the hydrogel and diffuses through the membrane, dissolving the osmotic agent and generating osmotic pressure to actuate the piston and enable drug delivery. This configuration reduces the presence of free liquid, making it suitable for compact, flexible, and patch-style systems.

Figure 14A:
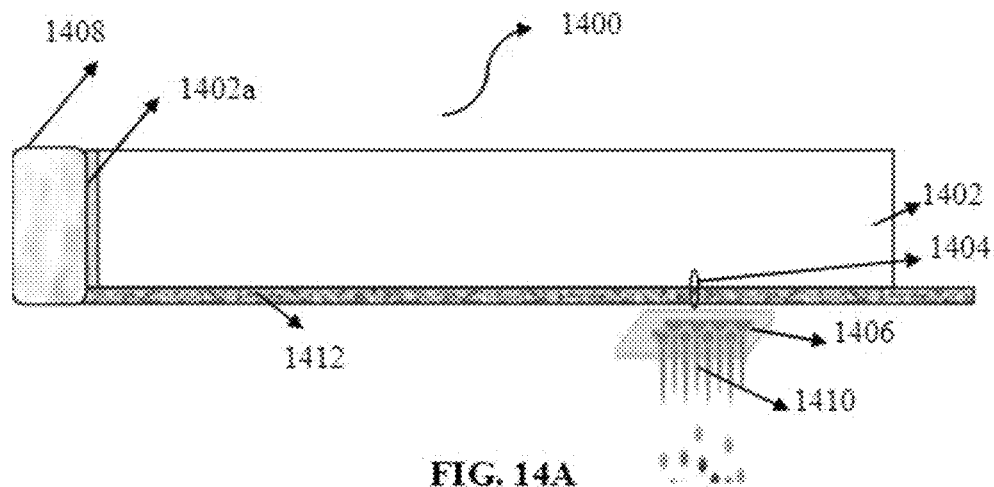
FIG. 14A and FIG. 14B depict an active wearable medical system incorporating a Hydrogel reservoir as the fluid chamber, according to one or more embodiments.
Figure 14B:
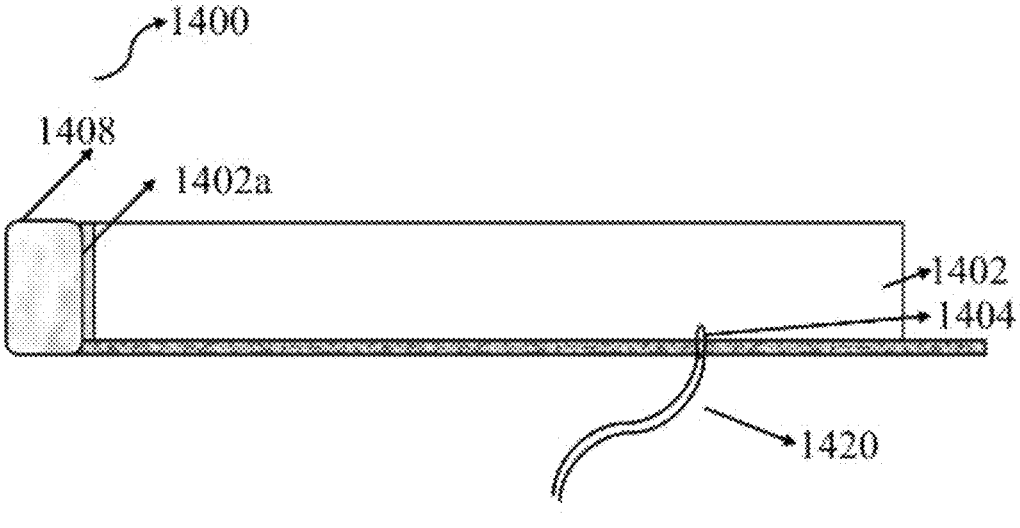

FIG. 14A depicts an active wearable medical system 1400 utilizing a hydrogel-based fluid chamber 1408. The hydrogel matrix is pre-hydrated and biocompatible, and positioned adjacent to a semipermeable membrane 1402a of the drug pumping device 1402. Water released from the hydrogel activates the osmotic pump, generating pressure that actuates a piston to displace the drug through a valve module and delivery outlet 1404 into a microfluidic distribution channel 1406. The channel leads to microneedles 1410 for painless transdermal delivery. An adhesive layer 1412 ensures skin attachment and breathability. FIG. 14B illustrates the Active wearable medical system of FIG. 14A incorporating a hydrogel-based fluid chamber, wherein the drug outlet is fluidically connected to catheter 1420 for targeted therapeutic delivery.

In another embodiment, the system comprises a microfluidic fluid chamber configured to contain water and integrated with a flow restrictor, such as a nanochannel, porous membrane, or precision orifice. The restrictor interfaces with a semipermeable membrane leading to the osmotic chamber of a drug delivery pump, delivering water at a controlled rate to sustain osmotic pressure over an extended period. This configuration enables precise control of fluid delivery matched to the expected osmotic uptake rate and dosing schedule.

FIG. 15A illustrates an active wearable medical system 1500 comprising a microfluidic fluid chamber 1508 with an integrated flow restrictor. The restrictor, which may include a nanochannel, porous membrane, or precision orifice, is in fluidic communication with a semipermeable membrane 1502a of a drug pumping device 1502 leading to the osmotic chamber. The resulting osmotic pressure actuates a piston of the drug pumping device 1502 (not shown in the figure), which drives drug flow through a valve module (not shown in the figure) and delivery outlet 1504 into a microfluidic distribution channel 1506. The drug is subsequently delivered via microneedles 1510 into the skin. An adhesive layer 1512 secures the system during use. FIG. 15B illustrates the Active wearable medical system of FIG. 15A comprising a microfluidic reservoir with flow restrictor, wherein the drug outlet is connected to catheter 1520 to facilitate precise regional drug administration.

An embodiment relates to a system for targeted drug administration. The system comprises a catheter and a drug pumping device configured to deliver a therapeutic agent through the catheter. The drug pumping device can be one of an active implantable medical device or an active wearable medical system that comprises a drug chamber containing a drug formulation, an osmotic pump mechanism comprising an osmotic chamber, a semipermeable membrane, and an actuator (e.g., a piston) that responds to osmotic pressure to displace the drug. The drug delivery outlet is fluidically connected to a catheter configured to route the drug to a specific anatomical site, such as a blood vessel, organ, or localized tissue region. The catheter may comprise an implantable, flexible microcatheter made from biocompatible materials such as polyurethane or silicone and may include one or more delivery ports or diffusers at its distal end to facilitate uniform drug dispersion. This configuration enables localized or regional delivery, enhancing therapeutic efficacy and minimizing systemic exposure.

FIG. 16 shows a drug delivery system 1600 configured for targeted drug administration via a catheter. The system comprises an active wearable medical system 1602. The delivery outlet 1604 of the Active wearable medical system 1602 is fluidically connected to a catheter 1606 configured to deliver the drug D to a targeted anatomical site (e.g., liver). The catheter 1606 may comprise delivery ports or diffusers at its distal end. An adhesive or anchoring layer 1612 may be included to maintain system position.

Note that the flowchart and the suggested time limits and parameters are meant to be exemplary, and that there could be other measures or criteria used in order to maximize safety and accuracy.

Definitions and General Techniques

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent, or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present disclosure may be embodied in other specific forms without departing from its spirit or characteristics. The embodiments described are to be considered in all respects only as illustrative and not restrictive. The scope of the disclosure is, therefore, indicated by the appended claims rather than by the foregoing description. All changes which come within the meaning and range of equivalents of the claims are to be embraced within their scope.

As defined herein, "approximately" or "about" can, in some embodiments, mean within plus or minus ten percent of the stated value. In other embodiments, "approximately" or "about" can mean within plus or minus five percent of the stated value. In further embodiments, "approximately" or "about" can mean within plus or minus three percent of the stated value. In yet other embodiments, "approximately" or "about" can mean within plus or minus one percent of the stated value.

Unless otherwise defined herein, scientific and technical terms used in connection with the present disclosure shall have meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present disclosure are generally performed according to conventional methods well-known in art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The following terms and phrases, unless otherwise indicated, shall be understood to have the following meanings.

The term "fixed volume" refers to when discharge of a drug volume from the implantable device is almost the same or within an allowed variation of up to ±25% of the said volume in the repeated dose cycles. In an embodiment, preferably the allowed variation is up to ±20% of the said volume, more preferably allowed variation up to ±15%, and further more preferably up to ±10% or less of the said drug discharge volume.

The term "analyte" designates without limitation a substance or chemical constituent in a biological fluid (for example, blood, interstitial fluid, cerebral spinal fluid, lymph fluid or urine) that can be analyzed. Analyte can include naturally occurring substances, artificial substances, metabolites, and/or reaction products.

The term "power source" refers to a component that could provide necessary energy to operate a detector component and communication circuitry. Typically, this is a battery housed within the system's case.

The term "adhesive" is any non-metallic substance applied to one or both surfaces of two separate items that binds them together. Adhesives are also known as glue, cement, mucilage, or paste. There are a large number of adhesive types for various applications. They may be classified in a variety of ways depending on their chemistries (e.g. epoxies, polyurethanes, polyimides), their form (e.g. paste, liquid, film, pellets, tape), their type (e.g. hot melt, reactive hot melt, thermosetting, pressure sensitive, contact, etc.), or their load carrying capability (structural, semi-structural, or non-structural). Any type of adhesive comes under the scope of the disclosure.

The term "physiological parameters" includes, but is not limited to, subject body temperature, subject heart rate, subject heart rate variability, subject blood gas levels, subject metabolic rate, subject respiration rate, subject blood analyte levels, subject blood pressure, subject pulse pressure, etc.

In an embodiment, the invention measures the value of a physiological parameter of a subject (e.g., state of metabolism, state of lowered metabolism, state of rest, etc.), including obtaining the data using sensors attached to the subject. A time-dependent relationship function could be applied on the value of the obtained physiological parameter of the subject at a particular time-of-day using at least one processor to determine a real-time value and/or predict the future physiological parameter of the subject for the given condition.

The term "water-proof safeguards" or "waterproofing agent" or the like refers to materials such as but not limited to sealant additives, resins, etc., that repel water and prevent damage to the underlying substrate beneath the waterproofing material. In an embodiment, waterproofing agent may include but not limited to application of beeswax, waterproofing spray, or mink oil, lignin coating, ethylene propylene diene monomer EPDM rubber, hypalon, polyvinyl chloride etc.

The term "app" or "application" as used herein is an application (app) software program within a computer program designed to help people perform an activity. Depending on the activity for which it was designed, an application performs a task. For example, an app could manipulate text, numbers, audio, graphics, and a combination of these elements. In an embodiment, some applications packages focus on a single task such as word processing, etc. In some embodiments, some applications are integrated software including several applications. In an embodiment, apps could also be built for mobile platforms.

The term "remote device" refers to a device that receives data from a detector component and/or a monitoring system. The remote device may receive data from a sensor. The remote device comprises a processor, memory, and its own communication circuitry and power source to process the data.

The term "adjustable threshold(s)" refers to a predefined value at which the application can be set to trigger alerts when chemicals are detected in specific concentrations.

The term "compressible piston" refers to an object that changes its volume by a given volume when it changes shape from a compressed configuration to an uncompressed configuration and can move longitudinally as a whole in a tube. The term, "volume" of the compressible piston relates to a volume enclosed within close between 2 opposite ends of the pistons.

In an aspect this item relates to a system comprising an implantable device having from 3 mm to 6 mm diameter tubular form, wherein the implantable device is inserted subcutaneously and non-surgically by an injector device in a human body via an incision; the implantable device comprising a casing comprising a pump, a piston, a drug chamber comprising a drug, and an opening for release of the drug from the implantable device into a body of a subject; wherein the implantable device is configured to be located in a subcutaneous region within the body of the subject during delivery of the drug into the body of the subject; wherein the implantable device is configured to deliver multiple doses of the drug within the body of the subject with a dose-to-dose variation of ±25% or less by volume; and wherein the implantable device further comprises power supply and electronics; and wherein the implantable device is configured to notify the subject in case of failure of the implantable device.

In an embodiment, the implantable device comprises: a casing that is substantially tubular and has at least a first end and a second end opposite to the first end, a semipermeable membrane plug at or near the first end, a first chamber comprising an osmotic agent, wherein one wall of the first chamber comprises the semi-permeable plug, a second chamber comprising a drug, a third chamber comprising a flow switch and at least one drug delivery orifice, a piston separating the first chamber and the second chamber, a fourth chamber comprising an electronic control unit and a source of energy, wherein an osmotic pressure is configured to be built on ingress of a liquid into the first chamber through the semipermeable membrane plug that displaces the piston towards the second chamber; and wherein the flow switch and the osmotic pressure together regulate a release of the drug from the at least one drug orifice, such that the flow switch in its ON state allow the drug to be released from the at least one drug orifice and in its OFF state stops release of the drug from at least one drug orifice, wherein the implantable device further comprises an electro-mechanical actuator to control ON/OFF state of the flow switch based on a displacement of the piston.

In an embodiment, the electro-mechanical actuator comprises an electroactive polymer. In an embodiment, the electro-mechanical actuator comprises a piezo element.

In an embodiment, the fourth chamber further comprises a piston position determination module. In an embodiment, the piston position determination module is configured to determine a real-time positioning of the piston. In an embodiment, the piston determination module is based on pressure measurement, conductance measurement, resistance measurement, pressure measurement, reflection measurement, capacitance measurement, impedance measurement, radical measurement, image-based measurement, laser measurement, SONAR based measurement, ultrasound measurement, time of flight measurement or combinations thereof. In an embodiment, the piston position determination module interacts with one or more electro-mechanical actuator to control an ingress flow of the liquid inside the implantable device and an egress flow of the drug outside the implantable device.

In an embodiment, the implantable device further comprises a sensor. In an embodiment, the implantable device further comprises one or more biosensors. In an embodiment, one or more biosensors is configured to either detect a biomarker present in a human or an animal body, a concentration of the drug release from the implantable device and/or a bio-chemical parameter of the human or an animal body. In an embodiment, the biosensor is a wearable device. In an embodiment, the semi-permeable plug comprises cellulose acetate. In an embodiment, a rate of ingress of the liquid in the implantable is in a range of about 0.5 μl/min to 2 μl/min.

In an embodiment, a pressure sensor and/or a conductivity sensor present in the implantable device is configured to measure a displacement of the piston.

In an embodiment, the first chamber comprises the pressure sensor and/or the conductivity sensor. In an embodiment, an electric circuit connects a sensor and the actuator to electronic control unit in the fourth chamber to control the flow of the drug from the implantable device.

In an embodiment, an egress rate of the drug release is substantially same as an ingress rate of the liquid. In an embodiment, the implantable device is biocompatible.

An aspect of the disclosure relates to a system comprising a software implemented module and an implantable device comprising: a casing that is substantially tubular and has at least a first end and a second end opposite to the first end, a semipermeable membrane plug at or near the first end, a first chamber comprising an osmotic agent, wherein one wall of the first chamber comprises the semi-permeable plug, a second chamber comprising a drug, a third chamber comprising a flow switch and at least one drug delivery orifice, a piston separating the first chamber and the second chamber, a fourth chamber comprising an electronic control unit and a source of energy, and one or more sensors to detect amount of the drug released from the implantable device; wherein an osmotic pressure is configured to be built on ingress of a liquid into the first chamber through the semipermeable membrane plug that displaces the piston towards the second chamber, which further pushes the drug present in the second chamber to be release from the at least one drug orifice, and wherein one or more sensors interact with the software implemented module to control the flow of the drug released from the implantable device.

In an embodiment, the system is configured to allow interaction between a biosensor and a sensor to alter a drug release pattern from the implantable device in a body of a human or an animal. In an embodiment, the software implemented module comprises at least one of a data collection unit, a data processing unit, a prediction unit, and/or a dosage recommendation unit. In an embodiment, the software implemented module is configured to use an artificial intelligence algorithm to analyze data provided by the one or more sensors and/or biosensors and regulate a drug release pattern from the implantable device.

An aspect relates to a method comprising: receiving data from one or more sensors present on an implantable device, transmitting the data to one or more software implemented module, analyzing the data and providing an output, wherein the output regulates ingress of a liquid inside the implantable device through a semi-permeable plug present at or near first end, and egress of a drug stored in the implantable device through one or more drug orifices into a body of a human and an animal.

In an embodiment, the one or more software implemented module comprises at least one of a data collection unit, a data processing unit, a prediction unit, and/or a dosage recommendation unit. The one or more sensors collect data on a biochemical parameter of the body of the human and the animal in which the implantable device is implanted. The data collection unit is configured to collect the data from the one or more sensors and send the data further to the data processing unit. The data processing unit is configured to analyze a physiological condition of the body of the human and the animal in which the implantable device is implanted. The prediction unit is configured to utilize a machine learning algorithm to provide a drug dosing pattern according to the physiological condition of the body of the human and the animal.

In an embodiment, the method is configured to provide a personalized drug dosing pattern according to a physiological condition of the body of the human and the animal in which the implantable device is implanted.

An aspect relates to a system comprising: a body temperature stable drug formulation that ensures that the drug does not degrade within the body of the subject at a body temperature of the subject for at least 6 months; an implantable biosensor that provides real-time monitoring of a drug level and/or a health-related biomarker; and an artificial intelligence system that integrates and analyzes data to optimize drug delivery in real-time; wherein the system is configured to be an AI-based implantable drug delivery system. In an embodiment, the subject comprises a human being and the body temperature of the subject is in a range from 95° F. to 105° F.

In an aspect the disclosure relates to a device comprising a casing comprising: a first module comprising a semipermeable membrane plug; a second module comprising a pressure sensor; a third module comprising a piston and a drug reservoir chamber; and a fourth module comprising a flow switch and an electronics chamber comprising a power supply component; wherein the device is configured to be implanted subcutaneously by an injector device in a body of a subject via an incision; wherein the device is configured to deliver multiple doses of a drug within the body of the subject with a dose-to-dose variation of ±25% or less by volume; and wherein the device is configured to notify in case of anomaly in the device.

In an embodiment, the piston is movable. In an embodiment, the osmotic pressure is configured to be built on ingress of a liquid into the first chamber through the semi-permeable membrane plug that displaces the piston towards the drug reservoir chamber.

In an embodiment, the pressure sensor present in the device is configured to measure the displacement of the piston. In an embodiment, an egress rate of a drug release is substantially same as an ingress rate of the liquid via the semipermeable membrane plug. In an embodiment, the fourth module comprises a third chamber comprising the flow switch and at least one drug delivery orifice for release of the drug from the device into the body of the subject. In an embodiment, the flow switch is an ON-OFF flow switch. In an embodiment, the ON-OFF flow switch comprises a relief valve, a push rod, and a stepper motor. In an embodiment, an electronic signal from the electronics chamber is transmitted to the first chamber, second chamber and/or third chamber via an electric circuit. In an embodiment, the electric circuit is printed on an inner surface of the casing of the device.

In an embodiment, the device is configured to be located in a subcutaneous region within the body of the subject during delivery of the drug into the body of the subject.

An aspect relates to a device comprising a casing comprising: a first module comprising a semipermeable membrane plug; a second module comprising a pressure sensor; a third module comprising a dual piston assembly and a drug reservoir chamber; and a fourth module comprising a flow switch and an electronics chamber comprising a power supply component; wherein the device is configured to be implanted subcutaneously by an injector device in a body of a subject via an incision; wherein the device is configured to deliver multiple doses of a drug within the body of the subject with a dose-to-dose variation of ±25% or less by volume; and wherein the device is configured to notify in case of anomaly in the device.

In an embodiment, the dual piston assembly comprises a spring of a fixed compressed length that is connected with a first piston from a first end and with a second piston from a second end. In an embodiment, dual piston assembly further comprises a string. In an embodiment, the dual piston assembly is enclosed within a bellow. In an embodiment, the dual piston assembly comprises a foam cylinder encapsulated by the bellow.

An embodiment relates to a device comprising a casing comprising: a first module comprising a hollow fiber membrane plug; a second module comprising a pressure sensor; a third module comprising a piston and a drug reservoir chamber; and a fourth module comprising a flow switch, an electronics and power supply chamber; and wherein the device is configured to be implanted subcutaneously by an injector device in a body of a subject via an incision; wherein the device is configured to deliver multiple doses of the drug within the body of the subject with a dose-to-dose variation of ±25% or less by volume; and wherein the device is configured to notify in case of anomaly in the device.

In an embodiment, the hollow fiber membrane plug comprises a plurality of hollow fiber forward osmosis membranes bundled together, wherein the hollow fiber forward osmosis membranes are thin and flexible. In an embodiment, the hollow fiber forward osmosis membrane comprises an inlet end facing a first end of the device and an outlet facing the pressure sensor. In an embodiment, outside of the plurality of hollow fiber forward osmosis membranes is a glucose solution. In an embodiment, a water ingress from the inlet end from the body causes pushing out of an equal volume of the glucose solution from the first module through the outlet a second end of the first module.

In an aspect a device comprising a casing comprising: a first module comprising a hollow fiber membrane plug; a second module comprising a pressure sensor; a third module comprising a dual piston assembly and a drug reservoir chamber, wherein the dual piston assembly comprises a spring of a fixed compressed length that is connected with a first piston from a first end and with a second piston from a second end; and a fourth module comprising a flow switch and an electronics chamber comprising a power supply component; wherein the device is configured to be implanted subcutaneously by an injector device in a body of a subject via an incision; wherein the device is configured to deliver multiple doses of the drug within the body of the subject with a dose-to-dose variation of ±25% or less by volume; and wherein the device is configured to notify in case of anomaly in the device.

In an aspect, the disclosure relates to a system comprising a device comprising a casing further comprising a first module comprising a semipermeable membrane plug, a second module comprising a pressure sensor, a third module comprising a piston and a drug reservoir chamber, and a fourth module comprising a flow switch and an electronics chamber comprising a power supply component; and a catheter-like tube connected to the drug reservoir of the device to deliver a drug anywhere in a body of a subject away from the device; wherein the system is configured to be implanted subcutaneously; wherein the system is configured to deliver multiple doses of the drug within the body of the subject with a dose-to-dose variation of ±25% or less by volume; and wherein the system is configured to notify in case of anomaly in the device.

In an embodiment, the catheter-like tube comprises a secure connector at one end for connecting to the device and wherein the secure connector permanently attaches the catheter-like tube to the device making the catheter-like tube and the device integral with one another. In an embodiment, the catheter-like tube detachably attached to the device. In an embodiment, the catheter-like tube delivers the drug to a target area of interest in the body. In an embodiment, the catheter-like tube comprises a flexible loop along a length of the catheter-like tube to minimize a force generated due to detaching or reattaching the catheter-like tube to the device. In an embodiment, a drug delivery end of the catheter-like tube comprises one of a "mist" outlet, a "jet" outlet, and a "rectangular opening" outlet. In an embodiment, the drug delivery end of the catheter-like tube comprises one or more hooks to attach directly to a tumor within the body. In an embodiment, the catheter-like tube comprises a balloon portion along a length of the catheter-like tube, wherein the balloon portion is configured to increase a capacity of the catheter-like tube and provide additional axial flexibility.

An aspect of the disclosure relates to a device comprising: a first module comprising one of a flat fiber membrane or a hollow fiber forward osmosis membrane, a second module comprising a pressure sensor, a third module comprising a chamber with filled with saline or glucose and one of a single piston or a dual piston-spring assembly, a fourth module comprising an electronics chamber comprising a power supply component, and a catheter filled with drug, wherein the device is configured to be implanted subcutaneously; wherein the device is configured to deliver multiple doses of a drug within a body of a subject with a dose-to-dose variation of ±25% or less by volume; and wherein the device is configured to notify in case of anomaly in the device.

An aspect of the disclosure relates a device comprising a casing comprising: a first module comprising one of a flat fiber membrane or a hollow fiber forward osmosis membrane, a second module comprising a pressure sensor, a third module comprising a pressure chamber and a movable plug, and a fourth module comprising electronics and an actuator, wherein the device is configured to be implanted subcutaneously within a body of a subject; wherein the device is configured to deliver multiple doses of a drug within the body of the subject with a dose-to-dose variation of ±25% or less by volume; and wherein the device is configured to notify in case of anomaly in the device.

In an embodiment, the pressure chamber comprises a composition comprising water and Carbon di Oxide. In an embodiment, the movable plug covers a drug outlet on the casing, keeping the device in a closed configuration. In an embodiment, the actuator is designed to push the movable plug, thereby opening the drug outlet. In an embodiment, the opening of the drug outlet facilitates drug delivery into the body of the subject. In an embodiment, the device notifies the subject through a sensory signal. In an embodiment, the device notifies an external system by sending a notification message.

An aspect of the disclosure relates to a device, comprising: a) a permeability module comprising a semipermeable membrane at one of the device; b) an osmotic chamber comprising an osmotic solution; c) a sensor module comprising a sensor configured to monitor a physical parameter; d) a drug chamber comprising a drug; e) a piston assembly comprising a spring and at least one pair of pistons, wherein the piston assembly is sandwiched between the osmotic chamber and the drug chamber; f) a valve module to allow unidirectional flow of the drug from the drug chamber to outside the device through one or more drug outlet orifices present within the device; g) an electronic module; and h) a power supply module; wherein on operation of the power supply module of the device: (i) the permeability module allows inflow of a fluid from the semipermeable membrane into the osmotic chamber to establish an osmotic pressure; (ii) the electronic module configured to switch on and off the valve module as per a predetermined program set within the device to regulate flow of the drug from the drug chamber.

In an embodiment, the device is substantially tubular such that the device is configured to be implanted subcutaneously in a human body. In an embodiment, a sensor module detects movement of the piston assembly.

An aspect of the disclosure relates to a system comprising an implantable device and a patch configured to attach over a human body; wherein the implantable device comprises: a) a permeability module comprising a semipermeable membrane at one of the device; wherein the permeability module inside the human body allows inflow of a fluid from the semipermeable membrane into an osmotic chamber to establish an osmotic pressure; b) the osmotic chamber comprising an osmotic solution; c) a sensor module comprising a sensor configured to monitor a physical parameter; d) a drug chamber comprising a drug; e) a piston assembly comprising a spring and at least one pair of pistons, wherein the piston assembly is sandwiched between the osmotic chamber and the drug chamber; f) a valve module to allow unidirectional flow of the drug from the drug chamber to outside the device through one or more drug outlets or orifices present within the device; and g) an electronic module; h) a power supply module; wherein on a signal from the patch, the electronic module activates within the implantable device to regulate switch on and off the valve module as per a predetermined program set within the device to regulate flow of the drug from the drug chamber.

In an embodiment, the drug comprises an opioid antagonist. The opioid antagonist may be Naloxone. In an embodiment, the patch further comprises a biosensor to sense a biological parameter of the human body. In an embodiment, an opioid overdose detected by the biosensor in the human body directs the patch to send the signal to the electronic module of the device to allow discharge of the drug from the implantable device. In an embodiment, a wearable device in communication with the patch. In an embodiment, the wearable device is configured to send an emergency signal to a predestined location. In an embodiment, the emergency signal from the wearable device and the signal from the implantable device happen simultaneously. In an embodiment, the implantable device is implanted subcutaneously within the human body.

In one embodiment, the present disclosure relates to robotic surgical systems and methods for the robotic implantation of a drug delivery device implanted into a human body, and to alternative embodiments in which the drug delivery device is externally positioned on the patient's skin surface, with a transdermal catheter providing access to an internal target site for therapeutic delivery. The system comprises a robotic manipulator configured for minimally invasive surgical procedures to access a predetermined implantation site (e.g., specific anatomical site) within the body. The robotic manipulator may comprise a programmable, multi-jointed robotic arm capable of performing delicate dissection, pocket formation, and precise device placement under image-guided navigation.

In some embodiments, the system further comprises an implantable drug delivery device (AIMD) enclosed in a biocompatible housing, the housing containing an internal drug reservoir, a pumping mechanism associated electronic control circuitry, a power source, a catheter port, and optionally, a self-sealing refill port. In some embodiments, a flexible, biocompatible catheter is connected to the drug delivery device, the catheter being routed subcutaneously or through body tissue to deliver the therapeutic substance to a predetermined anatomical target, such as the intrathecal space, peritoneal cavity, intravascular system, or other tissue compartments. The catheter may be reinforced to resist kinking and may include additional features such as bacterial filters, check valves, and flow control regulators.

The robotic implantation method comprises a preoperative planning phase wherein patient-specific anatomical imaging (e.g., CT, MRI, or ultrasound) is utilized to identify an optimal implantation site and to plan the catheter route, avoiding critical anatomical structures. The robotic manipulator is then employed to gain minimally invasive access to the implantation region via small incisions and blunt tissue dissection. A subcutaneous or intraperitoneal pocket is then created robotically for receiving the drug delivery device housing. Following pocket creation, the implantable drug delivery device is delivered and positioned within the pocket, and the catheter is tunnelled and routed to the anatomical target site. The robotic system then secures the drug delivery device and catheter using sutures, adhesives, or mechanical anchors. Once the hardware is fixed in place, system integration is performed by connecting the device components and testing the device function, including delivery of a test bolus to confirm patency and proper placement. The incisions are then closed using minimally traumatic techniques such as fine suturing or tissue adhesives.

Robotic implantation offers numerous advantages, including enhanced precision of device and catheter placement, reduced tissue trauma due to controlled and delicate movements, and minimization of incision size. The programmable and automated nature of robotic operations also contributes to reproducibility, consistency, and a lower rate of complications compared to manual surgical techniques. Real-time intraoperative imaging and navigation further improve accuracy and safety. Collectively, these features result in reduced postoperative pain, accelerated patient recovery, and improved therapeutic outcomes.

In another embodiment, the drug delivery device is configured for external placement on the surface of the patient's skin, thereby obviating the need for surgical implantation of the device body. In this configuration, the system comprises an external drug delivery device adapted for skin attachment via medical-grade adhesive or mechanical fastening means. The external drug delivery device houses a drug reservoir, a pumping mechanism (peristaltic or metering type), electronic control circuitry, a power source, and an interface for refilling, programming, or monitoring. A transdermal catheter assembly connects to the external drug delivery device, and the catheter is inserted through the skin and routed to a desired subcutaneous, intramuscular, or intravascular site. The catheter is secured in place using a securement mechanism that may include mechanical anchors, adhesive pads, or antimicrobial dressings.

In some embodiments, operation of the external drug delivery device comprises programmed dosing via the pump, delivering medication directly to the target site through the transdermal catheter. The system may incorporate sensors to monitor flow rate, detect occlusion or leakage, and verify reservoir levels. The external configuration allows for non-invasive refilling, device replacement, or reprogramming, thereby reducing the need for follow-up surgical intervention. This embodiment provides benefits such as ease of use, simplified maintenance, and reduced risk of systemic infection, particularly at the catheter entry point, due to securement and barrier protection.

An exemplary embodiment of the system may comprise the following integrated components: (i) a robotic manipulator system for surgical access and device handling; (ii) an implantable or externally placed drug delivery device as described; (iii) a catheter for targeted drug delivery; (iv) an imaging and navigation system utilizing modalities such as fluoroscopy, ultrasound, or CT for intraoperative and preoperative guidance; (v) fixation and anchoring mechanisms including sutures, adhesives, or mechanical components for securing the drug delivery device and catheter; and (vi) optional feedback sensors for real-time monitoring of drug delivery parameters and device status.

Figure 17:
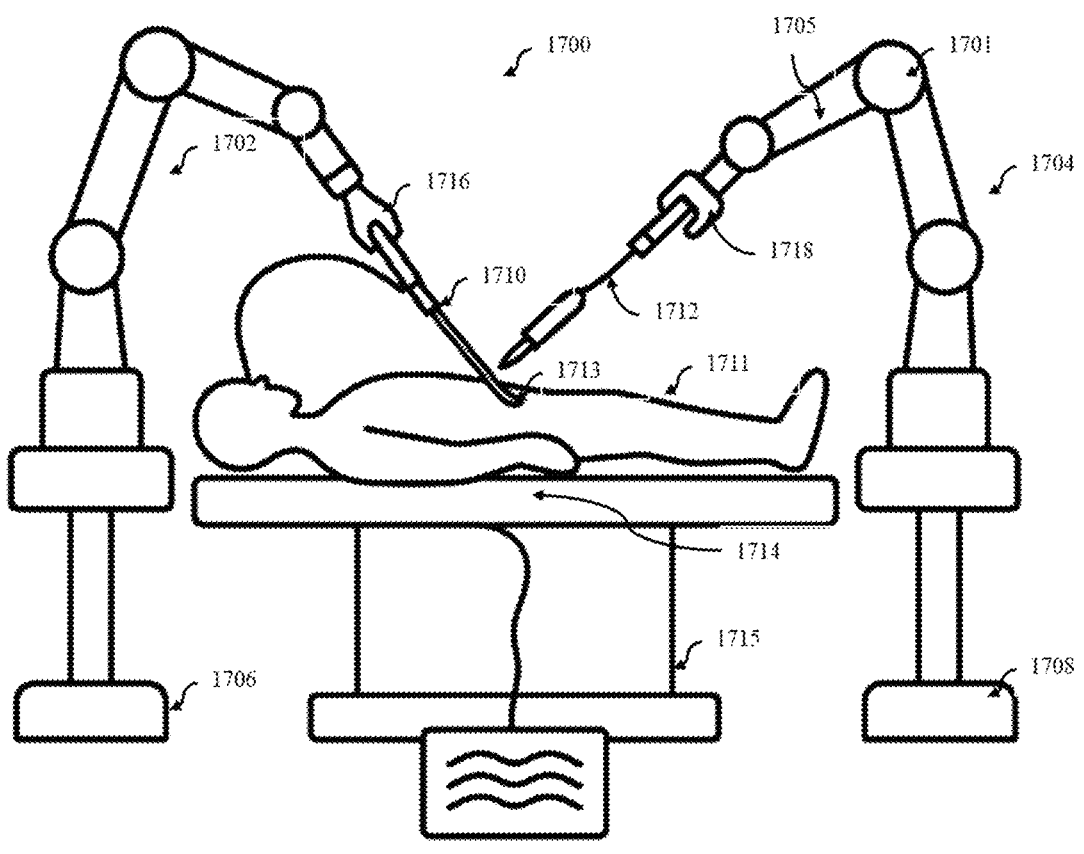
FIG. 17 illustrates a robotic surgical system configured for the implantation of an active implantable medical device, according to one or more embodiments.

FIG. 17 illustrates a robotic surgical system 1700 configured for the implantation of an active implantable medical device, according to one or more embodiments. The system comprises a first robotic arm 1702 and a second robotic arm 1704, each mounted on respective robot bases 1706 and 1708. These arms are equipped with end effectors, which may include robotic manipulators or grippers designed to handle endoscopic instruments and/or implant delivery tools.

The first end effector 1716 is operable with one or more tools 1712, such as a suture needle driver, grasping instrument, and/or a flexible endoscope. The second end effector 118 is configured to manipulate a sheath or catheter 1710, which may contain multiple lumens for guiding the tools 1712 (e.g., implant delivery tools) toward the target anatomical site. An electromagnetic (EM) generator 1714 is integrated into the robotic surgical system 1700 to produce an EM field detectable by sensors embedded within the implant delivery tool or the implant itself. For example, an EM sensor may be positioned on the distal tip of the driver tool or on the implantable device to provide real-time positional and orientation data. The EM generator 17114 may be embedded within the operating table 1715 or placed beneath the patient 1711 via a dedicated pad. The robotic arms 1702 and 1704 are precisely controlled to maintain axial alignment between the catheter 1710 and the tools 1712. This ensures that the proximal end of the catheter remains distal to the proximal ends of the tools, facilitating seamless instrument (e.g., AIMD) deployment. In one embodiment, the first robotic arm 1702 introduces the catheter 1710 through a designated access point—such as a percutaneous incision or anatomical conduit—and advances it toward the target site. The second robotic arm 1704 then deploys the tools 1712 through the catheter to perform tasks such as dissection, device (e.g., AIMD) anchoring, or suturing. The robotic arms may be actuated to move the catheter and tools axially and rotationally under the guidance of a surgeon operating from a control console. This enables dynamic adjustment during implantation procedures. During the navigation phase, the catheter 1710 and tools 1712 are advanced into the patient 1711, with the tools extending beyond the catheter's distal tip to reach the implantation site. Alternative navigation methods may include guide wire-assisted advancement through a working channel. Surgeons may utilize multimodal imaging—such as fluoroscopy, CT, MRI, or endoscopic video—to guide the robotic system during device placement. The tools 1712 (e.g., AIMD) are deployed through longitudinally aligned channels within the catheter to perform implantation, fixation, and any adjunct procedures. The robotic arms 1702 and 1704 may include three joints 1701 and three arm segments 1705, although configurations with more or fewer joints and segments are also contemplated to accommodate anatomical variability and procedural complexity.

Active Implantable Medical Devices (AIMDs) are assembled from multiple components manufactured at different facilities. There is a need to track each module throughout the manufacturing and supply chain. This creates a significant risk of counterfeit or mismatched components being introduced into the supply chain. Such incidents can compromise patient safety, result in regulatory non-compliance, and lead to device failure.

There is also a need to ensure the authenticity of modules and components to prevent the introduction of counterfeit parts and guarantee that only verified modules are used in the final assembly. Currently, there is no reliable, non-toxic, and biocompatible method to authenticate each module's origin and integrity, track components throughout manufacturing and assembly, and prevent unauthorized modules from being inserted into final devices.

The solution must function in high-assurance biomedical manufacturing environments and avoid introducing toxic substances that could later impact patient safety.

This work may require a hardware-based authentication system. Such a system could be embedded in different modules and components as needed. In one embodiment, the hardware-based authentication system is present in all components and modules. For example, components or modules may include built-in chips with tamper resistance, or even quantum-based ID systems. Each module may carry a unique, verifiable ID (e.g., a physical unclonable function or encrypted tag).

The hardware-based authentication system may include a tracking capability that can detect tampering or substitution. It is important to note that materials used for tracking (e.g., microchips, sealants, embedded quantum markers) must be non-toxic and biocompatible. Environmental robustness can be achieved using techniques such as hermetic sealing, nitrogen flushing, or vacuum isolation during the manufacturing process.

The term "biocompatible" refers to materials that do not trigger significant inflammation or immune rejection in a patient's body, do not release toxic substances, and maintain their function safely over time in the body's environment.

In one embodiment, the embedded identifier, chip, or similar hardware component could be designed to degrade upon tampering. It is also possible for hardware components encoding traceable, quantum-sensitive materials to lose functionality if exposed.

In another embodiment, the modules or components can be coated with temporal resistance-like coating (TRC) materials to monitor chain-of-custody. A temporal resistance-like coating is a special type of material layer or film designed to degrade, change, or lose effectiveness in a controlled way over time or in response to environmental conditions such as heat, moisture, pH, light, or mechanical stress. It temporally resists these changes—meaning it maintains integrity for a specific period or under certain conditions—and then deliberately breaks down or alters.

In hardware security mechanisms, a TRC coating can serve as an anti-tamper layer on chips, such as resin layers that degrade when exposed to heat or UV light, destroying circuits if someone attempts to open or probe them.

In an embodiment, an active implantable medical device (AIMD) along with other components, comprising a plurality of modules, wherein one or more modules comprises: a) a hardware-based authentication element uniquely identifying the module; b) a biocompatible encapsulation enclosing the authentication element; and c) a module tracking system configured to verify identity and integrity of the module prior to final assembly.

In an embodiment, the hardware-based authentication element comprises a physical unclonable function (PUF), RFID tag, or optically encoded microstructure.

In an embodiment, the biocompatible encapsulation includes a hermetic seal, vacuum chamber, or nitrogen-filled cavity.

In an embodiment, the module tracking system comprises a handheld or assembly-line reader configured to authenticate the module using a cryptographic handshake or physical signal.

In an embodiment, any tampering with the authentication element renders the module inoperable or flags it as invalid for assembly.

Figure 18A:
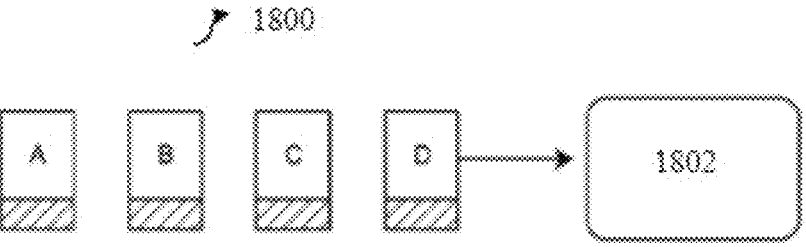
FIG. 18A represents an exemplary AIMD System with Secure Module Tracking and Authentication.

The accompanying FIG. 18A represents an exemplary AIMD System 1800 with individual modules labeled as A-D having an embedded unique ID or authentication marker and connected to a central control system that verifies module identity before final assembly. Although the example shows four modules, an AIMD system may include one, two, three, or more modules. It is also possible for each module to have its own control system to verify its authenticity. Alternatively, two or more modules may share a common control system to verify authenticity. Further, one or more modules with individual control systems can be connected to a single, centralized control system.

Figures 18B, 18C:
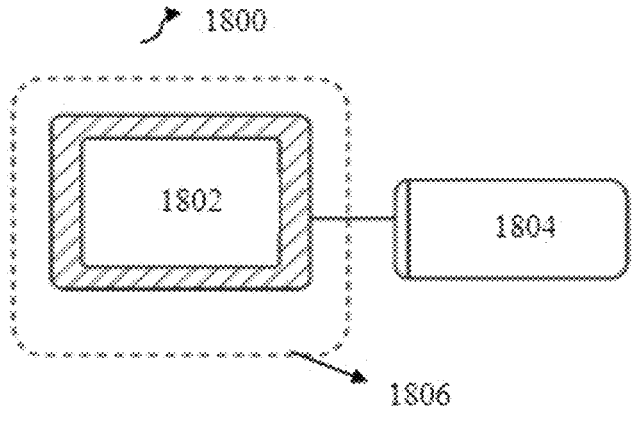
FIG. 18B illustrates an exemplary module authentication mechanism.
FIG. 18C shows an embodiment of the module authentication mechanism in a module.

FIG. 18B illustrates an exemplary module authentication mechanism. One or more modules contain an embedded authentication element, such as a chip or material tag (1802). A reader interface (1804) at the assembly line can verify the identity through mechanisms such as secure hardware handshakes or optical signatures. The authentication element can be surrounded by biocompatible packaging (1806), such as a tamper-evident seal. An optional polymer seal (not shown) may provide additional environmental shielding.

FIG. 18C shows an embodiment of the module authentication mechanism in a module. One or more modules may contain an embedded authentication element such as a chip or material tag (1702) made of TRC-like material. The authentication element can be surrounded by a TRC (1704). If tampering occurs or a change in environment is detect, the TRC degrades, breaking the seal and causing the circuit to fuse, which results in the failure of the reader interface (not shown) to retrieve the data.

In one embodiment, the active implantable medical device (AIMD) or its individual modules may be enclosed within a non-toxic sleeve or encapsulation to ensure biocompatibility and compliance with international safety standards. For example, the device may be manufactured in accordance with the European Union's Restriction of Hazardous Substances (RoHS) Directive, which limits the use of six hazardous materials in electrical and electronic equipment: Cadmium (Cd) to a maximum of 0.01% by weight, and Lead (Pb), Mercury (Hg), Hexavalent Chromium (Cr VI), Polybrominated Biphenyls (PBB), and Polybrominated Diphenyl Ethers (PBDE) each to a maximum of 0.1% by weight. Comparable regulations exist in other jurisdictions, including China RoHS, Japan RoHS (J-MOSS), Taiwan RoHS, South Korea RoHS, and Singapore RoHS. In the United States, while there is no federal RoHS equivalent, several states, such as California, have enacted similar restrictions. To further enhance security and traceability, the AIMD system may incorporate supply chain tracking technologies such as blockchain for immutable transaction records, RFID and NFC for real-time authentication, IoT sensors for environmental monitoring, and enterprise resource planning (ERP) systems for integrated traceability across manufacturing stages. These features collectively ensure that only verified, non-toxic, and traceable components are used in the final assembly of the AIMD, thereby enhancing patient safety and regulatory compliance.

The present disclosure provides a system and method for the controlled self-destruction or permanent deactivation of an AIMD upon reaching its end-of-life (EOL), particularly after the conclusion of a drug delivery cycle. The purpose of the self-destruction mechanism is to prevent illicit reuse, reverse engineering, and unsafe reimplantation of the device, while maintaining safety for patients and healthcare providers.

In one embodiment, the active implantable medical device (AIMD) comprises a self-destruction mechanism configured to be activated upon completion of a therapeutic cycle, such as the full discharge of a drug reservoir. The self-destruction mechanism is designed to render the AIMD permanently inoperable, thereby preventing reuse, reverse engineering, or unauthorized reimplantation, while ensuring biocompatibility and patient safety.

The self-destruction mechanism may be triggered by a control signal generated by a microcontroller or sensor module upon detection of a terminal event, such as the piston reaching its end-of-stroke position. The control signal initiates one or more destruct modalities.

Figure 19A:
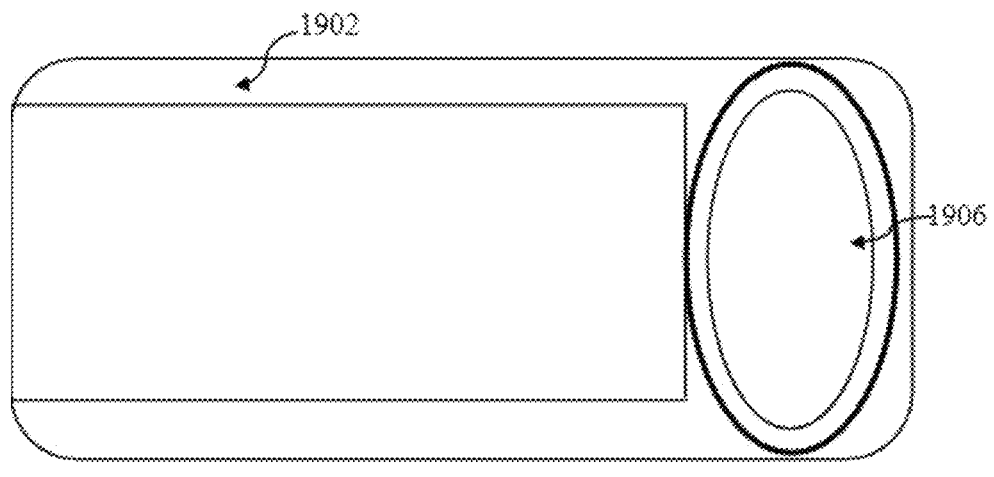
FIG. 19A illustrates a schematic cross-sectional view of an Active Implantable Medical Device comprising self-destruction mechanism.

FIG. 19A illustrates a schematic cross-sectional view of an Active Implantable Medical Device 1902 comprising self-destruction mechanism 1904.

In one embodiment, the AIMD includes a temporal resistance coating applied to one or more structural or functional components. The TRC is composed of a material that remains stable under physiological conditions but degrades upon exposure to specific environmental stimuli, such as atmospheric oxygen, ultraviolet or visible light, elevated temperature, or pH changes. Upon explantation, the TRC undergoes a controlled degradation process, leading to the disintegration of critical components such as the housing, circuitry, or interconnects.

Figure 19B:
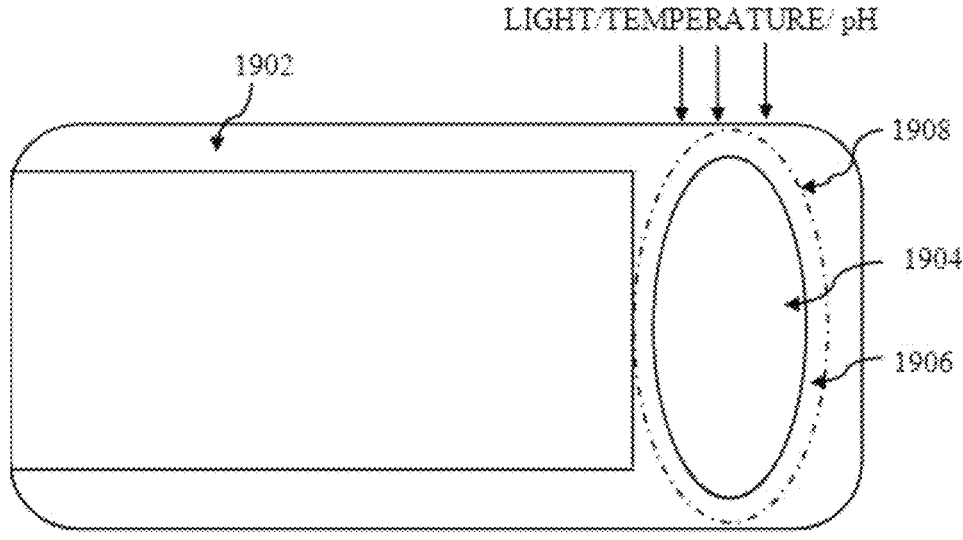
FIG. 19B illustrates a schematic view of a self-destruction mechanism incorporated within an Active Implantable Medical Device.

FIG. 19B illustrates a schematic view of a self-destruction mechanism incorporated within an Active Implantable Medical Device (AIMD), specifically highlighting the role of a Temporal Resistance Coating (TRC) in facilitating controlled device deactivation. The outermost boundary of the figure 1902 represents the AIMD itself, shown as a sealed, biocompatible enclosure optimized for subcutaneous implantation. Housed within this enclosure is a designated internal module self-destruction mechanism 1904, which may contain essential components such as microelectronic circuits, data storage elements, or structural elements integral to the device's therapeutic or functional operation. Encasing this module is the TRC layer 1906, composed of environmentally responsive material designed to remain inert during normal in vivo operation. However, the TRC is engineered to undergo degradation when exposed to specific environmental triggers such as atmospheric oxygen, UV or visible light, or shifts in pH—typically occurring upon device explantation or accidental exposure. The figure includes directional arrows 1908 entering the AIMD, symbolizing environmental intrusion (e.g., air, fluid, or radiation) that activates the TRC breakdown. This degradation is visually represented by fragmentation or disintegration of the coating layer, which in turn initiates the irreversible destruction, disconnection, or deactivation of the encapsulated module 1904.

In another embodiment, the AIMD comprises a microfabricated fuse circuit integrated into the electronic control system. Upon receiving the end-of-life signal, the fuse is selectively blown, thereby irreversibly severing electrical connectivity within the device. The fuse may be configured to disrupt power delivery, data communication, or control signal pathways, effectively disabling the device's operational capabilities.

Figure 20:
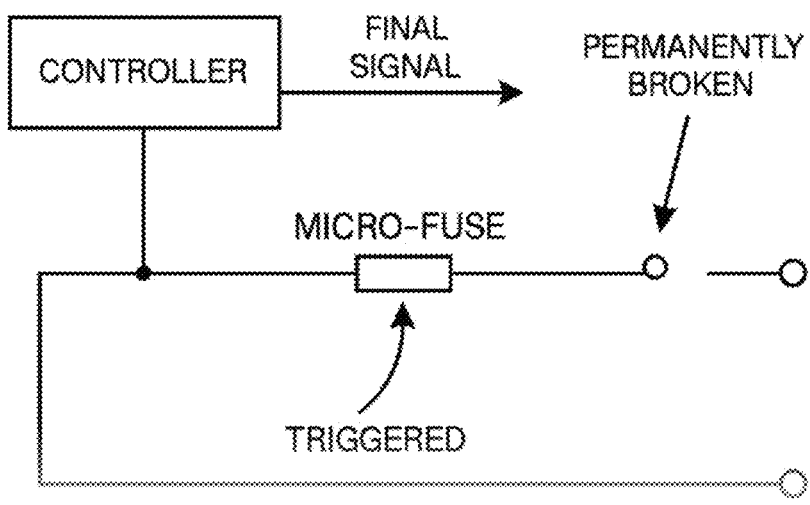
FIG. 20 presents a schematic representation of a circuit-based self-destruction mechanism integrated within an Active Implantable Medical Device.

FIG. 20 presents a schematic representation of a circuit-based self-destruction mechanism integrated within an Active Implantable Medical Device (AIMD), illustrating the use of a micro-fuse element to achieve permanent deactivation of the device's electronic functions after completion of its therapeutic role. The diagram depicts a simplified internal circuit layout, featuring a controller module tasked with monitoring the device's operational status. Embedded along the active electrical pathway between the power source and the core electronics is a micro-fuse, which serves as a critical control point. Upon detection of an end-of-life condition—such as full depletion of the drug reservoir or complete displacement of a piston—the controller initiates a final shutdown sequence by transmitting an activation signal to the micro-fuse. Once triggered, the fuse irreversibly severs the electrical connection, thereby disabling power and/or communication lines linked to the essential electronic subsystems. This action results in the permanent and non-reversible deactivation of the AIMD, preventing any possibility of reuse, recharging, or reverse engineering. Arrows in the schematic indicate the direction of signal transmission from the controller to the fuse and depict the break in the circuit that follows.

In yet another embodiment, the AIMD includes components fabricated from environmentally responsive materials that undergo structural breakdown upon exposure to non-physiological conditions. For example, materials may be selected to degrade in the presence of ambient air, moisture, or specific chemical agents encountered during explantation or sterilization. This degradation may result in fragmentation, delamination, or dissolution of internal components, thereby rendering the device non-functional.

In a further embodiment, the AIMD incorporates quantum-state-dependent subsystems that rely on quantum confinement or entanglement for functionality. Upon exposure to environmental transitions—such as changes in electro-magnetic fields, pressure, or temperature—the quantum state decoheres, resulting in irreversible loss of function. This mechanism ensures that the internal architecture of the AIMD becomes scrambled or unreadable, thereby preventing reverse engineering.

The self-destruction mechanism is configured to operate without generating heat, mechanical shock, or toxic by-products. The degradation process is gradual and confined within the structural boundaries of the AIMD. In some embodiments, the device may include a signaling mechanism, such as a low-energy RF beacon or visual indicator, to notify clinical personnel that the device has entered or completed the self-destruction phase.

In one embodiment, the active implantable medical device (AIMD) is further configured to detect whether the therapeutic agent contained within the device has exceeded its designated shelf life and, upon such detection, to render itself permanently inoperable. This functionality may be achieved through the integration of one or more technologies including, but not limited to: embedded RFID (Radio Frequency Identification) or NFC (Near Field Communication) tags within the medication packaging to store expiration data; dynamic codes such as QR codes or barcodes linked to a centralized database containing shelf-life information; environmental monitoring sensors capable of tracking storage conditions such as temperature, humidity, and light exposure to dynamically assess degradation risk; and integrated chemical sensors capable of detecting changes in the medication's composition indicative of expiration. Upon confirmation of expiration, the device initiates a self-destruction sequence to prevent administration of ineffective or unsafe medication. Additionally, the AIMD may incorporate an advanced self-diagnostic system designed to ensure operational integrity and patient safety. This system includes error detection algorithms, self-calibration routines, real-time monitoring of critical components, usage tracking, and wear-and-tear analysis to accurately determine the device's end-of-life. If an uncorrectable error is detected, the device automatically initiates a shutdown sequence, rendering itself inoperable. The system may further include a communication interface with wireless connectivity for remote monitoring, data logging, and transmission of diagnostic information. Power management features such as battery health monitoring, energy optimization, and emergency power-off capabilities are also included. A user interface may be provided with an intuitive display, interactive controls, and visual indicators—such as color changes—to alert users to device status or medication degradation. These features collectively ensure that only safe, effective, and authenticated devices are deployed, thereby enhancing patient safety and regulatory compliance.

This destruct mechanism ensures single-use integrity of the AIMD, enhances security against tampering, and supports regulatory compliance by preventing unauthorized reuse or analysis of the device post-explantation.

In an aspect, the disclosure relates to relates to a medical system designed for intelligent, automated drug dose titration based on real-time physiological data. This enables precise, adaptive drug dosing that responds instantly to the patient's needs, maximizing efficacy and safety throughout therapy. The system comprises a drug delivery pump, which may be configured as either an implantable or wearable unit, comprising a drug reservoir for storing a therapeutic agent and a drug dispensing mechanism that controllably administers the agent into the patient. Real-time physiological data transforms PK/PD modeling from a static prediction tool into a dynamic, continuously learning system. One or more physiological sensors are integrated with the system and are configured to measure drug concentration in the patient's interstitial fluid, which serves as a proxy for plasma drug levels. Sensor data is processed by a control processor, which comprises memory for storing historical sensor readings and patient-specific treatment parameters, and an artificial intelligence (AI) engine capable of executing dose titration algorithms. The AI engine estimates key pharmacokinetic and pharmacodynamic (PK/PD) parameters, comprising the absorption rate constant (ka), elimination rate constant (ke), and minimum effective concentration (Cmin), using predictive modeling techniques. Based on these parameters, the AI engine determines appropriate dosage adjustments and generates control signals to actuate the drug dispensing mechanism. The AI engine iteratively updates its predictive model based on feedback from subsequent sensor readings, enabling continuous optimization of drug therapy.

In some implementations, the pump may comprise dual reservoirs to facilitate combination therapies, with the AI engine dynamically determining not only the dosage but also the selection and sequencing of drugs. The system may further incorporate external communication interfaces, allowing integration with smartphones, hospital systems, or cloud-based medical records for remote monitoring, clinician oversight, and software updates. A patient-specific baseline model may be initialized at the time of implantation or application, using genomic, proteomic, or clinical data to individualize the therapy from the outset.

In some embodiments, following each drug titration event, the system re-evaluates the pharmacokinetic and pharmacodynamic profile under the updated dosing conditions. The artificial intelligence engine reassesses the parameters such as absorption rate, elimination rate, and effective concentration thresholds to refine the predictive model. This ongoing reassessment ensures that the drug delivery strategy remains aligned with the patient's dynamic physiological state.

In an embodiment, the system comprises a dedicated safety module capable of detecting anomalous or unsafe operating conditions and initiating corrective actions such as halting drug delivery, alerting medical personnel, or activating secure override protocols. Additional safety features comprise a clinician override interface, a fail-safe shutoff mechanism that disables drug administration in response to specific threshold events, and an end-of-life (EOL) self-deactivation protocol triggered by battery depletion, reservoir exhaustion, or sensor degradation. Furthermore, redundancy in sensor data processing and constrained learning rates are implemented to prevent unsafe or erratic dose escalations. The disclosed system is particularly advantageous in managing chronic diseases such as diabetes, cancer, Parkinson's disease, and epilepsy, where precise, responsive, and individualized drug delivery is critical to therapeutic success.

An embodiment relates to an active implantable medical device (AIMD) system comprising: a) a plurality of modules configured to perform therapeutic and/or diagnostic functions; and b) at least one of said modules comprising: i. a hardware-based authentication element configured to uniquely identify the module; ii. a biocompatible encapsulation enclosing the authentication element; and iii. a module tracking system configured to verify the identity and integrity of the module prior to final assembly of the AIMD; wherein the authentication element is further configured to render the module inoperable or mark it as invalid for assembly upon detection of tampering or substitution.

In an embodiment, the hardware-based authentication element comprises a physical unclonable function (PUF), a radio-frequency identification (RFID) tag, or an optically encoded microstructure.

In another embodiment, the biocompatible encapsulation comprises a hermetically sealed enclosure, a vacuum-isolated cavity, or a nitrogen-filled chamber.

In yet another embodiment, the module tracking system comprises a reader configured to authenticate the module via a cryptographic handshake or by detecting a physical signal from the authentication element.

In yet another embodiment, the authentication element is configured to degrade or become unreadable upon exposure to environmental conditions indicative of tampering.

In yet another embodiment, the authentication element is embedded within a temporal resistance coating (TRC) configured to degrade upon exposure to heat, light, pH, or mechanical stress.

In yet another embodiment, the authentication element comprises a quantum-sensitive material configured to lose functionality upon exposure to environmental transitions.

In yet another embodiment, each module comprises an individual control system configured to verify its own authenticity.

In yet another embodiment, two or more modules share a common control system configured to verify the authenticity of each module prior to final assembly.

In yet another embodiment, the authentication element is enclosed within a tamper-evident seal or a polymer-based environmental shield.

An embodiment relates to an active implantable medical device (AIMD) comprising: a drug delivery subsystem configured to administer a therapeutic agent to a patient; a sensor or controller configured to detect completion of a therapeutic delivery cycle based on one or more terminal event conditions associated with the drug delivery subsystem; and a self-destruction mechanism operatively coupled to the controller and configured to be irreversibly activated in response to detection of the terminal event condition, wherein the self-destruction mechanism is configured to permanently disable at least one functional component of the AIMD, thereby preventing reuse, reverse engineering, or unauthorized reimplantation.

In an embodiment, the terminal event condition comprises full depletion of the therapeutic agent or a piston reaching its end-of-stroke position within the drug delivery subsystem.

In yet another embodiment, the self-destruction mechanism comprises a temporal resistance coating (TRC) applied to one or more internal or external components of the AIMD, the TRC being stable under physiological conditions and configured to degrade upon exposure to environmental stimuli selected from atmospheric oxygen, ultraviolet or visible light, pH change, moisture, or temperature fluctuation.

In yet another embodiment, degradation of the temporal resistance coating results in mechanical or electrical disintegration of a critical component, thereby causing irreversible loss of device functionality.

In yet another embodiment, the self-destruction mechanism comprises a micro-fabricated fuse circuit electrically connected to the core electronics of the device, the fuse being configured to receive an activation signal from the controller and, upon activation, to permanently sever one or more electrical pathways associated with power delivery or data communication.

In yet another embodiment, the self-destruction mechanism comprises a structural component fabricated from an environmentally responsive material configured to undergo irreversible breakdown upon exposure to non-physiological conditions encountered during explantation or sterilization.

In yet another embodiment, the self-destruction mechanism comprises one or more quantum-state-dependent components whose functionality is based on quantum confinement, coherence, or entanglement, and wherein exposure to environmental transitions such as electromagnetic interference or pressure change causes decoherence and irreversible loss of function.

In yet another embodiment, activation of the self-destruction mechanism is accompanied by a signaling event selected from: (a) emission of a low-energy radiofrequency (RF) beacon; (b) activation of a visual indicator such as an LED; or (c) a magnetically detectable change in state, to notify clinical personnel of device deactivation.

In yet another embodiment, the self-destruction mechanism is biocompatible and non-toxic, and is configured to avoid introducing thermal, mechanical, or chemical hazards to the patient or surrounding tissue upon activation.

In yet another embodiment, the controller comprises a microcontroller integrated with memory and firmware logic configured to perform device state monitoring, detect terminal event conditions, and initiate timed or conditional triggering of the self-destruction mechanism.

An embodiment relates to a system comprising a robotic manipulator comprising a first robotic arm configured to access a target anatomical site within a body of a mammal; an active implantable medical device (AIMD) comprising a biocompatible housing, a drug chamber, a piston, an electronic module, and a channel port; a channel operatively coupled to the channel port and configured to deliver a therapeutic agent to the target anatomical site; and an imaging and navigation system configured to guide the robotic manipulator; and wherein the robotic manipulator is configured to create a pocket, place the AIMD into the pocket, route the channel to the target anatomical site, and secure the AIMD and the channel in place.

In an embodiment, the channel comprises at least one of a bacterial filter, a check valve, and a flow control regulator.

In yet another embodiment, the further comprises a second robotic arm configured to manipulate a sheath for routing the AIMD toward the target anatomical site.

In yet another embodiment, the imaging and navigation system comprises modality of at least one of fluoroscopy, computed tomography (CT), magnetic resonance imaging (MRI), and ultrasound.

In yet another embodiment, the robotic manipulator comprises end-effectors configured for dissection, implantation, and suturing.

In yet another embodiment, the system further comprises an electromagnetic generator and a sensor configured to track a position of one of the AIMD and a surgical tool during implantation.

In yet another embodiment, the robotic manipulator is configured to connect one or more components of the AIMD and deliver a test bolus to verify channel patency and function of the one or more components.

In yet another embodiment, the channel is configured to access the target anatomical site selected from at least one of an intrathecal space, a peritoneal cavity, and an intravascular compartment.

In yet another embodiment, the robotic manipulator operates under closed-loop control to maintain alignment between the channel and an implant delivery tool.

In yet another embodiment, the robotic manipulator is actuated to perform minimally invasive dissection through one or more incisions under real-time imaging guidance.

An embodiment relates to a system comprising a robotic actuator comprising a robotic arm with at least one articulated joint and an end-effector configured to affix an active wearable medical device (AWMD) onto a skin of a body of a mammal; a sensor module configured to collect anatomical data from a target region on the body; and a control unit operatively coupled to the robotic actuator and the sensor module; and wherein the control unit analyzes the anatomical data to identify an optimized placement site within the target region and generates a control signal to guide the robotic actuator to affix the AWMD at the optimized placement site.

In an embodiment, the sensor module acquires at least one of skin texture, surface curvature, tissue compliance, and subcutaneous vasculature data.

In yet another embodiment, the robotic actuator comprises one or more embedded force sensors configured to regulate affixation pressure.

In yet another embodiment, the AWMD comprises a drug chamber, an osmotic agent chamber, a piston, a valve module, an electronic module, and a machine learning model.

In yet another embodiment, the control unit selects the optimized placement site based on at least one of drug absorption efficiency, prior site usage, and avoidance of sensitive regions.

In yet another embodiment, the robotic actuator is configured to reposition the AWMD based on at least one of patient posture, dosing history, and a feedback from the sensor module.

In yet another embodiment, system further comprises a feedback verification module configured to detect successful adhesion and initiate device diagnostics.

In yet another embodiment, the AWMD is selected from at least one of a microneedle array, a transdermal patch, and a wearable infusion pump.

In yet another embodiment, the machine learning model of the AWMD is configured to trigger alerts upon exceeding dosage thresholds.

In yet another embodiment, the robotic actuator, the sensor module, and the control unit operate in a closed-loop control system for precision-guided placement and verification.

An embodiment relates to a medical system configured for automated drug dose titration in a patient, the system comprising a drug delivery pump comprising a drug reservoir configured to store a therapeutic agent and a drug dispensing mechanism operatively coupled to the drug reservoir and configured to controllably release the therapeutic agent into the patient; one or more physiological sensors configured to measure a drug concentration in interstitial fluid of the patient and generate sensor data corresponding to the measured drug concentration; a control processor operatively coupled to the one or more physiological sensors and the drug dispensing mechanism, the control processor comprising a memory storing historical sensor data and patient-specific parameters and an artificial intelligence engine configured to process the sensor data to estimate pharmacokinetic and pharmacodynamic parameters of the therapeutic agent, the parameters including at least an absorption rate constant, an elimination rate constant, and a minimum effective concentration, determine a current dosage adjustment based on the pharmacokinetic and pharmacodynamic parameters using a predictive model, generate a control signal to activate the drug dispensing mechanism to deliver the adjusted dosage, and iteratively update the predictive model based on feedback from subsequent sensor data; wherein the system further comprises one or more safety modules configured to detect anomalous or unsafe conditions and initiate one or more safety responses selected from halting drug delivery, sending alerts to a caregiver, or initiating a secure override protocol.

In an embodiment, the artificial intelligence engine comprises a reinforcement learning model configured to learn optimal dosage strategies by maximizing therapeutic efficacy over time.

In yet another embodiment, the artificial intelligence engine further comprises a supervised learning model trained on historical patient data and clinical outcomes to predict adverse drug reactions.

In yet another embodiment, the safety module includes an end-of-life deactivation circuit configured to detect exhaustion of the drug reservoir or battery power and irreversibly disable the drug dispensing mechanism.

In yet another embodiment, the drug dispensing mechanism comprises a microfluidic or piezoelectric pump configured for microliter-precision actuation based on the control signal from the control processor.

In yet another embodiment, the system further comprises a clinician override interface configured to receive override commands from an external device via a secure wireless protocol and temporarily or permanently disable the artificial intelligence-driven dosage control.

In yet another embodiment, the control processor is configured to stratify patient response data into therapy response clusters using unsupervised learning algorithms and modify treatment regimens accordingly.

In yet another embodiment, the control processor receives patient-specific initialization parameters including genetic, proteomic, or demographic data to personalize the starting dose model.

In yet another embodiment, the system integrates with a remote server or electronic medical record system to transmit therapy data for clinical monitoring and receive software or model updates for the artificial intelligence engine.

An embodiment relates to a computer-implemented method for automated drug dose titration in a patient, the method comprising: receiving, from one or more physiological sensors, real-time data corresponding to a concentration of a therapeutic agent in interstitial fluid of the patient; estimating, by a control processor comprising an artificial intelligence engine, pharmacokinetic and pharmacodynamic parameters based on the received data, the parameters including at least an absorption rate constant, an elimination rate constant, and a minimum effective concentration; determining, by the artificial intelligence engine, a dose adjustment based on the estimated parameters using a predictive model; generating a control signal to actuate a drug dispensing mechanism of a drug delivery pump to deliver the adjusted dosage to the patient; and updating the predictive model based on feedback derived from subsequent physiological sensor data to optimize future dosing decisions.

In an embodiment, the method further comprises initializing a patient-specific baseline model prior to first drug administration, wherein the model is derived from genomic, proteomic, or clinical diagnostic data.

In yet another embodiment, the artificial intelligence engine comprises a reinforcement learning model that continuously improves dosage selection based on cumulative therapy outcomes.

In yet another embodiment, the artificial intelligence engine comprises a supervised learning model trained to predict adverse drug reactions based on historical patient data and treatment outcomes.

In yet another embodiment, determining the dose adjustment comprises selecting and sequencing drug delivery from a plurality of drug reservoirs configured in the drug delivery pump.

In yet another embodiment, the method further comprises detecting, by a safety module, an anomalous condition comprising one or more of: excessive drug accumulation, sensor failure, or patient non-responsiveness; and halting drug administration in response to the detection.

In yet another embodiment, the method further comprises receiving a clinician override command from an external device, and temporarily disabling automated dose titration control in response to the override command.

In yet another embodiment, the method further comprises triggering a fail-safe shutoff or end-of-life deactivation procedure when the system detects at least one of battery depletion, reservoir exhaustion, or sensor degradation.

In yet another embodiment, the drug dispensing mechanism is a microfluidic or piezoelectric pump configured for microliter-precision drug delivery.

In yet another embodiment, the method further comprises transmitting dosing history and sensor data to a remote server or electronic medical record system for clinical monitoring and software update delivery.

In yet another embodiment, the method further comprises re-evaluating the pharmacokinetic and pharmacodynamic parameters after each dosage titration based on updated physiological sensor data, wherein the re-evaluation comprises recalculating at least the absorption rate constant, the elimination rate constant, and the minimum effective concentration to refine subsequent dosage decisions.

INCORPORATION BY REFERENCE

All references, including granted patents and patent application publications, referred herein are incorporated herein by reference in their entirety.

What is claimed is:

1. A system comprising:
a medical device that is not configured to be implanted in a body of a mammal, comprising:
a drug chamber comprising a drug;
a compressible piston located adjacent to the drug chamber and comprising a cross sectional area, a drug chamber-facing surface and an opposite surface; and
a valve to allow flow of the drug from the drug chamber to outside the medical device through one or more drug outlets;
wherein the compressible piston is configured to deform such that the drug chamber-facing surface moves toward the drug chamber when the valve is opened, and the opposite surface follows when the valve is closed, resulting in a net longitudinal displacement of the piston as a whole.

2. The system of claim 1, further comprising a fluid chamber containing a liquid.

3. The system of claim 2, wherein the fluid chamber comprises an expandable elastomeric bladder and a rigid reservoir.

4. The system of claim 2, wherein the fluid chamber comprises a Hydrogel hydrogel-containing reservoir.

5. The system of claim 2, wherein the fluid chamber comprises a microfluidic reservoir.

6. The system of claim 2, wherein the fluid chamber comprises an active operated chamber.

7. The system of claim 2, wherein the fluid chamber comprises a passive operated chamber.

8. The system of claim 1, further comprising a catheter configured to deliver the drug to a specific anatomical site.

9. The system of claim 8, wherein the catheter is configured for targeted administration of the drug.

10. The system of claim 1, further comprising an attachment component adapted to secure at least a portion of the system to the mammal during discharge of the drug.

11. The system of claim 1, wherein the drug chamber comprises a plurality of drug chambers.

12. The system of claim 11, wherein the system is configured for sequential or combined discharge from the plurality of drug chambers.

13. The system of claim 8, wherein the system comprises a real-time imaging and navigation guidance device.

14. The system of claim 13, wherein the real-time imaging and navigation guidance device is configured to aid placement of the catheter and monitor dispersion of the drug in real-time.

15. The system of claim 10, wherein the attachment component comprises an adhesive layer.

16. The system of claim 10, wherein the attachment component comprises one of a mechanical fastener, a wearable strap, a wearable band, and a skin micro-anchor.

17. The system of claim 1, further comprising a fluid chamber containing a liquid, wherein the fluid chamber is fluidically connected to a pump, a microfluidic channel, or a delivery port.

18. The system of claim 1, further comprising a fluid chamber containing a liquid, wherein the fluid chamber is fluidically connected to a pump.

19. The system of claim 1, wherein the valve comprises an electrically actuated valve operable by a motor.

20. The system of claim 1, further comprising one or more sensors configured to monitor at least one of temperature, electrical conductivity, or displacement of the compressible piston.

\* \* \* \* \*